United States Patent
Xu et al.

(10) Patent No.: US 7,626,031 B2
(45) Date of Patent: Dec. 1, 2009

(54) SUBSTITUTED 3-(DIARYLMETHYLENE)INDOLIN-2-ONES AND METHODS OF THEIR USE

(75) Inventors: Wei Xu, Danville, CA (US); Erick Wang Co, Redwood City, CA (US); John M. Nuss, Danville, CA (US); Moon Hwan Kim, Palo Alto, CA (US); Rhett Ronald Klein, San Francisco, CA (US); Donna Tra Le, San Jose, CA (US); Amy Lew Tsuhako, Milpitas, CA (US); Jason Jevious Parks, Sacramento, CA (US); Zhaoyang Wen, San Francisco, CA (US); Wei Cheng, San Jose, CA (US)

(73) Assignee: Symphony Evolution, Inc., Rockville, MD (US)

( * ) Notice: Subject to any disclaimer, the term of this patent is extended or adjusted under 35 U.S.C. 154(b) by 530 days.

(21) Appl. No.: 10/533,555

(22) PCT Filed: Nov. 14, 2003

(86) PCT No.: PCT/US03/36567

§ 371 (c)(1),
(2), (4) Date: May 2, 2005

(87) PCT Pub. No.: WO2004/050681

PCT Pub. Date: Jun. 17, 2004

(65) Prior Publication Data

US 2006/0122171 A1    Jun. 8, 2006

Related U.S. Application Data

(60) Provisional application No. 60/426,680, filed on Nov. 15, 2002, provisional application No. 60/470,674, filed on May 14, 2003.

(51) Int. Cl.
*C07D 401/00* (2006.01)
*A61K 31/445* (2006.01)
(52) U.S. Cl. ..................... 546/196; 514/320
(58) Field of Classification Search ............... 546/196; 514/320

See application file for complete search history.

(56) References Cited

U.S. PATENT DOCUMENTS

| 6,114,371 | A | 9/2000 | Tang et al. |
|---|---|---|---|
| 6,268,391 | B1 | 7/2001 | Dickerson et al. |
| 6,313,158 | B1 | 11/2001 | Tang et al. |
| 6,316,429 | B1 | 11/2001 | Tang et al. |
| 6,316,635 | B1 | 11/2001 | Tang et al. |
| 6,469,032 | B2 | 10/2002 | Tang et al. |
| 6,482,848 | B2 | 11/2002 | Moon et al. |
| 6,486,185 | B1 | 11/2002 | McMahon et al. |
| 6,569,868 | B2 | 5/2003 | Tang et al. |
| 6,689,806 | B1 * | 2/2004 | Tang et al. .................. 514/418 |
| 2002/0156083 | A1 | 10/2002 | Tang et al. |
| 2002/0156292 | A1 | 10/2002 | Tang et al. |

FOREIGN PATENT DOCUMENTS

| WO | WO9850356 | 11/1998 |
|---|---|---|
| WO | WO9961422 | 12/1999 |
| WO | WO0004901 | 3/2000 |
| WO | WO0056709 | 9/2000 |
| WO | WO0137820 | 5/2001 |
| WO | WO0164681 | 7/2001 |
| WO | WO0194312 | 12/2001 |

OTHER PUBLICATIONS

F. Z. Dorwald Side Reactions in Organic Synthesis: A Guide to Successful Synthesis Design 2005, Wiley-VCH Verlag GmbH & Co. KGaA, Weinheim.*

* cited by examiner

*Primary Examiner*—Rita J. Desai
*Assistant Examiner*—John Mabry
(74) *Attorney, Agent, or Firm*—McDonnell Boehnen Hulbert & Berghoff LLP

(57) ABSTRACT

The present invention provides compounds for modulating protein kinase enzymatic activity for modulating cellular activities such as proliferation, differentiation, programmed cell death, migration and chemoinvasion. More specifically, the invention provides oxindole derivatives which inhibit, regulate and/or modulate kinase receptor, particularly VEGF receptor 2 (Flk-1/KDR), FGFR1, and PDGFR (alpha and beta), signal transduction pathways related to the changes in cellular activities as mentioned above, compositions which contain these compounds, and methods of using them to treat kinase-dependent diseases and conditions.

19 Claims, No Drawings

SUBSTITUTED 3-(DIARYLMETHYLENE)INDOLIN-2-ONES AND METHODS OF THEIR USE

CROSS REFERENCE TO RELATED APPLICATIONS

This application claims priority to U.S. Provisional Patent Application No. 60/426,680 filed, Nov. 15, 2002, titled "Kinase Modulators." This application is also claims priority to U.S. Provisional Patent Application No. 60/470,674 filed, May 14, 2003, titled "Kinase Modulators." Each of the aforementioned patent applications is incorporated herein by reference for all purposes.

BACKGROUND OF THE INVENTION

1. Field of the Invention

This invention relates to compounds for modulating protein kinase enzymatic activity for modulating cellular activities such as proliferation, differentiation, programmed cell death, migration and chemoinvasion. Even more specifically, the invention relates to compounds which inhibit, regulate and/or modulate kinase signal transduction pathways related to the changes in cellular activities as mentioned above, compositions which contain these compounds, and methods of using them to treat kinase-dependent diseases and conditions.

2. Summary of Related Art

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Protein kinases are enzymes that catalyze the phosphorylation of proteins, in particular, hydroxy groups on tyrosine, serine and threonine residues of proteins. The consequences of this seemingly simple activity are staggering; cell differentiation and proliferation; i.e., virtually all aspects of cell life in one way or another depend on protein kinase activity. Furthermore, abnormal protein kinase activity has been related to a host of disorders, ranging from relatively non-life threatening diseases such as psoriasis to extremely virulent diseases such as glioblastoma (brain cancer).

Protein kinases can be categorized as receptor type or non-receptor type. Receptor-type tyrosine kinases have an extracellular, a transmembrane, and an intracellular portion, while non-receptor type tyrosine kinases are wholly intracellular.

Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and beta-receptors, CSFIR, c-kit and FLK-II. Then there is the FLK family, which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., DN&P 7(6):334-339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, Oncogene, 8:2025-2031 (1993), which is hereby incorporated by reference.

Since protein kinases and their ligands play critical roles in various cellular activities, deregulation of protein kinase enzymatic activity can lead to altered cellular properties, such as uncontrolled cell growth, associated with cancer. In addition to cancer altered kinase signaling is implicated in numerous other pathological diseases. These include, but not limited to: immunological disorders such as rheumatoid arthritis, graft-host diseases, multiple sclerosis, psoriasis; cardiovascular diseases such as atherosclerosis, myocardioinfarction, ischemia, stroke and restenosis; other inflammatory and degenerative diseases such as interbowel diseases, osteoarthritis, macular degeneration, diabetic retinopathy. Therefore, both receptor and non-receptor protein kinases are attractive targets for small molecule drug discovery.

One particularly attractive goal for therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stroma cancers. Gleevec is a selective Abl kinase inhibitor.

Attractive targets for modulation include VEGF receptor 2 (Flk-1/KDR), FGFR1, and PDGFR (alpha and beta). These three receptor tyrosine kinases have been implicated in blood vessel formation and proliferation (angiogenesis). Angiogenesis is associated with and required for the growth of malignant solid tumors, and has also been implicated in the development of diabetic retinopathy and rheumatoid arthritis, for example, (see: Cherrington J M, Strawn L M, and Shawver L K. New paradigms for the treatment of cancer: the role of anti-angiogenesis agents. Adv Cancer Res (2000)79:1-38; Ciulla T A, et al. Ocular perfusion abnormalities in diabetes. Acta Ophthalmol Scand (2002) 80:468-77; Walsh D A, Haywood L. Angiogenesis: a therapeutic target in arthritis. Curr Opin Investig Drugs (2001) 2:1054-63, all incorporated by reference herein for all purposes). Therefore, compounds and their formulations that modulate such receptors should be useful in the treatment of cancer, rheumatoid arthritis and visual impairment due to diabetic retinopathy, as well as the other indications as outlined in paragraph [0007] above.

Evidence for a direct role of VEGF and its receptor (Flk-1/KDR) in angiogenesis has been well-documented. It has been shown that disruption of VEGF signaling (with either anti-VEGF antibodies or soluble VEGF receptors) can inhibit neovascularization and compromise existing tumor vasculature, resulting in inhibition of tumor growth (see: Hanahan D. Signaling vascular morphogenesis and maintenance. Science (1997) 277:48-50; Holash J, et al. Vessel cooption, regression, and growth in tumors mediated by angiopoietins and VEGF. Science (1999) 284:1994-8; Gale N W, Yancopoulos G D. Growth factors acting via endothelial cell-specific receptor tyrosine kinases: VEGFs, angiopoietins, and ephrins in vascular development. Genes Dev (1999) 13:1055-66, all incorporated by reference herein for all purposes). Also, several inhibitors of the kinase activity of Flk-1/KDR have shown anti-tumor activity in rodents (see: Laird, A. D. Cancer Res (2000) 60:4152-60; Wood, J. M., Cancer Res (2000) 60:2178-89, both incorporated herein for all purposes).

Kinases, FGF and PDGF, also play important roles in angiogenesis, sometimes in concert with VEGF. Although FGF knockout mice have no apparent defects related to impaired angiogenesis, FGF2 is clearly an angiogenic factor in vivo (see: Klint P, Claesson-Welsh L., Signal transduction by fibroblast growth factor receptors. Front Biosci (1999) 4:D165-77, herein incorporated by reference for all purposes). Also, FGF can act synergistically with VEGF to induce the expression of VEGF. Kinases, PDGF and PDGFR, are expressed in microvascular endothelial cells during angiogenesis (see: Sato N, et al. Platelet-derived growth factor indirectly stimulates angiogenesis in vitro. Am J Pathol (1993) 142:1119-30; Lindahl P, et al. Pericyte loss and microaneurysm formation in PDGF-B-deficient mice. Science (1997) 277:242-5, both incorporated by reference herein for all purposes). Like FGF, PDGF stimulates angiogenesis by up-regulating VEGF production. PDGF also stimulates the proliferation of pericytes and fibroblast-like cells surrounding endothelium. FGF and PDGF are also tumor cell mitogens, and their receptors are expressed in a variety of human cancers (see: Singh R K, et al. Cell density-dependent regulation of basic fibroblast growth factor expression in human renal cell carcinoma cells. Cell Growth Differ (1996) 7:397-404; Hermanson M, et al. Platelet-derived growth factor and its receptors in human glioma tissue: expression of messenger RNA and protein suggests the presence of autocrine and paracrine loops. Cancer Res (1992) 52:3213-9, both incorporated by reference herein for all purposes).

Accordingly, the identification of small-molecule compounds that specifically inhibit, regulate and/or modulate the signal transduction of kinases, for example VEGF receptor 2 (Flk-1/KDR), FGFR1, and PDGFR (alpha and beta), is desirable as a means to treat or prevent disease states associated with abnormal cell proliferation and is an object of this invention.

SUMMARY OF THE INVENTION

The present invention provides compounds for modulating kinase activity and methods of treating diseases mediated by kinase activity, for example VEGF receptor 2 (Flk-1/KDR), FGFR1, and PDGFR (alpha and beta), utilizing the compounds and pharmaceutical compositions thereof. Diseases mediated by kinase activity include, but are not limited to, diseases characterized in part by abnormal levels of cell proliferation (i.e. tumor growth), programmed cell death (apoptosis), cell migration and invasion and angiogenesis associated with tumor growth.

In another aspect, the invention provides methods of screening for modulators of kinase activity. The methods comprise combining a composition of the invention, a kinase, and at least one candidate agent and determining the effect of the candidate agent on the kinase activity.

In yet another aspect, the invention also provides pharmaceutical kits comprising one or more containers filled with one or more of the ingredients of pharmaceutical compounds and/or compositions of the present invention, including, one or more kinase enzyme activity modulators as described herein. Such kits can also include, for example, other compounds and/or compositions (e.g., diluents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

In still yet another aspect, the invention also provides a diagnostic agent comprising a compound of the invention and, optionally, pharmaceutically acceptable adjuvants and excipients.

These and other features and advantages of the present invention will be described in more detail below.

DETAILED DESCRIPTION OF THE INVENTION

The compositions of the invention are used to treat diseases associated with abnormal and or unregulated cellular activities, in particular those related to kinase activity, for example VEGF receptor 2 (Flk-1/KDR), FGFR1, and PDGFR (alpha and beta). Disease states which can be treated by the methods and compositions provided herein include, but are not limited to, cancer (further discussed below), immunological disorders such as rheumatoid arthritis, graft-host diseases, multiple sclerosis, psoriasis; cardiovascular diseases such as atherosclerosis, myocardioinfarction, ischemia, stroke and restenosis; other inflammatory and degenerative diseases such as interbowel diseases, osteoarthritis, macular degeneration, diabetic retinopathy.

It is appreciated that in some cases the cells may not be in a hyper- or hypo-proliferative and/or migratory state (abnormal state) and still require treatment. For example, during wound healing, the cells may be proliferating "normally", but proliferation and migration enhancement may be desired. Alternatively, reduction in "normal" cell proliferation and/or migration rate may be desired.

Embodiment [0021]: The present invention comprises a compound for modulating kinase activity of Formula I,

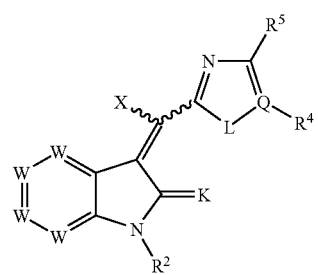

I or a pharmaceutically acceptable salt, hydrate, or prodrug thereof, wherein, each W is independently N or $CR^1$;

each $R^1$ is independently selected from —H, halogen, trihaloalkyl, —CN, —NH$_2$, —NO$_2$, —OR$^6$, —N=CNR$^6$R$^7$, —N(R$^6$)C(=NR$^8$)NR$^6$R$^7$, —SR$^6$, —S(O)$_{1-2}$R$^6$, —SO$_2$NR$^6$R$^7$, —CO$_2$R$^6$, —C(O)NR$^6$R$^7$, —C(O)N(OR$^6$)R$^7$, —C(=NR$^8$)NR$^6$R$^7$, —N(R$^6$)SO$_2$R$^7$, —NC(O)R$^6$, —NCO$_2$R$^6$, —C(O)R$^7$, —R$^7$, and —A—R$^7$; provided at least one of R$^1$ is —A—R$^7$, wherein, only for said at least one —A—R$^7$, R$^7$ must be an optionally substituted heteroalicyclic ring, and any nitrogen of said optionally substituted heteroalicyclic ring cannot be directly bound to A;

A is O, S(O)$_{0-2}$, and NR$^6$;

L is O, S(O)$_{0-2}$, or NR$^3$;

Q is C or N, when Q is N, then R$^4$ does not exist;

R$^2$ and R$^3$ are each independently —H or —R$^7$;

R$^4$ and R$^5$ are each independently selected from —H, —OR$^6$, —NR$^6$R$^7$, —S(O)$_{0-2}$R$^6$, —SO$_2$NR$^6$R$^7$, —CO$_2$R$^6$, —C(O)NR$^6$R$^7$, —N(R$^6$)SO$_2$R$^6$, —NC(O)R$^6$, —NCO$_2$R$^6$, —C(O)R$^7$, —CN, —NO$_2$, —NH$_2$, halogen, trihalomethyl, and —R$^7$; or R$^4$ and R$^5$, when taken together, form a five or six-membered aromatic ring system containing between zero and two nitrogens, said five or six-membered aromatic ring system optionally substituted with between zero and four of R$^{15}$;

R$^6$ is selected from —H, optionally substituted C$_{1-8}$alkyl, optionally substituted arylC$_{1-8}$alkyl, optionally substituted heterocyclylC$_{1-8}$alkyl, optionally substituted aryl, and optionally substituted heterocyclyl;

R$^7$ is selected from —H, optionally substituted C$_{1-8}$alkyl, optionally substituted arylC$_{1-8}$alkyl, optionally substituted heterocyclylC$_{1-8}$alkyl, optionally substituted aryl, and optionally substituted heterocyclyl; provided that there are at least two carbons between any heteroatom of R$^7$ and A or either nitrogen to which R$^2$ or R$^3$ are attached; or R$^6$ and R$^7$, when taken together with a common nitrogen to which they are attached, form an optionally substituted five- to seven-membered heterocyclic ring, said optionally substituted five- to seven-membered heterocyclic ring optionally containing at least one additional heteroatom selected from nitrogen, oxygen, sulfur, and phosphorus;

R$^8$ is —H, —NO$_2$, —CN, —OR$^6$, and optionally substituted C$_{1-8}$alkyl;

X is selected from one of the following six formulae:

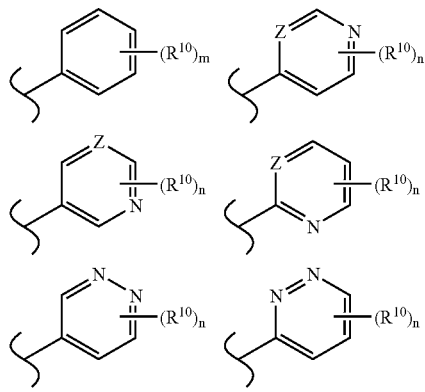

wherein m is zero to five, n is zero to three, and Z is N or CR$^{10}$;

R$^{10}$ is selected from —H, halogen, trihalomethyl, —NH$_2$, —NO$_2$, —OR$^6$, —N=CNR$^6$R$^7$, —NR$^6$R$^7$, —N(R$^6$)C(=NR$^8$)NR$^6$R$^7$, —SR$^6$, —S(O)$_{1-2}$R$^6$, —SO$_2$NR$^6$R$^7$, —CO$_2$R$^6$, —C(O)NR$^6$R$^7$, —C(O)N(OR$^6$)R$^7$, —C(=NR$^8$)NR$^6$R$^7$, —N(R$^6$)SO$_2$R$^6$, —NC(O)R$^6$, —NCO$_2$R$^6$, —C(O)R$^7$, and R$^7$;

K is O, S, or NR$^{11}$;

R$^{11}$ is selected from cyano, —NO$_2$, —OR$^6$, —S(O)$_{1-2}$R$^6$, —SO$_2$NR$^6$R$^7$, —CO$_2$R$^6$, —C(O)NR$^6$R$^7$, —C(O)N(OR$^6$R$^7$, —C(O)R$^7$, and R$^6$; and each R$^{15}$ is independently selected from —H, halogen, —NH$_2$, —NO$_2$, —OR$^6$, —N=CNR$^6$R$^7$, —NR$^6$R$^7$, —N(R$^6$)C(=NR$^8$NR$^6$R$^7$, —SR$^6$, —SR$^6$, —S(O)$_{1-2}$R$^6$, —SO$_2$NR$^6$R$^7$, —CO$_2$R$^6$, —C(O)NR$^6$R$^7$, —C(O)N(OR$^6$)R$^7$, —C(=NR$^8$)NR$^6$R$^7$, —N(R$^6$)SO$_2$R$^6$, —NC(O)R$^6$, —NCO$_2$R$^6$, —C(O)R$^6$, —C(O)R$^7$, and R$^7$.

Embodiment [0022]: In one example, the compound is according to Embodiment [0021], wherein L is NR$^3$.

Embodiment [0023]: In another example, the compound is according to Embodiment [0022], wherein K is either O or NR$^{11}$.

Embodiment [0024]: In another example, the compound is according to Embodiment [0023], wherein R$^2$ and R$^3$ are each independently selected from —H and optionally substituted C$_{1-8}$alkyl, wherein substitution on the C$_{1-8}$alkyl of optionally substituted C$_{1-8}$alkyl is selected from —NH$_2$, —NO$_2$, —OR$^6$, —N=CNR$^6$R$^7$, —NR$^6$R$^7$, —N(R$^6$)C(=NR$^8$)NR$^6$R$^7$, —SR$^6$, —S(O)$_{1-2}$R$^6$, —SO$_2$NR$^6$R$^7$, —CO$_2$R$^6$, —C(O)NR$^6$R$^7$, —C(O)N(OR$^6$)R$^7$, —C(=NR$^8$)NR$^6$R$^7$, —N(R$^6$)SO$_2$R$^6$, —NC(O)R$^6$, —NCO$_2$R$^6$, —C(O)R$^7$, heterocyclic, alicyclic, and aryl.

Embodiment [0025]: In another example, the compound is according to Embodiment [0024], wherein R$^2$ and R$^3$ are —H.

Embodiment [0026]: In another example, the compound is according to Embodiment [0025], wherein only one of R$^1$ is —A—R$^7$, where A is selected from O, S(O)$_{0-1}$, and NR$^6$; and for —A—R$^7$, R$^7$ is an optionally substituted heteroalicyclic ring.

Embodiment [0027]: In another example, the compound is according to Embodiment [0026], wherein R$^6$ is selected from —H and C$_{1-8}$alkyl, said C$_{1-8}$alkyl optionally substituted with one or more groups each independently selected from —NH$_2$, —NO$_2$, —OR$^6$, —N=CNR$^6$R$^7$, —NR$^6$R$^7$, —N(R$^6$)C(=NR$^8$)NR$^6$R$^7$, —SR$^6$, —S(O)$_{1-2}$R$^6$, —SO$_2$NR$^6$R$^7$, —CO$_2$R$^6$, —C(O)NR$^6$R$^7$, —C(O)N(OR$^6$)R$^7$, —C(=NR$^8$)NR$^6$R$^7$, —N(R$^6$)SO$_2$R$^6$, —NC(O)R$^6$, —NCO$_2$R$^6$, —C(O)R$^7$, heterocyclic, alicyclic, and aryl; and R$^7$ of —A—R$^7$ is selected from the following optionally substituted heteroalicyclics: azetidine, perhydroazepinyl, piperidinyl, piperazinyl, azabicyclo[3.2.1]octyl, octahydro-cyclopenta[c]pyrrole, 2-oxopiperidinyl, 2-oxopyrrolidinyl, pyrrolidinyl, dihydropyridinyl, tetrahydropyridinyl, quinuclidinyl, tetrahydrofuranyl, tetrahydropyranyl, thiamorpholinyl sulfone, and dioxaphospholanyl.

Embodiment [0028]: In another example, the compound is according to Embodiment [0027], wherein X is

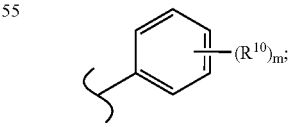

m is 0 to 3, and R$^{10}$ is selected from —H, halogen, —NH$_2$, —NO$_2$, —OR$^6$, —N=CNR$^6$R$^7$, —NR$^6$R$^7$, —N(R$^6$)C(=NR$^8$)NR$^6$R$^7$, —SR$^6$, —S(O)$_{1-2}$R$^6$, —SO$_2$NR$^6$R$^7$, —CO$_2$R$^6$, —C(O)NR$^6$R$^7$, —C(O)N(OR$^6$)R$^7$, —C(=NR$^8$)NR$^6$R$^7$, —N(R$^6$)SO$_2$R$^6$, —NC(O)R$^6$, —NCO$_2$R$^6$, —C(O)R$^7$, and optionally substituted C$_{1-8}$alkyl; said C$_{1-8}$alkyl optionally substituted with one or more groups each independently selected from —$NH_2$, —$NO_2$, $OR^6$, —$N=CNR^6R^7$, —$NR^6R^7$, —$N(R^6)C(=NR^8)NR^6R^7$, —$SR^6$, —$S(O)_{1-2}R^6$, —$SO_2NR^6R^7$, —$CO_2R^6$, —$C(O)NR^6R^7$, —$C(O)N(OR^6)R^7$, —$C(=NR^8)NR^6R^7$, —$N(R^6)SO_2R^6$, —$NC(O)R^6$, —$NCO_2R^6$, —$C(O)R^7$, heterocyclic, alicyclic, and aryl.

Embodiment [0029]: In another example, the compound is according to embodiment [0028], of formula II:

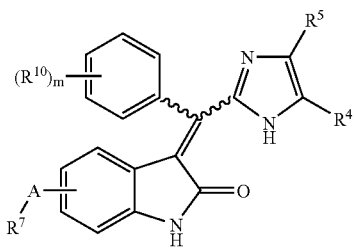

wherein:

A, $R^4$, $R^5$, $R^{10}$, and m are as defined above;

$R^7$ is selected from optionally substituted perhydroazepinyl, optionally substituted piperidinyl, optionally substituted pyrrolidinyl, and optionally substituted azetidine;

wherein the ring nitrogen of $R^7$ is substituted with a group $R^{12}$; and $R^{12}$ is selected from —H, optionally substituted $C_{1-8}$alkyl, —$SO_2R^6$, —$SO_2NR^6R^7$, —$CO_2R^6$, —$C(O)NR^6R^7$, —$C(O)R^7$, and an optionally substituted three- or four-carbon bridge between the ring nitrogen of $R^7$ and a carbon vicinal to the ring nitrogen of $R^7$; said three- or four-atom bridge optionally containing an oxygen in substitution for a carbon of the bridge.

Embodiment [0030]: In another example, the compound is according to Embodiment [0029], wherein —A—$R^7$ selected from the following formulae:

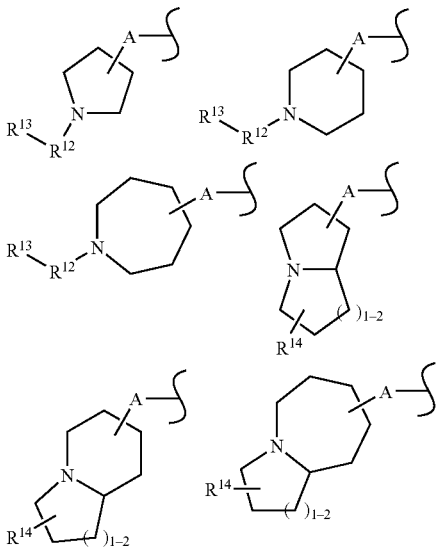

wherein $R^{12}$ is a $C_{1-4}$alkyl; $R^{13}$ is selected from —H, an optionally substituted alkoxy group, an optionally substituted amino group, and an optionally substituted heteroalicyclic, with the proviso that a heteroatom of said optionally substituted alkoxy group, said optionally substituted amino group, or said optionally substituted heteroalicyclic cannot be attached to a carbon of $R^{12}$ which is directly attached to the ring nitrogen of $R^7$; and $R^{14}$ is selected from —H, halogen, —$NH_2$, —$NO_2$, —$OR^6$, —$N=CNR^6R^7$, —$NR^6R^7$, —$N(R^6)C(=NR^8)NR^6R^7$, —$S(O)_{0-2}R^6$, —$SO_2NR^6R^7$, —$CO_2R^6$, —$C(O)N(OR^6)R^7$, —$C(=NR^8)NR^6R^7$, —$N(R^6)SO_2R^6$, —$NC(O)R^6$, —$NCO_2R^6$, —$C(O)R^7$, and optionally substituted $C_{1-6}$alkyl.

Embodiment [0031]: In another example, the compound is according to Embodiment [0030], wherein A is —$NR^6$— where $R^6$ is selected from —H and $C_{1-8}$alkyl, said $C_{1-8}$alkyl substituted with at least one of —$CO_2H$ and —$CO_2C_{1-8}$alkyl.

Embodiment [0032]: In another example, the compound is according to Embodiment [0031], of formula III.

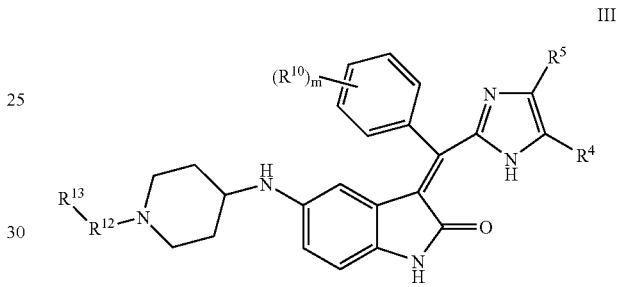

Embodiment [0033]: In another example, the compound is according to Embodiment [0032], wherein $R^{12}$ is a $C_{2-4}$alkyl; $R^{13}$ is as defined above; $R^{10}$ is selected from —H, halogen, perfluoroalkyl, —$NH_2$, —$NO_2$, —$OR^6$, —$N=CNR^6R^7$, —$NR^6R^7$, —$N(R^6)C(=NR^8)NR^6R^7$, —$SR^6$, —$S(O)_{1-2}R^6$, —$SO_2NR^6R^7$, —$CO_2R^6$, —$C(O)NR^6R^7$, —$C(O)N(OR^6)R^7$, —$C(=NR^8)NR^6R^7$, —$N(R^6)SO_2R^6$, —$NC(O)R^6$, —$NCO_2R^6$, —$C(O)R^7$; $R^4$ and $R^5$ are each independently selected from —H, halogen, and $C_{1-4}$alkyl; or $R^4$ and $R^5$ combined are an optionally substituted phenyl; and m is 0-3.

Embodiment [0034]: In another example, the compound is according to Embodiment [0033], wherein $R^{12}$ is an ethylene; $R^{10}$ is halogen; $R^4$ and $R^5$ are each independently selected from —H, halogen, and $C_{1-2}$alkyl; and m is 1-3.

Embodiment [0035]: In another example, the compound is according to Embodiment [0034], wherein each $R^{10}$ is independently selected from fluorine and chlorine; $R^4$ and $R^5$ are each independently selected from —H and $C_{1-2}$alkyl; and m is 1-3.

Embodiment [0036]: In another example, the compound is according to Embodiment [0035], wherein each $R^{10}$ is independently selected from fluorine and chlorine; $R^4$ and $R^5$ are each independently selected from —H and —$CH_3$; and m is 1-2.

Embodiment [0037]: In another example, the compound is according to Embodiment [0036], wherein $R^{10}$ is fluorine; $R^4$ and $R^5$ are each independently selected from —H and —$CH_3$; and m is 1.

Embodiment [0038]: In another example, the compound is according to Embodiment [0021], selected from Table 1:

TABLE 1

| Entry | Name | Structure |
|---|---|---|
| 1 | (3Z)-3-[[5-(methyloxy)-1H-benzimidazol-2-yl](phenyl)methylidene[-5-}[1-(phenylmethyl)pyrrolidin-3-yl]amino}-1,3-dihydro-2H-indol-2-one | 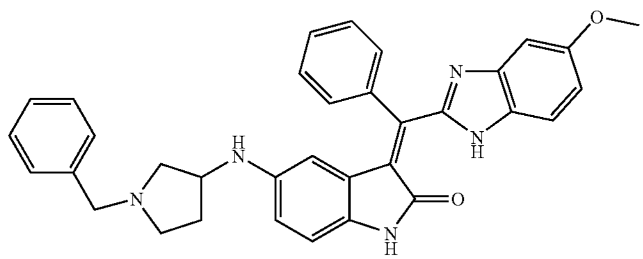 |
| 2 | (3Z)-5-[(1-ethylpiperidin-3-yl)amino]-3-[[5-(methyloxy)-1H-benzimidazol-2-yl](phenyl)methylidene]-1,3-dihydro-2H-indol-2-one | 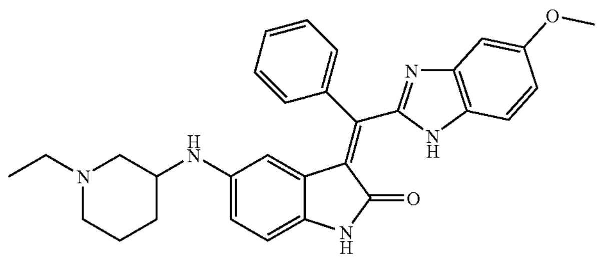 |
| 3 | (3Z)-5-[(1-ethylpiperidin-4-yl)amino]-3-[[5-(methyloxy)-1H-benzimidazol-2-yl](phenyl)methylidene]-1,3-dihydro-2H-indol-2-one | 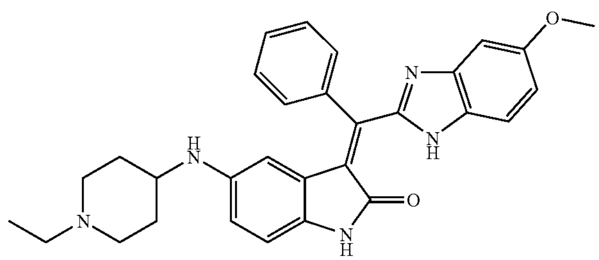 |
| 4 | (3Z)-5-[(1-ethylpiperidin-4-yl)amino]-3-[1H-imidazol-2-yl(phenyl)methylidene}-1,3-dihydro-2H-indol-2-one | 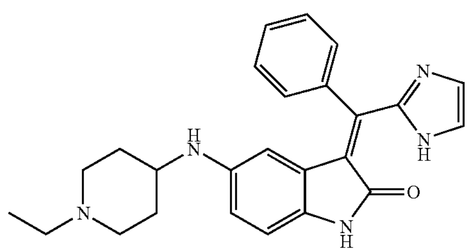 |
| 5 | (3Z)-5-[(1-ethylpiperidin-4-yl)amino]-3-{[5-(methyloxy)-1H-benzimidazol-2-yl][4-(methyloxy)phenyl]methylidene}-1,3-dihydro-2H-indol-2-one | 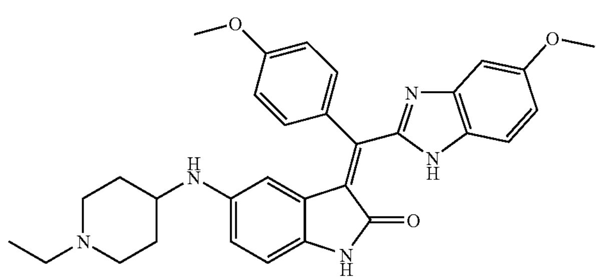 |
| 6 | (3Z)-5-[(1-ethylpiperidin-4-yl)amino]-3-[[5-(methyloxy)-1 H-benzimidazol-2-yl](4-methylphenyl)methylidene]-1,3-dihydro-2H-indol-2-one | 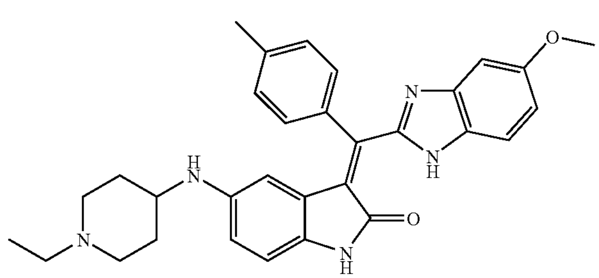 |

TABLE 1-continued

| Entry | Name | Structure |
|---|---|---|
| 7 | (3Z)-3-(1H-benzimidazol-2-yl(4-nitrophenyl)methylidene]-5-[(1-ethylpiperidin-4-yl)amino]-1,3-dihydro-2H-indol-2-one | 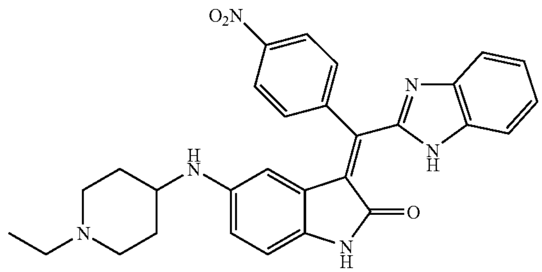 |
| 8 | (3Z)-3-{1H-benzimidazol-2-yl[4-(methyloxy)phenyl]methylidene}-5-[(1-ethylpiperidin-4-yl)amino]-1,3-dihydro-2H-indol-2-one | 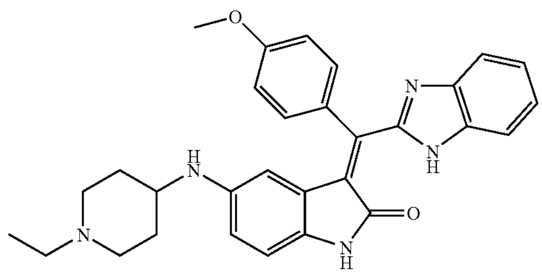 |
| 9 | (3Z)-3-[1H-benzimidazol-2-yl(phenyl)methylidene]-5-[(1-ethylpiperidin-4-yl)amino]-1,3-dihydro-2H-indol-2-one | 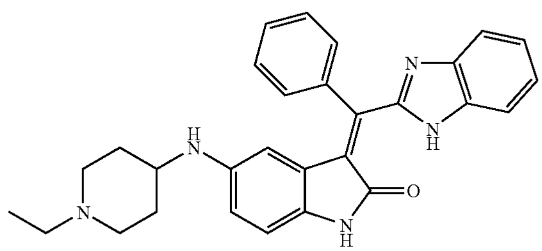 |
| 10 | (3Z)-3-[[5-(methyloxy)-1H-benzimidazol-2-yl](phenyl)methylidene]-5-[(2,2,6,6-tetramethylpiperidin-4-yl)amino]-1,3-dihydro-2H-indol-2-one | 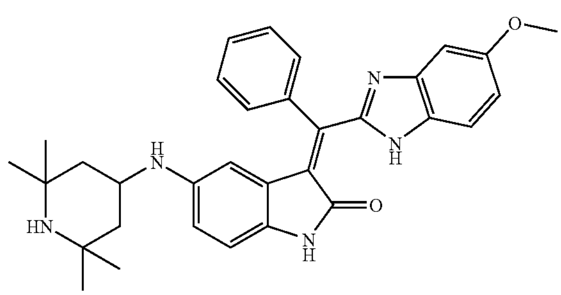 |
| 11 | (3Z)-3-[(4-aminophenyl)(1H-benzimidazol-2-yl)methylidene]-5-[(1-ethylpiperidin-4-yl)amino]1,3-dihydro-2H-indol-2-one | 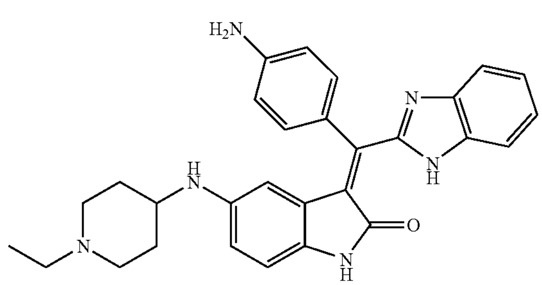 |

TABLE 1-continued

| Entry | Name | Structure |
|---|---|---|
| 12 | (3Z)-3-[1H-benzimidazol-2-yl(4-methylphenyl)methylidene]-5-[(1-ethylpiperidin-4-yl)amino]1,3-dihydro-2H-indol-2-one | 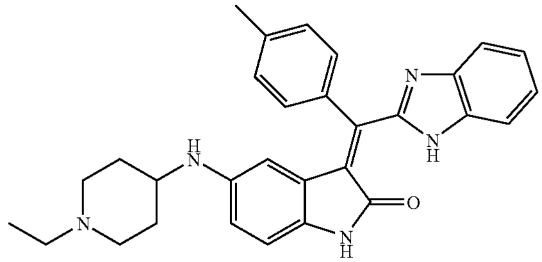 |
| 13 | (3Z)-5-[(1-ethylpiperidin-4-yl)amino]-3-[1H-imidazol-2-yl(4-methylphenyl)methylidene]-1,3-dihydro-2H-indol-2-one | 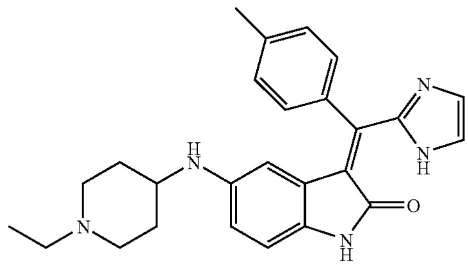 |
| 14 | (3Z)-5-[(1-ethytpiperidin-4-yl)oxy]-3-[[5-(methyloxy)-1H-benzimidazol-2-yl](phenyl)methylidene]-1,3-dihydro-2H-indol-2-one | 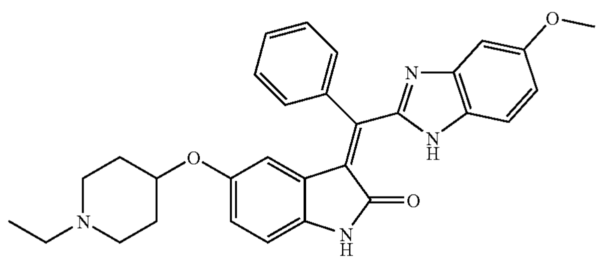 |
| 15 | (3Z)-5-[(1-ethylpiperidin-4-yl)amino]-3-{1H-imidazol-2-yl[4-(methyloxy)phenyl]methylidene}-1,3-dihydro-2H-indol-2-one | 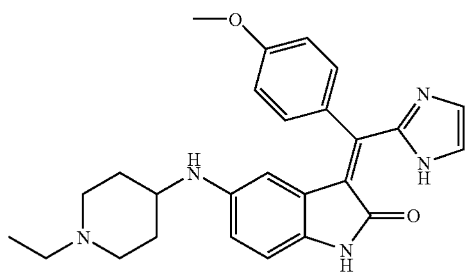 |
| 16 | (3Z)-3-[1H-benzimidazol-2-yl(4-fluorophenyl)methylidene]-5[(1-ethylpiperidin-4-yl)amino]-1,3-dihydro-2H-indol-2-one | 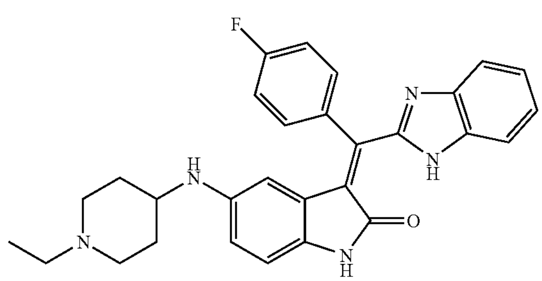 |

TABLE 1-continued

| Entry | Name | Structure |
|---|---|---|
| 17 | (3Z)-3-[1H-benzimidazol-2-yl(3,5-difluorophenyl)methylidene]-5-[(1-ethylpiperidin-4-yl)amino]-1,3-dihydro-2H-indol-2-one | 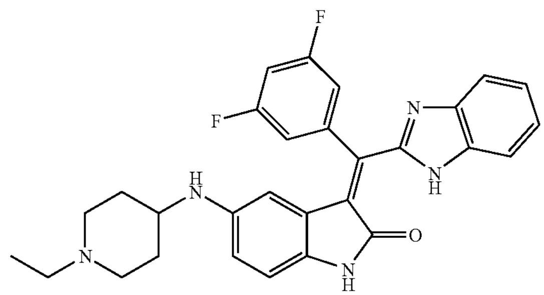 |
| 18 | (3Z)-3-[1H-benzimidazol-2-yl(3-fluorophenyl)methylidene]-5-[(1-ethylpiperidin-4-yl)amino]-1,3-dihydro-2H-indol-2-one | 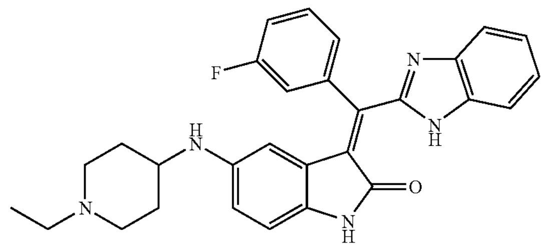 |
| 19 | (3Z)-3-[1H-benzimidazol-2-yl(3-nitrophenyl)methylidene]-5-[(1-ethylpiperidin-4-yl)amino]-1,3-dihydro-2H-indol-2-one | 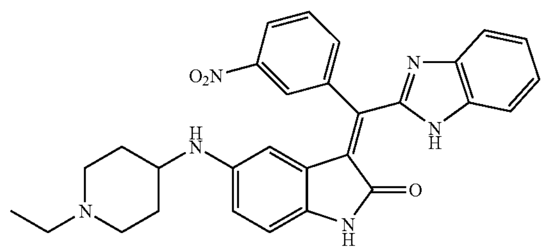 |
| 20 | 3-((Z)-1H-benzimidazol-2-yl{5-[(1-ethylpiperidin-4-yl)amino]-2-oxo-1,2-dihydro-3H-indol-3-ylidene}methyl)benzonitrile | 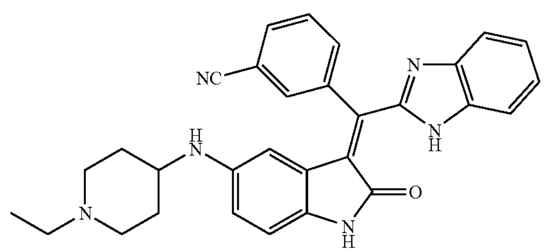 |
| 21 | (3Z)-3-[(3-aminophenyl)(1H-benzimidazol-2-yl)methylidene]-5-[(1-ethylpiperidin-4-yl)amino]-1,3-dihydro-2H-indol-2-one | 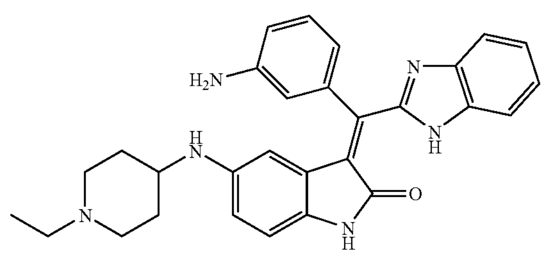 |
| 22 | (3Z)-3-[1H-benzimidazol-2-yl(phenyl)methylidene]-5-(piperidin-4-ylamino)-1,3-dihydro-2H-indol-2-one | 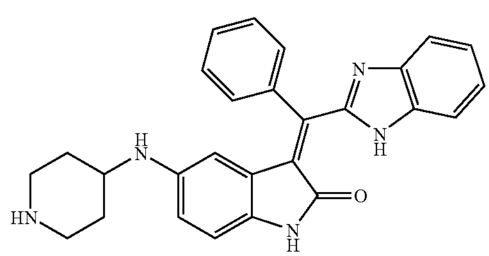 |

TABLE 1-continued

| Entry | Name | Structure |
|---|---|---|
| 23 | 3-((Z)-1H-benzimidazol-2-yl{5-[(1-ethylpiperidin-4-yl)amino]-2-oxo-1,2-dihydro-3H-indol-3-ylidene}methyl)benzenecarboximidamide | 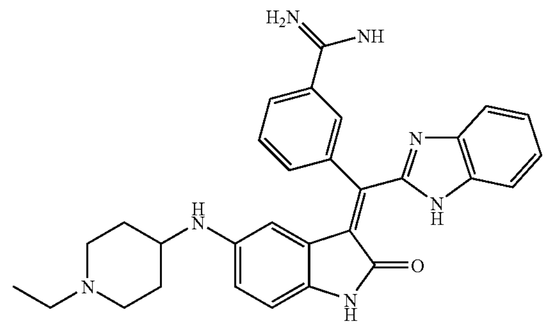 |
| 24 | (3Z)-3-[1H-benzimidazol-2-yl(phenyl)methylidene]-5-({1-[2-(methyloxy)ethyl]piperidin-4-yl}amino)-1,3-dihydro-2H-indol-2-one | 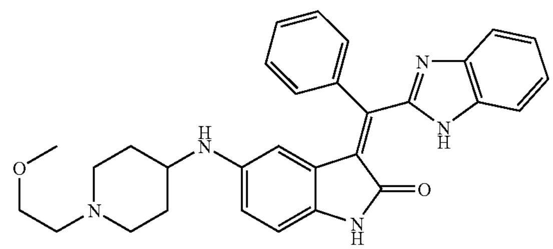 |
| 25 | (3Z)-3-[1H-benzimidazol-2-yl(phenyl)methylidene]-5-[(2,2,6,6-tetramethylpiperidin-4-yl)amino]-1,3-dihydro-2H-indol-2-one | 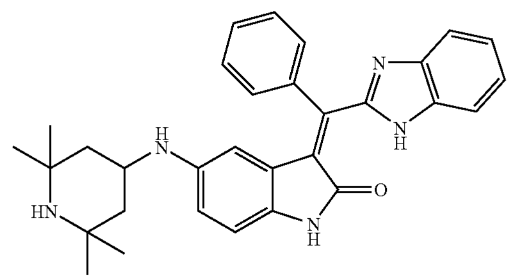 |
| 26 | (3Z)-3-{1H-benzimidazol-2-yl [3-(methyloxy)phenyl]methylidene}-5-[(1-ethylpiperidin-4-yl)amino]-1,3-dihydro-2H-indol-2-one | 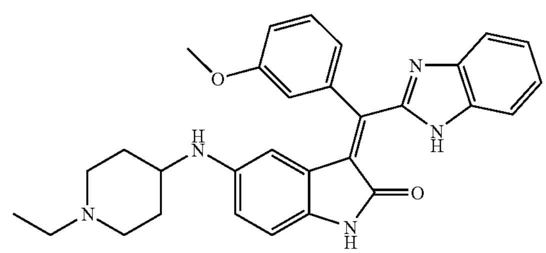 |
| 27 | (3Z)-3-[1H-benzimidazol-2-yl(3-chlorophenyl)methylidene]-5-[(1-ethylpiperidin-4-yl)amino]-1,3-dihydro-2H-indol-2-one | 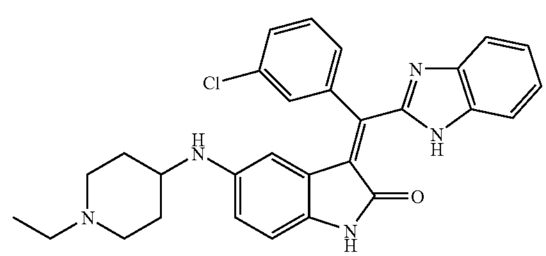 |

TABLE 1-continued

| Entry | Name |
|---|---|
| 28 | 2-(2-{2-[(Z)-{5-[(1-ethylpiperidin-4-yl)amino]-2-oxo-1,2-dihydro-3H-indol-3-ylidene}(phenyl)methyl]-1H-imidazol-4-yl}ethyl)-1H-isoindole-1,3(2H)-dione |
| 29 | (3Z)-3-[1H-benzimidazol-2-yl(phenyl)methylidene]-5-({1-[2-(dimethylamino)ethyl]piperidin-4-yl}amino)-1,3-dihydro-2H-indol-2-one |
| 30 | (3Z)-3-[1H-benzimidazol-2-yl(phenyl)methylidene]-5-{[1-(methylsulfonyl)piperidin-4-yl]amino}-1,3-dihydro-2H-indol-2-one |
| 31 | (3Z)-5-(8-azabicyclo[3.2.1]oct-3-ylamino)-3-[1H-benzimidazol-2-yl(phenyl)methylidene]-1,3-dihydro-2H-indol-2-one |
| 32 | (3Z)-3-{1H-benzimidazol-2-yl[3-(methyloxy)phenyl]methylidene}-5-[(1-ethylpiperidin-4-yl)oxy]-1,3-dihydro-2H-indol-2-one |
| 33 | (3Z)-3-[1H-benzimidazol-2-yl(3,5-difluorophenyl)methylidene]-5-[(1-ethylpiperidin-4-yl)oxy]-1,3-dihydro-2H-indol-2-one |

TABLE 1-continued

| Entry | Name | Structure |
|---|---|---|
| 34 | (3Z)-3-[1H-benzimidazol-2-yl(phenyl)methylidene]-5-{(1-(phenylmethyl)piperidin-4-yl]oxy}-1,3-dihydro-2H-indol-2-one | 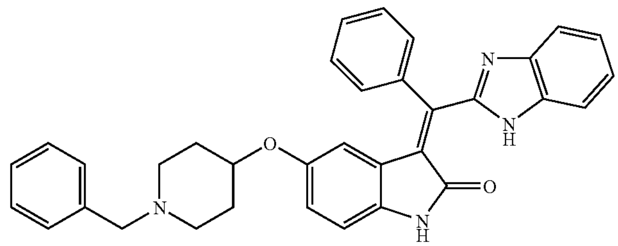 |
| 35 | (3Z)-3-[1H-benzimidazol-2-yl(3-chlorophenyl)methylidene]-5-[(1-ethylpiperidin-4-yl)oxy]-1,3-dihydro-2H-indol-2-one | 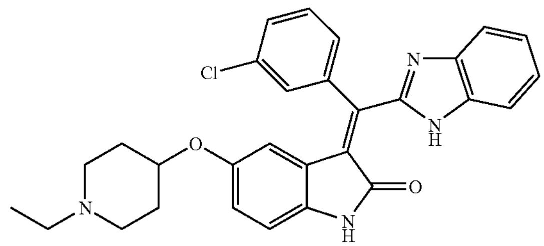 |
| 36 | (3Z)-3-[1H-benzimidazol-2-yl(3,5-difluorophenyl)methylidene]-5-({1-[2-(methyloxy)ethyl]piperidin-4-yl}oxy)-1,3-dihydro-2H-indol-2-one | 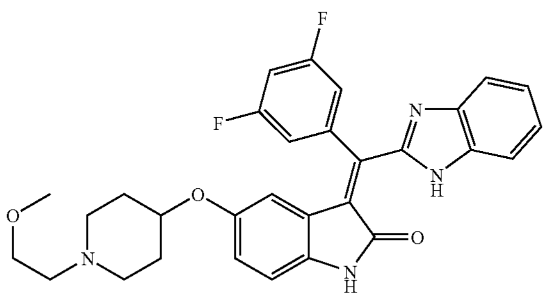 |
| 37 | (3Z)-3-[1H-benzimidazol-2-yl(3-chlorophenyl)methylidene]-5-({1-[2-(methyloxy)ethyl]piperidin-4-yl)oxy)-1,3-dihydro-2H-indol-2-one | 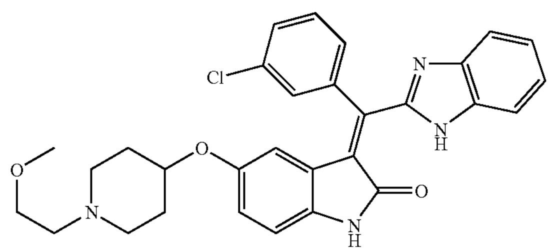 |
| 38 | (3Z)-3-[1H-benzimidazol-2-yl(3-chlorophenyl)methylidene]-5-({1-[2-(methyloxy)ethyl]piperidin-4-yl}amino)-1,3-dihydro-2H-indol-2-one | 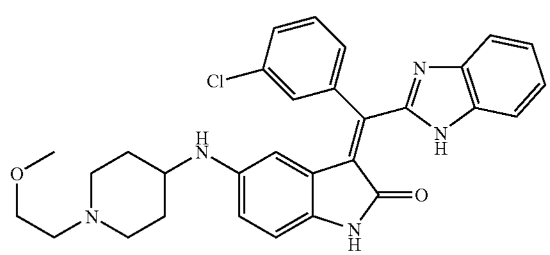 |
| 39 | (3Z)-3-{1H-benzimidazol-2-yl[3-(methyloxy)phenyl]methylidene}-5-({1-[2-(methyloxy)ethyl]piperidin-4-yl}amino)-1,3-dihydro-2H-indol-2-one | 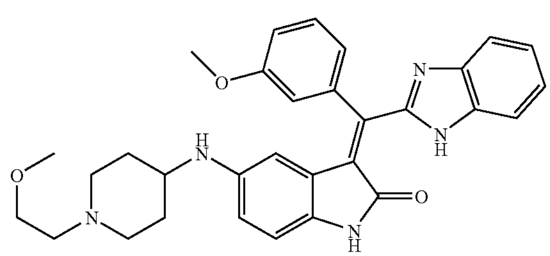 |

TABLE 1-continued

| Entry | Name | Structure |
|---|---|---|
| 40 | (3Z)-3-[(3-chlorophenyl)(1H-imidazol-2-yl)methylidene]-5-({1-[2-(methyloxy)ethyl]piperidin-4-yl}amino)-1,3-dihydro-2H-indol-2-one | 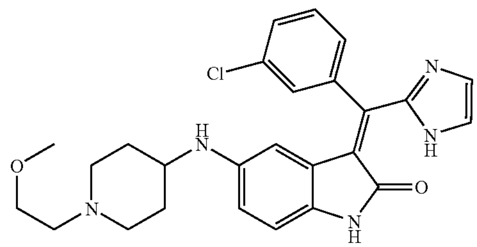 |
| 41 | (3Z)-3-[(3-fluorophenyl)(1H-imidazol-2-yl)methylidene]-5-({1-[2-(methyloxy)ethyl]piperidin-4-yl}amino)-1,3-dihydro-2H-indol-2-one | 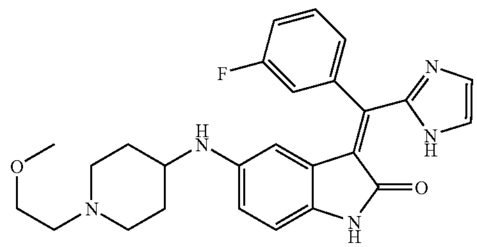 |
| 42 | (3Z)-3-[[1H-benzimidazol-2-yl(3,5-difluorophenyl)methylidene]-5-({1-[2-(methyloxy)ethyl]piperidin-4-yl}amino)-1,3-dihydro-2H-indol-2-one | 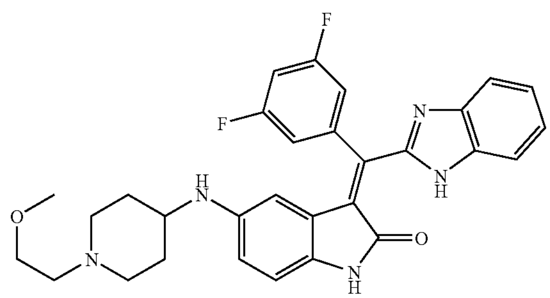 |
| 43 | (3Z)-3-[[1H-benzimidazol-2-yl(3-chlorophenyl)methylidene]-5-[(1-ethylpiperidin-4-yl)(methyl)amino]-1,3-dihydro-2H-indol-2-one | 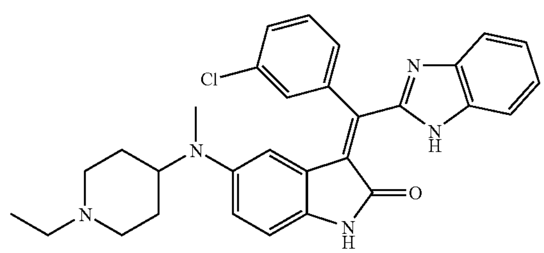 |
| 44 | (3Z)-3-[(3-chlorophenyl)(1H-imidazol-2-yl)methylidene]-5-[(1-ethylpiperidin-4-yl)oxy]-1,3-dihydro-2H-indol-2-one | 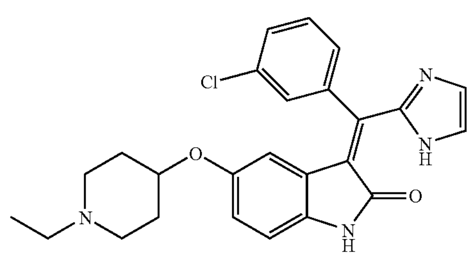 |
| 45 | (3Z)-3-[1H-benzimidazol-2-yl(4-chlorophenyl)methylidene]-5-[(1-ethylpiperidin-4-yl)amino]-1,3-dihydro-2H-indol-2-one | 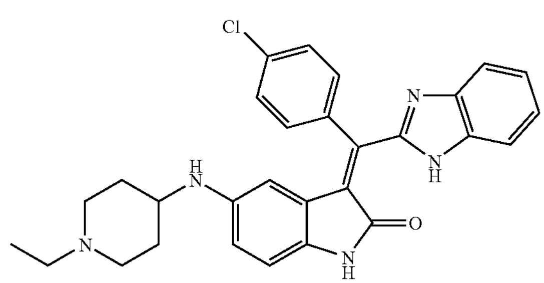 |

TABLE 1-continued

| Entry | Name |
|---|---|
| 46 | (3Z)-3-[1H-benzimidazol-2-yl(3-fluorophenyl)methylidene]-5-({1-[2-(methyloxy)ethyl]piperidin-4-yl}amino)-1,3-dihydro-2H-indol-2-one |
| 47 | (3Z)-3-[1H-benzimidazol-2-yl(4-fluorophenyl)methylidene]-5-({1-[2-(methyloxy)ethyl]piperidin-4-yl}amino)-1,3-dihydro-2H-indol-2-one |
| 48 | (3Z)-3-[(3-chlorophenyl)(1H-imidazol-2-yl)methylidene]-5-[(1-ethylpiperidin-4-yl)amino]-1,3-dihydro-2H-indol-2-one |
| 49 | (3Z)-5-[(1-ethylpiperidin-4-yl)amino]-3-[(3-fluorophenyl)(1H-imidazol-2-yl)methylidene]-1,3-dihydro-2H-indol-2-one |
| 50 | (3Z)-3-[1H-benzimidazol-2-yl(3-fluoro-4-methylphenyl)methylidene]-5-{(1-ethylpiperidin-4-yl)amino]-1,3-dihydro-2H-indol-2-one |
| 51 | (3Z)-5-[(1-ethylpiperidin-4-yl)amino]-3-[(3-fluorophenyl)(4-methyl-1H-imidazol-2-yl)methylidene]-1,3-dihydro-2H-indol-2-one |

TABLE 1-continued

| Entry | Name | Structure |
|---|---|---|
| 52 | (3Z)-3-[1H-benzimidazol-2-yl(4-fluoro-3-methylphenyl)methylidene]-5-{(1-ethylpiperidin-4-yl)amino]-1,3-dihydro-2H-indol-2-one | 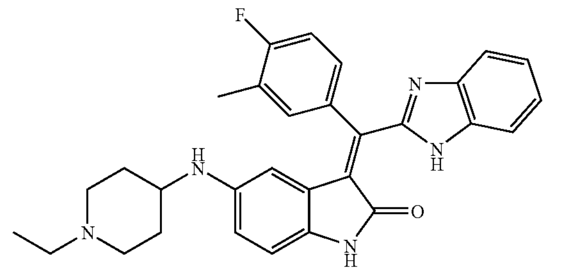 |
| 53 | (3Z)-3-[(3-chloro-4-fluorophenyl)(1H-imidazol-2-yl)methylidene]-5-[(1-ethylpiperidin-4-yl)amino]-1,3-dihydro-2H-indol-2-one | 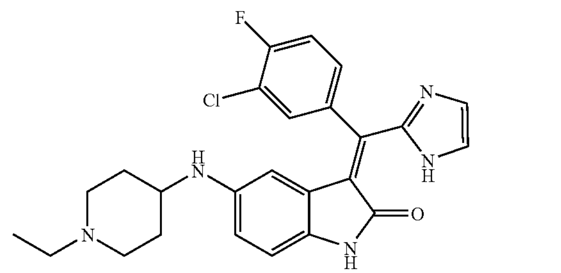 |
| 54 | (3Z)-3-[(3,4-difluorophenyl)(1H-imidazol-2-yl)methylidene]-5-[(1-ethylpiperidin-4-yl)amino]-1,3-dihydro-2H-indol-2-one | 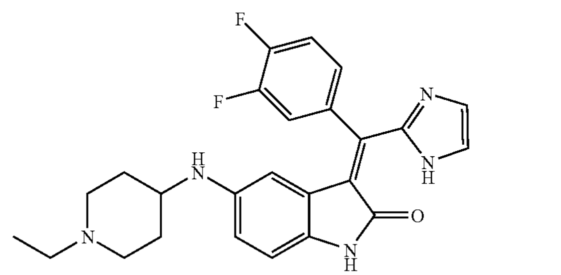 |
| 55 | (3Z)-3-[(5-chloro-1H-benzimidazol-2-yl)(phenyl)methylidene]-5-[(1-ethylpiperidin-4-yl)amino]-1,3-dihydro-2H-indol-2-one | 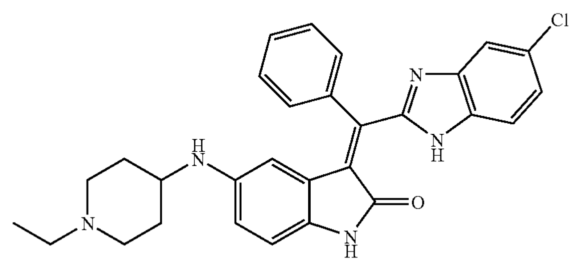 |
| 56 | (3Z)-3-[(5-chloro-1H-benzimidazol-2-yl)(3,5-difluorophenyl)methylidene]-5-[(1-ethylpiperidin-4-yl)amino]-1,3-dihydro-2H-indol-2-one | 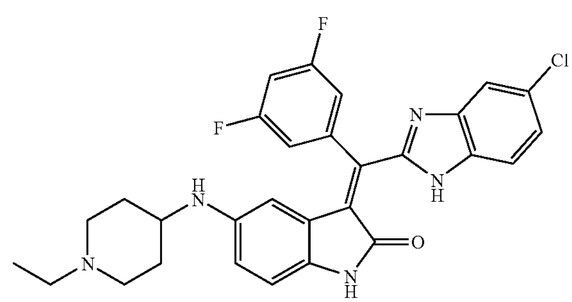 |

TABLE 1-continued

| Entry | Name | Structure |
|---|---|---|
| 57 | (3Z)-5-[(1-ethylpiperidin-4-yl)amino]-3-[(3-fluoro-4-methylphenyl)(1H-imidazol-2-yl)methylidene]-1,3-dihydro-2H-indol-2-one | 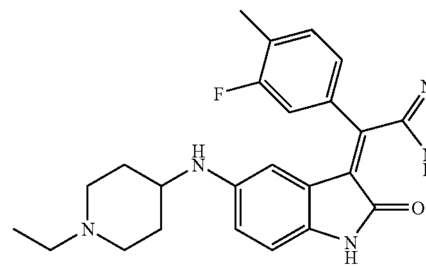 |
| 58 | (3Z)-5-[(1-ethylpiperidin-4-yl)amino]-3-[(4-fluorophenyl)(1H-imidazol-2-yl)methylidene]-1,3-dihydro-2H-indol-2-one | 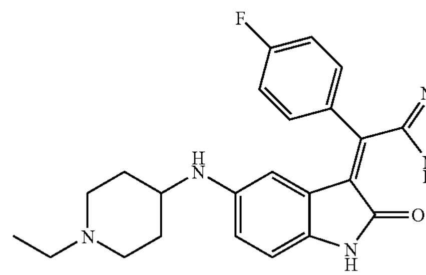 |
| 59 | (3Z)-5-[(1-ethylpiperidin-4-yl)amino]-3-[1H-imidazol-2-yl(4-propylphenyl)methylidene]-1,3-dihydro-2H-indol-2-one | 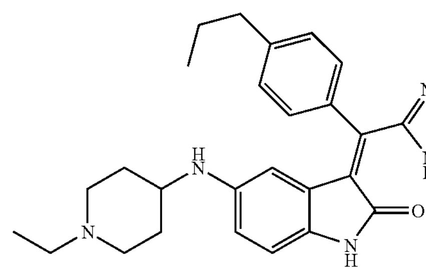 |
| 60 | (3Z)-5-[(1-ethylpiperidin-4-yl)amino]-3-{1H-imidazol-2-yl[4-(trifluoromethyl)phenyl]methylidene}-1,3-dihydro-2H-indol-2-one | 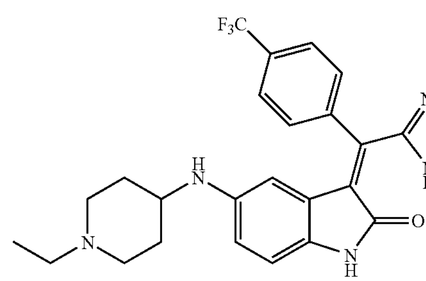 |
| 61 | (3E)-3-[(3,5-difluorophenyl)(5-fluoro-1H-benzimidazol-2-yl)methylidene]-5-[(1-ethylpiperidin-4-yl)amino]-1,3-dihydro-2H-indol-2-one | 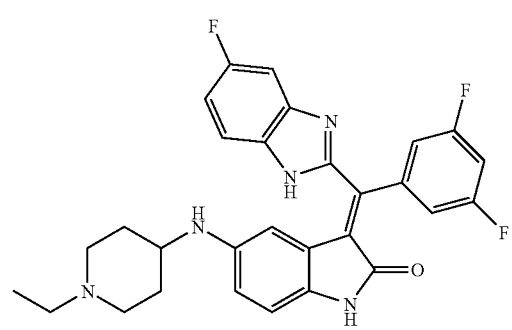 |

TABLE 1-continued

| Entry | Name | Structure |
|---|---|---|
| 62 | (3Z)-3-[(3,5-difluorophenyl)(5-fluoro-1H-benzimidazol-2-yl)methylidene]-5-[(1-ethylpiperidin-4-yl)amino]-1,3-dihydro-2H-indol-2-one | 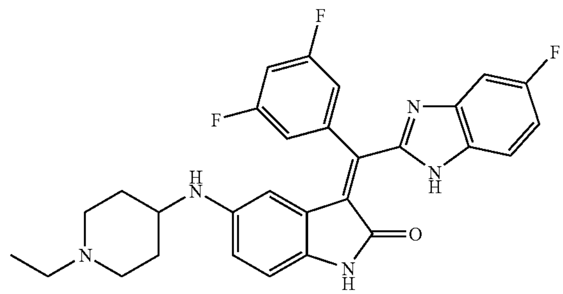 |
| 63 | (3Z)-3-[(3-fluoro-4-methylphenyl)(1H-imidazol-2-yl)methylidene]-5-({1-[2-(methyloxy)ethyl]piperidin-4-yl}amino)-1,3-dihydro-2H-indol-2-one | 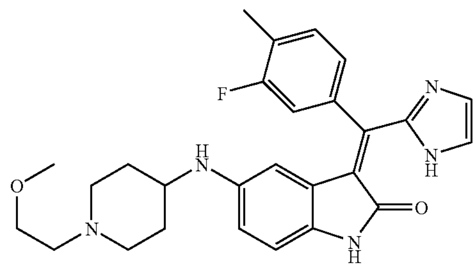 |
| 64 | (3Z)-5-[(1-ethylpiperidin-4-yl)amino]-3-[(4-methyl-1H-imidazol-2-yl)(4-methylphenyl)methylidene] 1,3-dihydro-2H-indol-2-one | 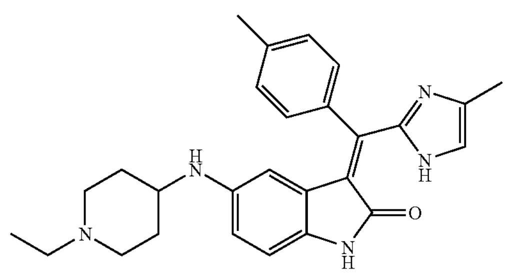 |
| 65 | (3Z)-5-[(1-ethylpiperidin-4-yl)amino]-3-[[3-fluoro-4-(trifluoromethyl)phenyl](1H-imidazol-2-yl)methylidene]-1,3-dihydro-2H-indol-2-one | 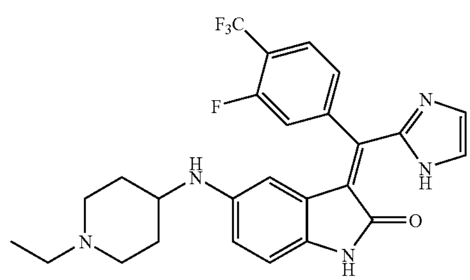 |
| 66 | (3Z)-3-[(4-chlorophenyl)(1H-imidazol-2-yl)methylidene]-5-([(1-ethylpiperidin-4-yl)amino]-1,3-dihydro-2H-indol-2-one | 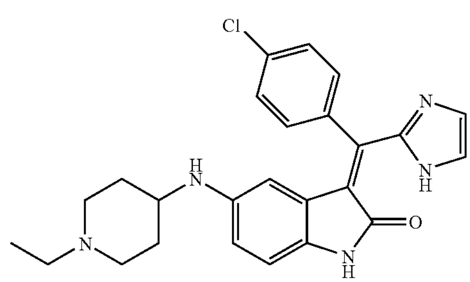 |

TABLE 1-continued

| Entry | Name | Structure |
|---|---|---|
| 67 | (3Z)-5-[(1-ethylpiperidin-4-yl)amino]-3-[(3-fluoro-4-methylphenyl)(4-methyl-1H-imidazol-2-yl)methylidene]-1,3-dihydro-2H-indol-2-one | 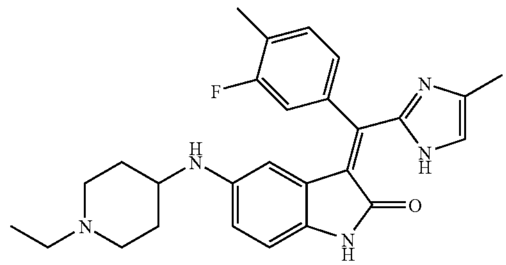 |
| 68 | (3Z)-5-[(1-ethylpiperidin-4-yl)amino]-3-{(1H-imidazol-2-yl[6-(trifluoromethyl)pyridin-3-yl]methylidene}-1,3-dihydro-2H-indol-2-one | 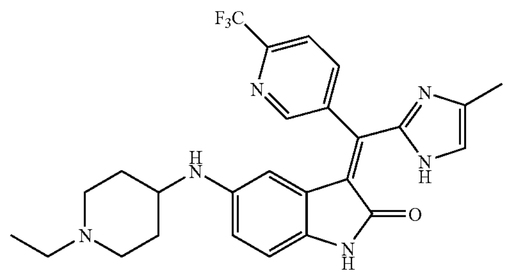 |
| 69 | (3Z)-3-[1H-benzimidazol-2-yl(4-methylphenyl)methylidene]-5-{(1-[2-(methyloxy)ethyl]piperidin-4-yl)amino)-1,3-dihydro-2H-indol-2-one | 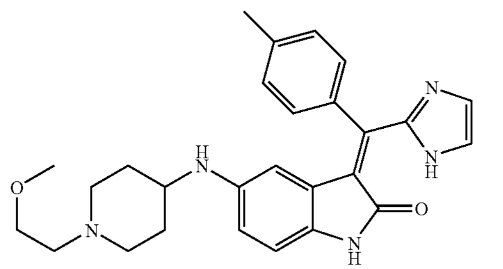 |
| 70 | (3Z)-3-[(3-fluorophenyl)(4-methyl-1H-imidazol-2-yl)methylidene]-5-({1-[2-(methyloxy)ethyl]piperidin-4-yl}amino)-1,3-dihydro-2H-indol-2-one | 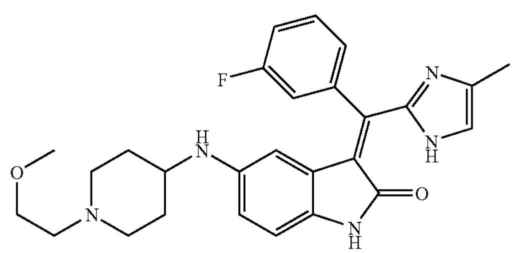 |
| 71 | (3Z)-3-[1H-benzimidazol-2-yl(4-trifluoromethyl)phenyl]methylidene}-5-({1-[2-(methyloxy)ethyl]piperidin-4-yl}amino)-1,3-dihydro-2H-indol-2-one | 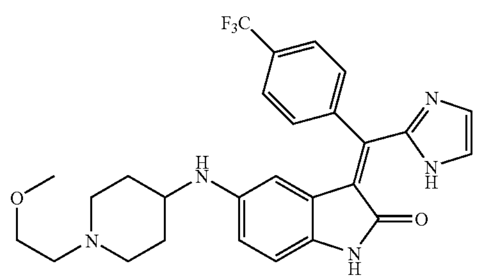 |

TABLE 1-continued

| Entry | Name | Structure |
|---|---|---|
| 72 | (3Z)-3-[(5-chloro-1H-benzimidazol-2-yl)phenyl)methylidene]-5-({1-[2-methyloxy)ethyl]piperidin-4-yl}amino)-1,3-dihydro-2H-indol-2-one | 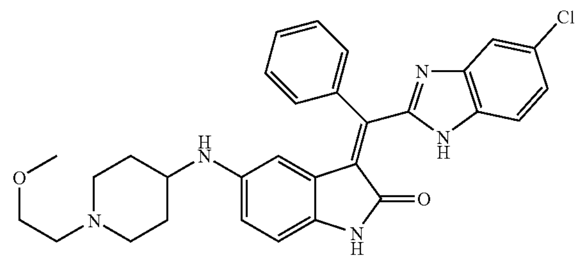 |
| 73 | (3Z)-3-[(3,5-difluorophenyl)(1H-imidazol-2-yl)methylidene]-5-[(1-ethylpiperidin-4-yl)amino]-1,3-dihydro-2H-indol-2-one | 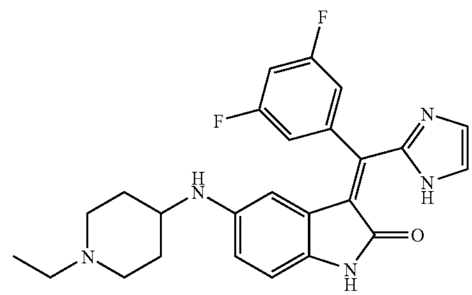 |
| 74 | (3Z)-3-[(3,5-difluorophenyl)(4-methyl-1H-imidazol-2-yl)methylidene]-5-[(1-ethylpiperidin-4-yl)amino]-1,3-dihydro-2H-indol-2-one | 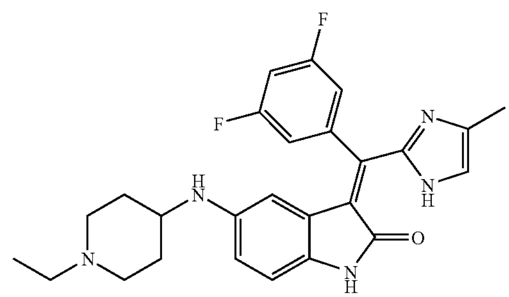 |
| 75 | (3Z)-3-[(3,5-difluorophenyl)(1H-imidazol-2-yl)methylidene]-5-({1-[2-(methyloxy)ethyl]piperidin-4-yl}amino)-1,3-dihydro-2H-indol-2-one | 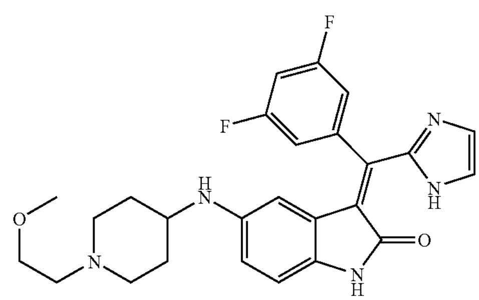 |
| 76 | (3Z)-3-[(3,5-difluorophenyl)(4-methyl-1H-imidazol-2-yl)methylidene]-5-({(1-[2-(methyloxy)ethyl]piperidin-4-yl}amino)-1,3-dihydro-2H-indol-2-one | 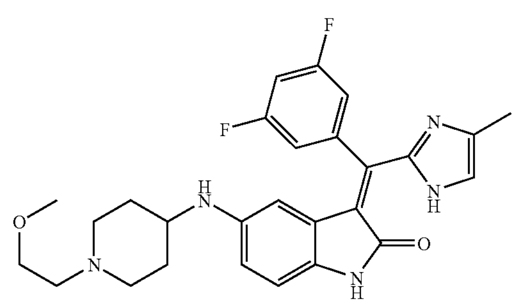 |

TABLE 1-continued

| Entry | Name | Structure |
|---|---|---|
| 77 | (3Z)-3-[(4-methyl-1H-imidazol-2-yl)(4-methylphenyl)methylidene]-5-({1-[2-(methyloxy)ethyl]piperidin-4-yl}amino)-1,3-dihydro-2H-indol-2-one | 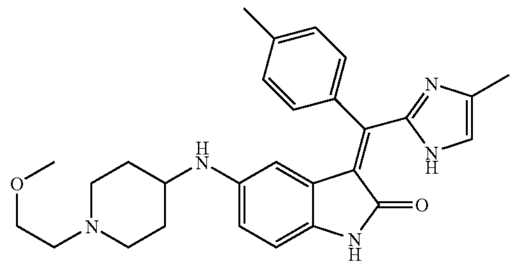 |
| 78 | (3Z)-3-[(4-fluorophenyl)(1H-imidazol-2-yl)methylidene]-5-({(1-[2-(methyloxy)ethyl]piperidin-4-yl}amino)-1,3-dihydro-2H-indol-2-one | 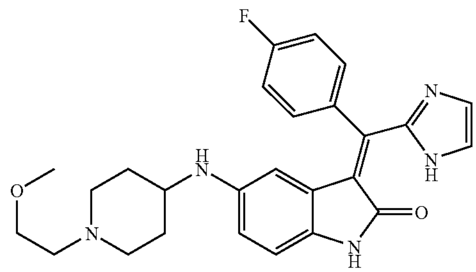 |
| 79 | (3Z)-3-[(3,5-difluorophenyl)(1H-imidazol-2-yl)methylidene]-5-({(1-[2-(methyloxy)ethyl]piperidin-4-yl}amino)-1,3-dihydro-2H-indol-2-one | 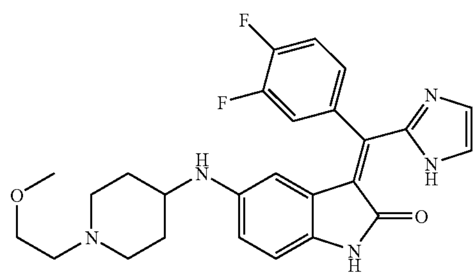 |
| 80 | (3Z)-3-[(3-chloro-4-fluorophenyl)(1H-imidazol-2-yl)methylidene]-5-({(1-[2-(methyloxy)ethyl]piperidin-4-yl}amino)-1,3-dihydro-2H-indol-2-one | 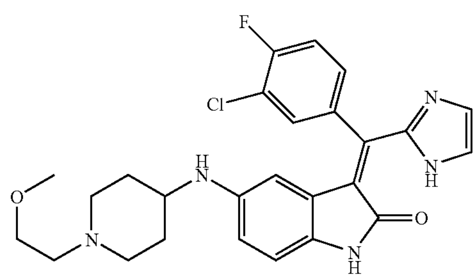 |
| 81 | (3Z)-3-[(3-fluorophenyl)(1H-imidazol-2-yl)methylidene]-5-(piperidin-4-ylamino)-1,3-dihydro-2H-indol-2-one | 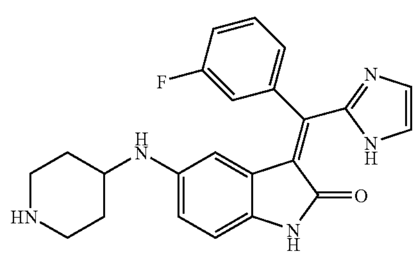 |

TABLE 1-continued

| Entry | Name | Structure |
|---|---|---|
| 82 | (3Z)-3-[(3-fluorophenyl)(1H-imidazol-2-yl)methylidene]-5-({[1-(2-piperidin-1-ylethyl)piperidin-4-yl]amino}-1,3-dihydro-2H-indol-2-one | 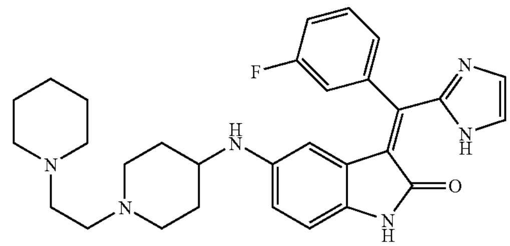 |
| 83 | (3Z)-3-[(3-fluorophenyl)(1H-imidazol-2-yl)methylidene]-5-({[1-(2-morpholin-4-ylethyl)piperidin-4-yl]amino}-1,3-dihydro-2H-indol-2-one | 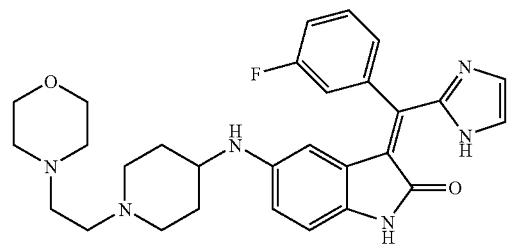 |
| 84 | (3Z)-5-({1-[2-(diethylamino)ethyl]piperidin-4-yl}amino)-3-[(3-fluorophenyl)(1H-imidazol-2-yl)methylidene]-1,3-dihydro-2H-indol-2-one | 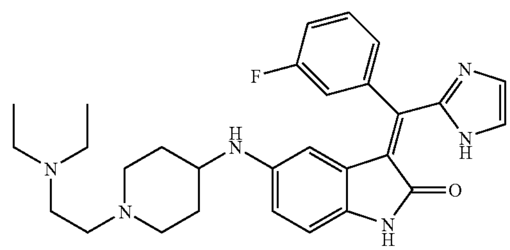 |
| 85 | (3Z)-3-[(3-fluorophenyl)(1H-imidazol-2-yl)methylidene]-5-{[1-(2-pyrrolidin-1-ylethyl)piperidin-4-yl]amino}-1,3-dihydro-2H-indol-2-one | 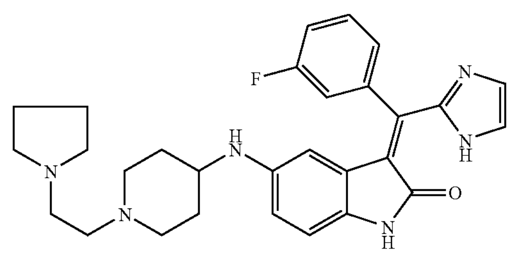 |
| 86 | (3Z)-3-[1H-imidazol-2-yl)(4-methylphenyl)methylidene]-5-[(1-methylpiperidin-4-yl)amino]-1,3-dihydro-2H-indol-2-one | 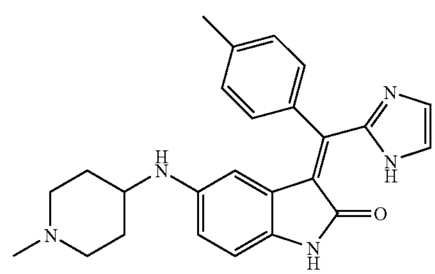 |
| 87 | (3Z)-3-[(3-fluorophenyl)(1H-1,2,4-triazol-5-yl)methylidene]-5-({[1-[2-(methyloxy)ethyl]piperidin-4-yl}amino)-1,3-dihydro-2H-indol-2-one | 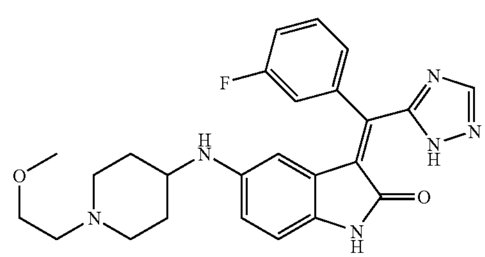 |

TABLE 1-continued

| Entry | Name | Structure |
|---|---|---|
| 88 | ethyl 2-{(Z)-(3-fluorophenyl)[5-({1-[2-(methyloxy)ethyl]piperidin-4-yl}amino)-2-oxo-1,2-dihydro-3H-indol-3-ylidene]methyl}-4-methyl-1H-imidazole-5-carboxylate | 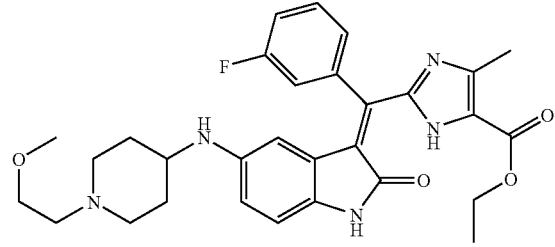 |
| 89 | (3Z)-3-[1H-imidazol-2-yl)(phenyl)methylidene]-5-({1-[2-(methyloxy)ethyl]piperidin-4-yl}amino)-1,3-dihydro-2H-indol-2-one | 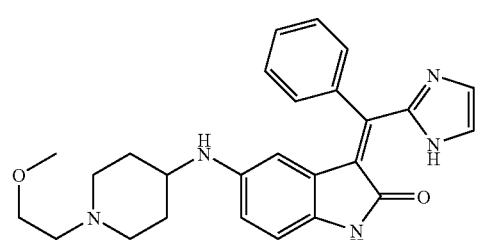 |
| 90 | (3Z)-3-{1H-imidazol-2-yl[4-(methyloxy)phenyl]methylidene}-5-({1-[2-methyloxy)ethyl]piperidin-4-yl}amino)-1,3-dihydro-2H-indol-2-one | 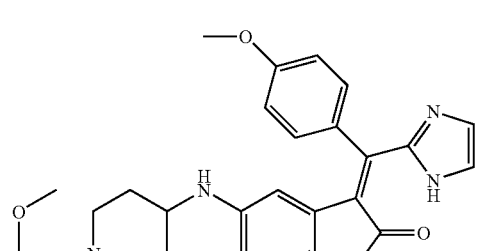 |
| 91 | (3Z)-3-[(4-chlorophenyl)(1H-imidazol-2-yl)methylidene]-5-({1-[2-(methyloxy)ethyl]piperidin-4-yl}amino)-1,3-dihydro-2H-indol-2-one | 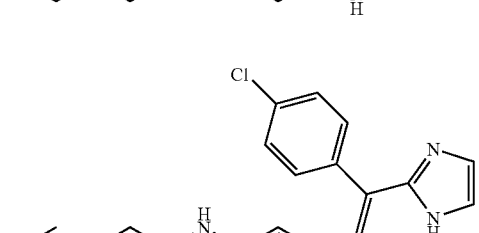 |
| 92 | (3Z)-3-[[3-fluoro-4-(trifluoromethyl)phenyl](1H-imidazol-2-yl)methylidene]-5-({1-[2-(methyloxy)ethyl]piperidin-4-yl}amino)-1,3-dihydro-2H-indol-2-one | 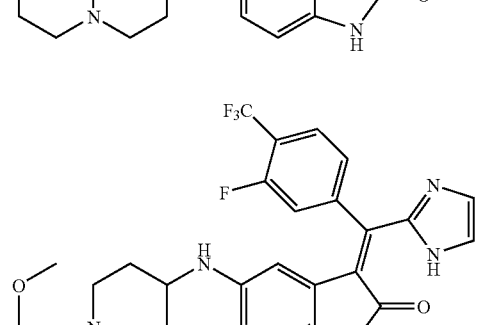 |

TABLE 1-continued

| Entry | Name | Structure |
|---|---|---|
| 93 | (3Z)-3-[(3-fluorophenyl)(1H-imidazol-2-yl)methylidene]-5-{[1-(methylsulfonyl)piperidin-4-yl]amino}-1,3-dihydro-2H-indol-2-one | 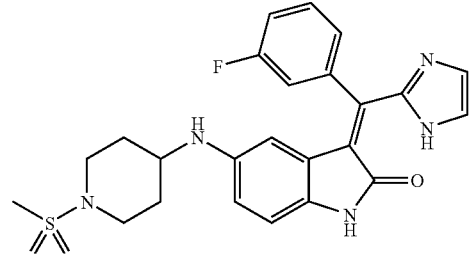 |
| 94 | (3Z)-3-[1H-imidazol-2-yl(4-propylphenyl)methylidene]-5-({1-[2-(methyloxy)ethyl]piperidin-4-yl}amino)-1,3-dihydro-2H-indol-2-one | 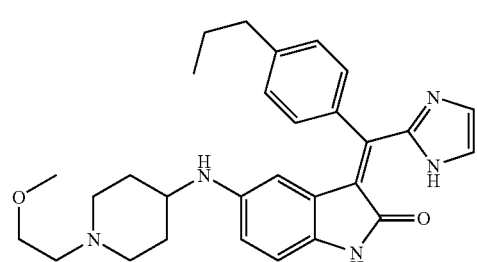 |
| 95 | (3Z)-5-[(1-ethylpiperidin-4-yl)amino]-3-[(3-fluorophenyl)(4-phenyl-1H-imidazol-2-yl)methylidene]-1,3-dihydro-2H-indol-2-one | 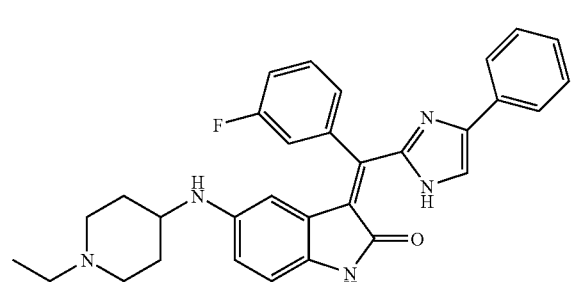 |
| 96 | (3Z)-3-[(3-fluorophenyl)(4-phenyl-1H-imidazol-2-yl)methylidene]-5-({1-[2-(methyloxy)ethyl]piperidin-4-yl}amino)-1,3-dihydro-2H-indol-2-one | 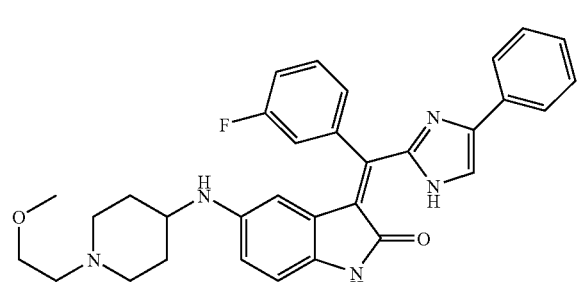 |
| 97 | (3Z)-3-[(3-fluoro-4-methylphenyl)(4-methyl-1H-imidazol-2-yl)methylidene]-5-({1-[2-(methyloxy)ethyl]piperidin-4-yl}amino)-1,3-dihydro-2H-indol-2-one | 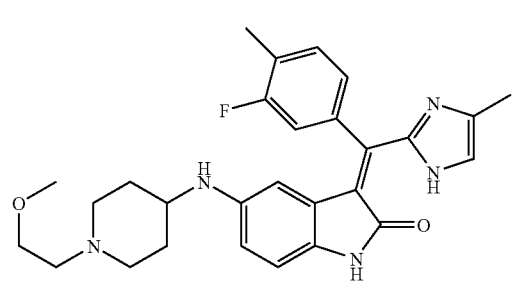 |

TABLE 1-continued

| Entry | Name | Structure |
|---|---|---|
| 98 | (3Z)-3-{1H-imidazol-2-yl[6-(trifluoromethyl)pyridin-3-yl]methylidene}-5-({1-[2-methyloxy)ethyl]piperidin-4-yl}amino)-1,3-dihydro-2H-indol-2-one | 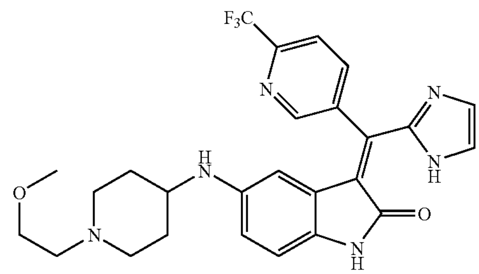 |
| 99 | (3Z)-5-[(1-ethylpiperidin-4-yl)amino]-3-[(3-fluorophenyl)(1H-1,2,4-triazol-5-yl)methylidene]-1,3-dihydro-2H-indol-2-one | 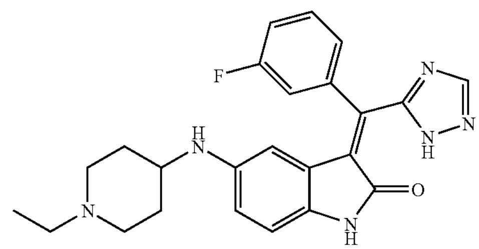 |
| 100 | (3Z)-5-[(1-ethylpiperidin-4-yl)amino]-3-[[2-fluoro-4-(trifluoromethyl)phenyl](1H-imidazol-2-yl)methylidene]-1,3-dihydro-2H-indol-2-one | 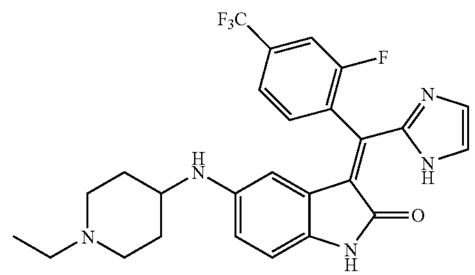 |
| 101 | (3Z)-5-[(1-ethylpiperidin-4-yl)amino]-3-{4-methyl-1H-imidazol-2-yl)[4-(trifluoromethyl)phenyl]methylidene]-1,3-dihydro-2H-indol-2-one | 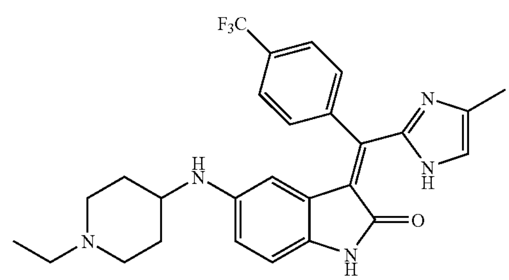 |
| 102 | (3Z)-3-[(4-methyl-1H-imidazol-2-yl)methylidene]-5-[(1-ethylpiperidin-4-yl)amino]-1,3-dihydro-2H-indol-2-one | 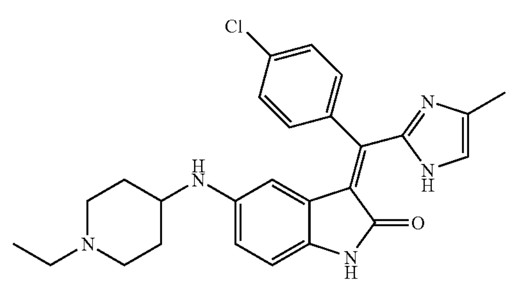 |

TABLE 1-continued

| Entry | Name | Structure |
|---|---|---|
| 103 | (3Z)-5-[(1-ethylpiperidin-4-yl)amino]-3-[[3-fluoro-4-(trifluoromethyl)phenyl](4-methyl-1H-imidazol-2-yl)methylidene]-1,3-dihydro-2H-indol-2-one | 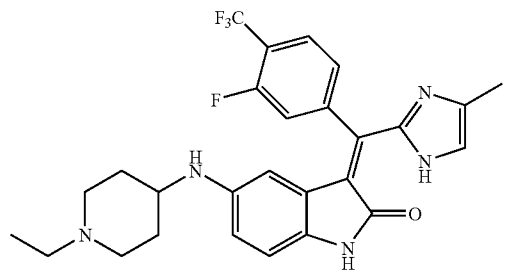 |
| 104 | (3Z)-3-[(3,4-difluorophenyl)(4-methyl-1H-imidazol-2-yl)methylidene]-5-[(1-ethylpiperidin-4-yl)amino]-1,3-dihydro-2H-indol-2-one | 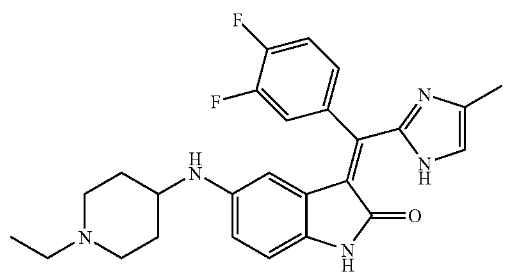 |
| 105 | (3Z)-3-[(3-chloro-4-fluorophenyl)(4-methyl-1H-imidazol-2-yl)methylidene]-5-[(1-ethylpiperidin-4-yl)amino]-1,3-dihydro-2H-indol-2-one | 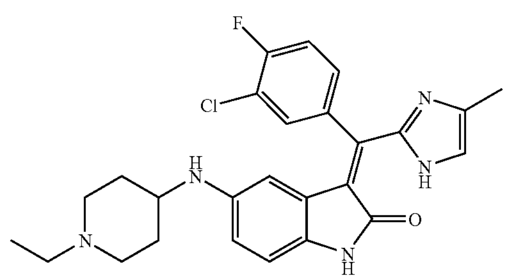 |
| 106 | (3Z)-5-[(1-ethylpiperidin-4-yl)amino]-3-[(4-fluorophenyl)(4-methyl-1H-imidazol-2-yl)methylidene]-1,3-dihydro-2H-indol-2-one | 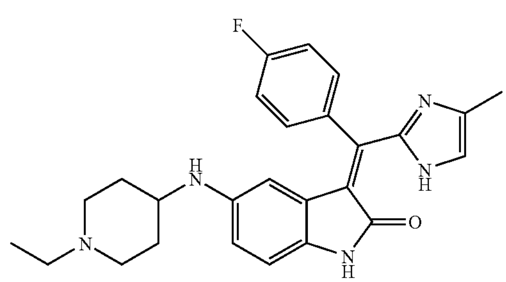 |
| 107 | (3Z)-5-[(1-ethylpiperidin-4-yl)amino]-3-[(2-fluorophenyl)(1H-imidazol-2-yl)methylidene]-1,3-dihydro-2H-indol-2-one | 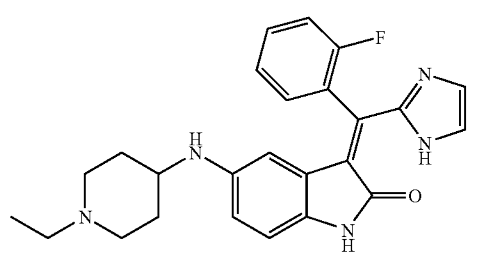 |

TABLE 1-continued

| Entry | Name | Structure |
|---|---|---|
| 108 | (3Z)-5-[(1-ethylpiperidin-4-yl)amino]-3-[[2-fluoro-4-(trifluoromethyl)phenyl](4-methyl-1H-imidazol-2-yl)methylidene]-1,3-dihydro-2H-indol-2-one | 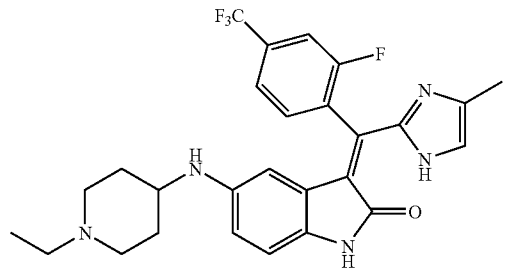 |
| 109 | (3Z)-3-[(2,3-difluorophenyl)(1H-imidazol-2-yl)methylidene]-5-[(1-ethylpiperidin-4-yl)amino]-1,3-dihydro-2H-indol-2-one | 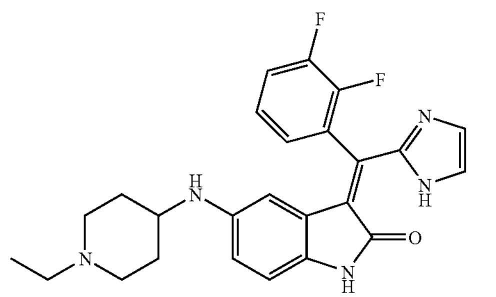 |
| 110 | (3Z)-3-[(2,3-difluorophenyl)(4-methyl-1H-imidazol-2-yl)methylidene]-5-[(1-ethylpiperidin-4-yl)amino]-1,3-dihydro-2H-indol-2-one | 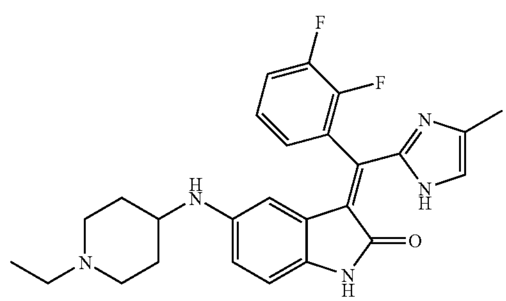 |
| 111 | (3Z)-3-[(2,4-difluorophenyl)(4-methyl-1H-imidazol-2-yl)methylidene]-5-[(1-ethylpiperidin-4-yl)amino]-1,3-dihydro-2H-indol-2-one | 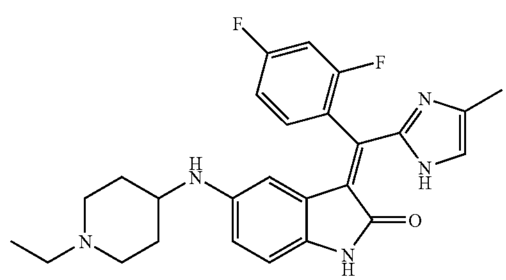 |
| 112 | (3Z)-3-[(2,4-difluorophenyl)(1H-imidazol-2-yl)methylidene]-5-[(1-ethylpiperidin-4-yl)amino]-1,3-dihydro-2H-indol-2-one | 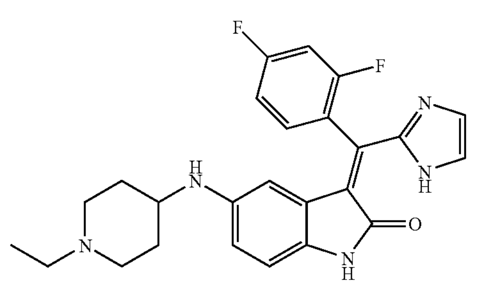 |

TABLE 1-continued

| Entry | Name |
|---|---|
| 113 | (3Z)-3-[(2-fluorophenyl)(4-methyl-1H-imidazol-2-yl)methylidene]-5-[(1-ethylpiperidin-4-yl)amino]-1,3-dihydro-2H-indol-2-one |
| 114 | (3Z)-3-[(3-trifluoromethylphenyl)(1H-imidazol-2-yl)methylidene]-5-[(1-ethylpiperidin-4-yl)amino]-1,3-dihydro-2H-indol-2-one |
| 115 | (3Z)-3-[(3-trifluoromethylphenyl)(4-methyl-1H-imidazol-2-yl)methylidene]-5-[(1-ethylpiperidin-4-yl)amino]-1,3-dihydro-2H-indol-2-one |
| 116 | (3Z)-3-[(2,4-dichloro-5-fluorophenyl)(1H-imidazol-2-yl)methylidene]-5-[(1-ethylpiperidin-4-yl)amino]-1,3-dihydro-2H-indol-2-one |
| 117 | (3Z)-3-[(2,4-dichloro-5-fluorophenyl)(4-methyl-1H-imidazol-2-yl)methylidene]-5-[(1-ethylpiperidin-4-yl)amino]-1,3-dihydro-2H-indol-2-one |

TABLE 1-continued

| Entry | Name | Structure |
|---|---|---|
| 118 | (3Z)-3-[(4-chloro-2-fluorophenyl)(4-methyl-1H-imidazol-2-yl)methylidene]-5-[(1-ethylpiperidin-4-yl)amino]-1,3-dihydro-2H-indol-2-one | 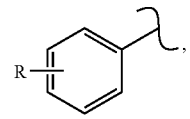 |

Embodiment [0039]: Another aspect of the invention is a pharmaceutical composition comprising a compound according to any one of embodiments [0021]-[0038] and a pharmaceutically acceptable carrier.

Embodiment [0040]: Another aspect of the invention is a metabolite of the compound or the pharmaceutical composition according to any one of embodiments [0021]-[0039].

Embodiment [0041]: Another aspect of the invention is a method of modulating the in vivo activity of a kinase, the method comprising administering to a subject an effective amount of the compound or the pharmaceutical composition according to any one of embodiments [0021]-[0039].

Embodiment [0042]: Another aspect of the invention is the method according to embodiment [0041], wherein the kinase is at least one of VEGF receptor 2 (Flk-1/KDR), FGFR1, and PDGFR (alpha and beta).

Embodiment [0043]: Another aspect of the invention is the method according to embodiment [0042], wherein modulating the in vivo activity of the kinase comprises inhibition of said kinase.

Embodiment [0044]: Another aspect of the invention is a method of treating diseases or disorders associated with uncontrolled, abnormal, and/or unwanted cellular activities, the method comprising administering, to a mammal in need thereof, a therapeutically effective amount of the compound or the pharmaceutical composition as described in any one of embodiments [0021]-[0039].

Embodiment [0045]: Another aspect of the invention is a method of screening for modulator of a kinase, the method comprising combining a compound according to any one of embodiments [0021]-[0038], and at least one candidate agent and determining the effect of the candidate agent on the activity of said kinase.

Embodiment [0046]: Another aspect of the invention is a method of inhibiting proliferative activity in a cell, the method comprising administering an effective amount of a composition comprising a compound according to any one of embodiments [0021]-[0038] to a cell or a plurality of cells.

DEFINITIONS

As used in the present specification, the following words and phrases are generally intended to have the meanings as set forth below, except to the extent that the context in which they are used indicates otherwise.

The symbol "—" means a single bond, "=" means a double bond, "≡" means a triple bond. The symbol ⁓ refers to a group on a double-bond as occupying either position on the terminus of a double bond to which the symbol is attached; that is, the geometry, E- or Z-, of the double bond is ambiguous. When a group is depicted removed from its parent formula, the ⁓ symbol will be used at the end of the bond which was theoretically cleaved in order to separate the group from its parent structural formula.

If a group "R" is depicted as "floating" on a ring system, as for example in the formula:

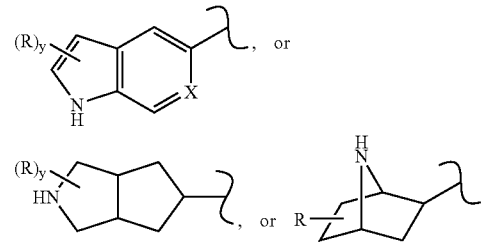

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

then, unless otherwise defined, a substituent "R" may reside on any atom of the fused ring system, assuming replacement of a depicted (for example the —NH— in the formula above), implied (for example as in the formula above, where the hydrogens are not shown but understood to be present), or expressly defined hydrogen (for example where in the formula above, "X" equals —CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When there are more than one such depicted "floating" groups, as for example in the formulae:

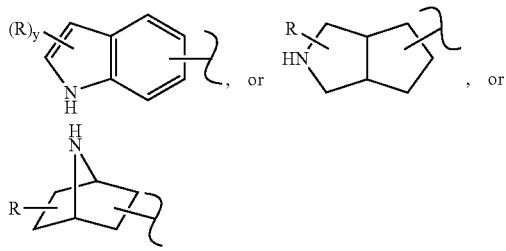

where there are two groups, namely, the "R" and the bond indicating attachment to a parent structure; then, unless otherwise defined, the "floating" groups may reside on any atoms of the ring system, again assuming each replaces a depicted, implied, or expressly defined hydrogen on the ring.

When a group "R" is depicted as existing on a ring system containing saturated carbons, as for example in the formula:

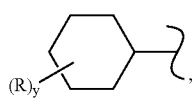

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

"Alkyl" is intended to include linear, branched, or cyclic hydrocarbon structures and combinations thereof, inclusively. For example, "$C_8$alkyl" may refer to an n-octyl, iso-octyl, cyclohexylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. Exemplary alkyl groups are those of $C_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, either "butyl" or "$C_4$alkyl" is meant to include n-butyl, sec-butyl, isobutyl, t-butyl, isobutenyl and but-2-yne radicals; and for example, "propyl" or "$C_3$alkyl" each include n-propyl, propenyl, and isopropyl.

"Alkylene" refers to straight or branched chain divalent radical consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene ($—CH_2CH_2—$), propylene ($—CH_2CH_2CH_2—$), dimethylpropylene ($—CH_2C(CH_3)_2CH_2—$), and cyclohexylpropylene ($—CH_2CH_2CH(C_6H_{13})$).

"Alkylidene" refers to a straight or branched chain unsaturated divalent radical consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically, double bond unsaturation. The unsaturation present includes at least one double bond.

"Alkylidyne" refers to a straight or branched chain unsaturated divalent radical consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above radicals, "alkylene," "alkylidene" and "alkylidyne," when optionally substituted, may contain alkyl substitution which itself contains unsaturation.

For example, 2-(2-phenylethynyl-but-3-enyl)-naphthalene (IUPAC name) contains an n-butylid-3-ynyl radical with a vinyl substituent at the 2-position of said radical.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Substituted alkoxy" refers to the group —O-(substituted alkyl), the substitution on the alkyl group generally containing more than only carbon (as defined by alkoxy). One exemplary substituted alkoxy group is "polyalkoxy" or —O-optionally substituted alkylene-optionally substituted alkoxy, and includes groups such as —$OCH_2CH_2OCH_3$, and glycol ethers such as polyethyleneglycol and —$O(CH_2CH_2O)_xCH_3$, where x is an integer of between about two and about twenty, in another example, between about two and about ten, and in a further example between about two and about five. Another exemplary substituted alkoxy group is hydroxyalkoxy or —$OCH_2(CH_2)_yOH$, where y is for example an integer of between about one and about ten, in another example y is an integer of between about one and about four.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"α-Amino Acids" refer to naturally occurring and commercially available amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, omithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), and the like.

"Amino" refers to the group —NH$_2$. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, furanyl-oxy-sulfonamino.

"Aryl" refers to aromatic six- to fourteen-membered carbocyclic ring, for example, benzene, naphthalene, indane, tetralin, fluorene and the like, univalent radicals. As univalent radicals, the aforementioned ring examples are named, phenyl, naphthyl, indanyl, tetralinyl, and fluorenyl.

"Arylene" generically refers to any aryl that has at least two groups attached thereto. For a more specific example, "phenylene" refers to a divalent phenyl ring radical. A phenylene, thus may have more than two groups attached, but is defined by the minimum of two groups attached thereto.

"Arylalkyl" refers to a residue in which an aryl moiety is attached to a parent structure via one of an alkylene, alkylidene, or alkylidyne radical. Examples include benzyl, phenethyl, phenylvinyl, phenylallyl and the like. Both the aryl, and the corresponding alkylene, alkylidene, or alkylidyne radical portion of an arylalkyl group may be optionally substituted. "Lower arylalkyl" refers to an arylalkyl where the "alkyl" portion of the group has one to six carbons; this can also be referred to as $C_{1-6}$ arylalkyl.

"Exo-alkenyl" refers to a double bond that emanates from an annular carbon, and is not within the ring system, for example the double bond depicted in the formula directly below.

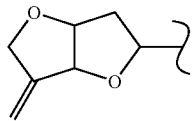

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl radicals that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroatom" refers to O, S, N, or P.

"Heterocyclyl" refers to a stable three- to fifteen-membered ring radical that consists of carbon atoms and from one to five heteroatoms selected from the group consisting of nitrogen, phosphorus, oxygen and sulfur. For purposes of this invention, the heterocyclyl radical may be a monocyclic, bicyclic or tricyclic ring system, which may include fused or bridged ring systems as well as spirocyclic systems; and the nitrogen, phosphorus, carbon or sulfur atoms in the heterocyclyl radical may be optionally oxidized to various oxidation states. In a specific example, the group —S(O)$_{0-2}$—, refers to —S— (sulfide), —S(O)— (sulfoxide), and —SO$_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring radical may be partially or fully saturated or aromatic. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl radical. A heteroalicyclic may contain unsaturation, but is not aromatic.

"Heteroaryl" refers specifically to an aromatic heterocyclyl radical.

"Heterocyclylalkyl" refers to a residue in which a heterocyclyl is attached to a parent structure via one of an alkylene, alkylidene, or alkylidyne radical. Examples include (4-methylpiperazin-1-yl) methyl, (morpholin-4-yl) methyl, (pyridine-4-yl) methyl, 2-(oxazolin-2-yl) ethyl, 4-(4-methylpiperazin-1-yl)-2-butenyl, and the like. Both the heterocyclyl, and the corresponding alkylene, alkylidene, or alkylidyne radical portion of a heterocyclylalkyl group may be optionally substituted. "Lower heterocyclylalkyl" refers to a heterocyclylalkyl where the "alkyl" portion of the group has one to six carbons. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic.

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, that only sterically practical and/or synthetically feasible compounds are meant to be included. "Optionally substituted" refers to all subsequent modifiers in a term, for example in the term "optionally substituted aryl$C_{1-8}$ alkyl," optional substitution may occur on both the "$C_{1-8}$ alkyl" portion and the "aryl" portion of the molecule; and for example, optionally substituted alkyl includes optionally substituted cycloalkyl groups, which in turn are defined as including optionally substituted alkyl groups, potentially ad infinitum. A list of exemplary optional substitution are listed below in the definition of "substituted."

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

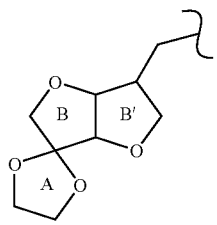

"Substituted" alkyl, aryl, and heterocyclyl, refer respectively to alkyl, aryl, and heterocyclyl, wherein one or more (for example up to about five, in another example, up to about three) hydrogen atoms are replaced by a substituent independently selected from: optionally substituted alkyl (for example, fluoromethyl), optionally substituted aryl (for example, 4-hydroxyphenyl), optionally substituted arylalkyl (for example, 1-phenyl-ethyl), optionally substituted heterocyclylalkyl (for example, 1-pyridin-3-yl-ethyl), optionally substituted heterocyclyl (for example, 5-chloro-pyridin-3-yl or 1-methyl-piperidin-4-yl), optionally substituted alkoxy, alkylenedioxy (for example methylenedioxy), optionally substituted amino (for example, alkylamino and dialkylamino), optionally substituted amidino, optionally substituted aryloxy (for example, phenoxy), optionally substituted arylalkyloxy (for example, benzyloxy), carboxy (—$CO_2H$), carboalkoxy (that is, acyloxy or —OC(=O)R), carboxyalkyl (that is, esters or —$CO_2R$), carboxamido, benzyloxycarbonylamino (CBZ-amino), cyano, acyl, halogen, hydroxy, nitro, sulfanyl, sulfinyl, sulfonyl, thiol, halogen, hydroxy, oxo, carbamyl, acylamino, and sulfonamido.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —S($O_2$)—H, —S($O_2$)-(optionally substituted alkyl), —S($O_2$)-optionally substituted aryl), —S($O_2$)-(optionally substituted heterocyclyl), —S($O_2$)-(optionally substituted alkoxy), —S($O_2$)-optionally substituted aryloxy), and —S($O_2$)-(optionally substituted heterocyclyloxy).

"Yield" for each of the reactions described herein is expressed as a percentage of the theoretical yield.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent radical, for example, —$OCH_2$—, then it is understood that either of the two partners may be bound to the particular group at one end, and the other partner is necessarily bound to the other end of the particular group, unless stated explicitly otherwise. Stated another way, divalent radicals are not to be construed as limited to the depicted orientation, for example "—$OCH_2$—" is meant to mean not only "—$OCH_2$—" as drawn, but also "—$CH_2O$—."

Methods for the preparation and/or separation and isolation of single stereoisomers from racemic mixtures or non-racemic mixtures of stereoisomers are well known in the art.

For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal lands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Utility of Compounds of the Invention as Screening Agents

To employ the compounds of the invention in a method of screening for candidate agents that bind to, for example VEGF receptor 2 (Flk-1/KDR), FGFR1, or PDGFR (alpha and beta), the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example VEGF receptor 2 (Flk-1/KDR), FGFR1, or PDGFR (alpha and beta) protein, may be done in a number of ways. In one example, the candidate agent (the compound of the invention) is labeled, for example, with a fluorescent or radioactive moiety and binding determined directly. For example, thus may be done by attaching all or a portion of the target protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the VEGF receptor 2 (Flk-1/KDR), FGFR1, or PDGFR (alpha and beta) protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. "Candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to, for example VEGF receptor 2 (Flk-1/KDR), FGFR1, and PDGFR (alpha and beta).

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to, for example VEGF receptor 2 (Flk-1/KDR), FGFR1, or PDGFR (alpha and beta), such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to, for example VEGF receptor 2 (Flk-1/KDR), FGFR1, or PDGFR (alpha and beta), for a time sufficient to allow binding, if present. Incubations may be performed at any temperature that facilitates optimal activity, typically between 4 and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to, for example VEGF receptor 2 (Flk-1/KDR), FGFR1, or PDGFR (alpha and beta), and thus is capable of binding to, and potentially modulating, the activity of the target protein. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to the target protein with a higher affinity. Thus, if the candidate agent is labeled, the presence of the label on the support, coupled with a lack of competitor binding, may indicate the candidate agent is capable of binding to the target protein.

It may be of value to identify the binding site of, for example VEGF receptor 2 (Flk-1/KDR), FGFR1, or PDGFR (alpha and beta). This can be done in a variety of ways. In one embodiment, once the target protein has been identified as binding to the candidate agent, the target protein is fragmented or modified and the assays repeated to identify the necessary components for binding.

Modulation is tested by screening for candidate agents capable of modulating the activity of, for example VEGF receptor 2 (Flk-1/KDR), FGFR1, or PDGFR (alpha and beta), comprising the steps of combining a candidate agent with the target protein, as above, and determining an alteration in the biological activity of the target protein. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to the native target protein, but cannot bind to modified target protein.

Positive controls and negative controls may be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Exemplary Embodiments

The following compounds listed in Table 2 are examples in accordance with formula I. The compounds listed in Table 2 were identified by LC-MS, and isolated. Liquid chromatography-mass spectral (LC-MS) analyses were performed using either a Hewlett-Packard Series 1100 MSD or Agilent 1100 Series LC-MSD, available from Agilent Technologies Deutschland GmbH of Waldbronn Germany. Compounds were identified according to either their observed mass [M+1] ion (positive mode) or [M−1] ion (negative mode). Two LC-MS conditions, and methods used, are as follows:

| | |
|---|---|
| Agilent, method 3.3_1 ml: (HP Series 1100 MSD) | Column: C18, 30 × 3 mm, 5 micron<br>Solvent: A 0.05 M NH4OAc/Water.<br>B Acetonitrile<br>Flow rate: 1 ml/min<br>Gradient: 0-0.25 min, 20% B<br>0.25-1.25 min, 20-90% B<br>1.25-2 min, 90% B<br>Total run time: 3 min<br>UV: 220 and 254 nm. |
| Agilent, method 3 × 3ACCN: (Agilent 1100 Series LC/MSD) | Column: C18, 30 × 4.6 mm, 3.5 micron<br>Flow rate: 2 ml/min<br>UV: 254 nm<br>Solvent and Gradient are the same as above. |

$^1$H-NMR data (taken with a Varian AS400 Spectrometer (400 MHz), available from Varian GmbH, Darmstadt, Germany) for selected compounds is provided in Table 2.

TABLE 2

| Entry | Name | $^1$H-NMR |
|---|---|---|
| 1 | (3Z)-3-[1H-benzimidazol-2-yl(3-chlorophenyl)methylidene]-5-[(1-ethylpiperidin-4-yl)(methyl)amino]-1,3-dihydro-2H-indol-2-one | (d6-DMSO): 10.98(s, 1H), 7.80-7.10(m, 8H), 6.65(d, 1H), 6.58(d, 1H), 5.05(br s, 2H), 3.05(s, 3H), 2.80(m, 2H), 1.85(m, 2H), 1.65(m, 2H), 1.20(m, 4H) ppm |
| 2 | (3Z)-3-[(3-chlorophenyl)(1H-imidazol-2-yl)methylidene]-5-[(1-ethylpiperidin-4-yl)oxy]-1,3-dihydro-2H-indol-2-one | (d6-DMSO) 7.74-7.59(m, 3H), 7.38(s, 1H), 7.26(m, 2H), 6.74-6.70(m, 2H), 5.09(s, 1H), 2.57(m, 2H), 2.32(m, 3H), 2.06(m, 3H), 1.62(m, 2H), 1.17(m, 2H), 1.00(t, 3H) ppm |
| 3 | (3Z)-3-[1H-benzimidazol-2-yl(4-chlorophenyl)methylidene]-5-[(1-ethylpiperidin-4-yl)amino]-1,3-dihydro-2H-indol-2-one | (d4-MeOH) 7.62(m, 4H), 7.42(d, 2H), 7.28(m, 2H), 6.66(d, 1H), 6.56(d, 1H), 5.20(s, 1H), 3.31(m, 2H), 3.00(q, 2H), 2.81(m, 3H), 1.92(s, 2H), 1.52(m, 2H), 1.31(t, 3H) ppm |
| 4 | (3Z)-3-[1H-benzimidazol-2-yl(3-fluorophenyl)methylidene]-5-({1-[2-(methyloxy)ethyl]piperidin-4-yl}amino)-1,3-dihydro-2H-indol-2-one | (d4-MeOH) 7.6(m, 3H), 7.4(t, 1H), 7.27(q, 2H), 7.2(m, 2H), 6.64(d, 1H), 6.55(dd, 1H), 5.2(s, 1H), 3.65(t, 2H), 3.39(s, 3H), 3.2(m, 2H), 3.0(t, 2H), 2.7(m, 1H), 2.6(t, 2H), 1.8(d, 2H), 1.6(q, 2H) ppm |
| 5 | (3Z)-3-[1H-benzimidazol-2-yl(4-fluorophenyl)methylidene]-5-({1-[2-(methyloxy)ethyl]piperidin-4-yl}amino)-1,3-dihydro-2H-indol-2-one | (d4-MeOH) 7.6(m, 2H), 7.4(m, 4H), 7.22(m, 2H), 6.64(d, 1H), 6.54(d, 1H), 5.2(s, 1H), 3.64(t, 2H), 3.39(s, 3H), 3.23(d, 2H), 2.98(t, 2H), 2.72(m, 1H), 2.6(t, 2H), 1.8(d, 2H), 1.47(q, 2H) ppm |
| 6 | (3Z)-3-[(3-chlorophenyl)(1H-imidazol-2-yl)methylidene]-5-[(1-ethylpiperidin-4-yl)amino]-1,3-dihydro-2H-indol-2-one | (d6-DMSO) 10.94(s, 1H), 7.58(m, 3H), 7.37(s, 1H), 7.26(m, 1H), 7.19(s, 1H), 6.60(d, 1H), 6.44(dd, 1H), 4.92(br. s, 1H), 4.89(d, 1H), 2.80(br. d, 2H), 2.40(q, 2H), 2.34(m, 1H), 1.93(m, 2H), 1.52(m, 2H), 1.18(m, 2H), 1.02(t, 3H) ppm |
| 7 | (3Z)-5-[(1-ethylpiperidin-4-yl)amino]-3-[(3-fluorophenyl)(1H-imidazol-2-yl)methylidene]-1,3-dihydro-2H-indol-2-one | (d6-DMSO): 11.0(br s, 0.5H), 10.45(br s, 1H), 7.80(s, 2H), 7.68(q, 1H), 7.55(br t, 1H), 7.42(m, 2H), 7.32(d, 1H), 6.58(br s, 2H), 3.50(d, 2H), 3.20-3.00(m, 3H), 2.80(m, 2H), 1.85(m, 2H), 1.70(m, 2H), 1.23(t, 3H) ppm |
| 8 | (3Z)-3-[1H-benzimidazol-2-yl(3-fluoro-4-methylphenyl)methylidene]-5-[(1-ethylpiperidin-4-yl)amino]-1,3-dihydro- | (d6-DMSO) 10.81(s, 1H), 7.66(d, 1H), 7.58(d, 1H), 7.47(t, 1H), 7.27(t, 1H), 7.17(m, 2H), 7.08(d, 1H), 6.62(d, 1H), 6.54(d, 1H), |

TABLE 2-continued

| Entry | Name | ¹H-NMR |
|---|---|---|
| | 2H-indol-2-one | 3.03(m, 2H), 2.40(s, 3H), 2.6-2.3(m, 5H), 1.74(m, 2H), 1.35(m, 2H), 1.17(t, 3H) ppm |
| 9 | (3Z)-5-[(1-ethylpiperidin-4-yl)amino]-3-[(3-fluorophenyl)(4-methyl-1H-imidazol-2-yl)methylidene]-1,3-dihydro-2H-indol-2-one | (d6-DMSO) 10.90(d, 1H), 7.57(m, 1H), 7.34(m, 1H), 7.30-6.95(m, 3H), 6.59(dd, 1H), 6.42(dd, 1H), 4.81(m, 2H), 2.77(m, 2H), 2.36(m, 3H), 2.35(s, rotamer CH3, 1.5H), 2.09(s, rotamer CH3, 1.5H), 1.89(m, 2H), 1.56(d, 2H), 1.14(m, 2H), 1.01(t, 3H) ppm. |
| 10 | (3Z)-3-[1H-benzimidazol-2-yl(4-fluoro-3-methylphenyl)methylidene]-5-[(1-ethylpiperidin-4-yl)amino]-1,3-dihydro-2H-indol-2-one | (d6-DMSO) 10.78(s, 1H), 7.66(d, 1H), 7.58(d, 1H), 7.27(m, 5H), 6.62(d, 1H), 6.51(d, 1H), 5.40(s, 1H), 5.15(m, 2H), 3.03(m, 2H), 2.77(m, 2H), 2.57(m, 3H), 2.30(s, 3H), 1.68(m, 2H), 1.41(br, 2H), 1.16(t, 3H) ppm |
| 11 | (3Z)-3-[(3-chloro-4-fluorophenyl)(1H-imidazol-2-yl)methylidene]-5-[(1-ethylpiperidin-4-yl)amino]-1,3-dihydro-2H-indol-2-one | (d6-DMSO): 12.0(br s, 0.5H), 11.0(s, 1.5H), 9.98(br s, 0.5H), 7.62(m, 2H), 7.60-7.30(m, 3H), 6.70-6.45(m, 2H), 5.38(br d, 1H), 4.90(br d, 1H), 3.45(br d, 1H), 3.20(m, 3H), 2.80(m, 3H), 1.80(m, 2H), 1.65(m, 2H), 1.23(m, 3H) ppm |
| 12 | (3Z)-3-[(3,4-difluorophenyl)(1H-imidazol-2-yl)methylidene]-5-[(1-ethylpiperidin-4-yl)amino]-1,3-dihydro-2H-indol-2-one | (d6-DMSO): 11.0(br s, 1H), 10.83(br s, 1H), 7.80-7.60(m, 5H), 7.40(br d, 1H), 6.80(br s, 2H), 3.40-2.95(m, 5H), 2.79(br q, 2H), 1.85(m, 2H), 1.70(m, 2H), 1.23(t, 3H) ppm |
| 13 | (3Z)-3-[(5-chloro-1H-benzimidazol-2-yl)(phenyl)methylidene]-5-[(1-ethylpiperidin-4-yl)amino]-1,3-dihydro-2H-indol-2-one | (CDCl3) 8.42(br s, 1H), 7.73-7.50(m, 5H), 7.42-7.40(m, 2H), 7.29-7.16(m, 1H), 6.62(d, 1H), 6.39(dd, 1H), 4.91(s, 1H), 3.21(m, 2H), 2.81(q, 2H), 2.76(m, 1H), 2.41(m, 2H), 1.92(m, 2H), 1.64(m, 2H), 1.32(t, 3H) ppm. |
| 14 | (3Z)-3-[(5-chloro-1H-benzimidazol-2-yl)(3,5-difluorophenyl)methylidene]-5-[(1-ethylpiperidin-4-yl)amino]-1,3-dihydro-2H-indol-2-one | (CDCl3) 8.94(s, 1H), 7.72-7.46(m, 2H), 7.28-7.16(m, 1H), 7.00(m, 3H), 6.55(dd, 1H), 6.41(m, 1H), 5.09(s, 1H), 3.05(m, 2H), 2.77(m, 1H), 2.60(q, 2H), 2.17(t, 2H), 1.89(d, 2H), 1.48(m, 2H), 1.19(t, 3H) ppm. |
| 15 | (3Z)-5-[(1-ethylpiperidin-4-yl)amino]-3-[(3-fluoro-4-methylphenyl)(1H-imidazol-2-yl)methylidene]-1,3-dihydro-2H-indol-2-one | (d6-DMSO) 10.97(s, 1H), 7.54(s, 1H), 7.42(t, 1H), 7.19(s, 1H), 7.09(dd, 1H), 7.00(dd, 1H), 6.61(d, 1H), 6.48(dd, 1H), 4.98(s, 1H), 4.19(m, 2H), 3.33(m, 2H), 2.61(m, 2H), 2.54(m, 1H), 2.40(s, 3H), 1.64(m, 2H), 1.22(m, 2H), 1.09(t, 3H) ppm. |
| 16 | (3Z)-5-[(1-ethylpiperidin-4-yl)amino]-3-[(4-fluorophenyl)(1H-imidazol-2-yl)methylidene]-1,3-dihydro-2H-indol-2-one | (d6-DMSO): 11.0(br s, 1H), 10.45(br s, 1H), 7.80(s, 2H), 7.50-7.40(m, 4H), 6.80(br s, 2H), 3.40-2.95(m, 5H), 2.80(m, 2H), 1.90(m, 2H), 1.70(m, 2H), 1.23(t, 3H) ppm |
| 17 | (3Z)-5-[(1-ethylpiperidin-4-yl)amino]-3-[1H-imidazol-2-yl(4-propylphenyl)methylidene]-1,3-dihydro-2H-indol-2-one | (d6-DMSO) 10.86(s, 1H), 7.52(s, 1H), 7.34(d, 2H), 7.17(d, 3H), 6.58(d, 1H), 6.46(d, 1H), 4.88(m, 2H), 2.96(m, 2H), 2.72(m, 2H), 2.50(br, 1H), 1.70(m, 4H), 1.8-1.6(m, 4H), 1.25(m, 2H), 1.1-1.01(m, 6H) ppm |
| 18 | (3Z)-5-[(1-ethylpiperidin-4-yl)amino]-3-{1H-imidazol-2-yl[4-(trifluoromethyl)phenyl]methylidene}-1,3-dihydro-2H-indol-2-one | (d6-DMSO): 11.0(br s, 1H), 10.60(br s, 1H), 7.75(s, 2H), 7.66(d, 2H), 7.0-6.68(br s, 2H), 3.40-2.95(m, 5H), 2.67(m, 2H), 1.81-1.45(m, 4H), 1.22(t, 3H) ppm |
| 19 | (3E)-3-[(3,5-difluorophenyl)(5-fluoro-1H-benzimidazol-2-yl)methylidene]-5-[(1-ethylpiperidin-4-yl)amino]-1,3-dihydro-2H-indol-2-one | (d6-DMSO): 7.61(m, 1H), 7.40(dd, 1H), 7.23(tt, 1H), 7.10(dt, 1H), 7.03(m, 2H), 6.54(d, 1H), 6.48(dd, 1H), 5.46(d, 1H), 5.0(br s, 1H), 2.18(q, 2H), 2.10(m, 2H), 1.40(m, 2H), 1.20(br t, 1H), 1.02(br t, 2H), 0.92(t, 3H) ppm |
| 20 | (3Z)-3-[(3,5-difluorophenyl)(5-fluoro-1H-benzimidazol-2-yl)methylidene]-5-[(1-ethylpiperidin-4-yl)amino]-1,3-dihydro-2H-indol-2-one | (d6-DMSO): 7.71(br s, 1H), 7.58(br s, 1H), 7.41(tt, 1H), 7.21(dd, 2H), 7.12(m, 2H), 6.62(d, 1H), 6.48(dd, 1H), 5.10(d, 1H), 5.08(br s, 1H), 2.79(br d, 2H), 2.45(m, 2H), 2.35(q, 2H), 1.60(m, 2H), 1.21(br q, 2H), 1.0(t, 3H) ppm |
| 21 | (3Z)-3-[(3-fluoro-4-methylphenyl)(1H-imidazol-2-yl)methylidene]-5-({1-[2-(methyloxy)ethyl]piperidin-4-yl}amino)-1,3-dihydro-2H-indol-2-one | (d6-DMSO) 10.94(s, 1H), 7.57(s, 1H), 742(t, 1H), 7.19(s, 1H), 7.04(dd, 1H), 6.60(dd, 1H), 6.43(dd, 1H), 5.00(s, 1H), 4.93(br. s, 1H), 3.43(m, 1H), 3.22(s, 3H), 2.81(m, 2H), 2.56(s, 3H), 2.26(m, 2H), 1.97(m, 2H), 1.58(m, 2H), 1.18(m, 2H), 0.92(m, 2H) ppm. |
| 22 | (3Z)-5-[(1-ethylpiperidin-4-yl)amino]-3-[(4-methyl-1H-imidazol-2-yl)(4-methylphenyl)methylidene]-1,3-dihydro-2H-indol-2-one | (d6-DMSO) 10.82(s, 1H), 7.28-7.26(d, 2H), 7.21-6.86(d, 1H), 7.06-7.04(d, 2H), 6.55-6.53(d, 1H), 6.39(s, 1H), 4.83(m, 1H), 2.95(m, 2H), 2.42(obs m, —CH, —CH2, rotamer CH3, 4.5H), 2.27(s, 2H), 2.02(m, rotamer CH3, 1.5H), 1.62(m, 2H), 1.33(m, 2H), 1.12(m, 3H) ppm. |
| 23 | (3Z)-5-[(1-ethylpiperidin-4-yl)amino]-3-[[3-fluoro-4-(trifluoromethyl)phenyl](1H- | (d6-DMSO) 11.05(s, 1H), 10.17(br s, rotamer NH, 0.5H), 9.46(br s, rotamer NH, 0.5H), |

TABLE 2-continued

| Entry | Name | ¹H-NMR |
|---|---|---|
|  | imidazol-2-yl)methylidene]-1,3-dihydro-2H-indol-2-one | 7.97(s, 1H), 7.62-7.57(m, 2H), 7.39-7.36(d, 1H), 7.18(s, 1H), 6.68-6.54(m, 2H), 5.40(br s, rotamer, 0.5H), 5.13(br s, rotamer, 0.5H), 4.93(br s, rotamer, 0.5H), 4.71(br s, rotamer, 0.5H), 3.42(obs m, 2H), 3.01(m, 2H), 2.55(m, 2H), 1.72(m, 2H), 1.52(m, 2H), 1.19(d, 3H) ppm. |
| 24 | (3Z)-3-[(4-chlorophenyl)(1H-imidazol-2-yl)methylidene]-5-[(1-ethylpiperidin-4-yl)amino]-1,3-dihydro-2H-indol-2-one | (d6-DMSO) 11.10-10.83(m, 1H), 7.79(s, 2H), 7.70-7.67(m, 2H), 7.52-7.50(m, 2H), 6.76(m, 2H), 3.50-3.46(m, 2H), 3.19(m, 1H), 3.05-2.98(m, 2H), 1.80-2.70(m, 2H), 1.89-1.85(m, 2H), 1.72-1.69(m, 2H), 1.27-1.22(m, 3H) ppm. |
| 25 | (3Z)-5-[(1-ethylpiperidin-4-yl)amino]-3-[(3-fluoro-4-methylphenyl)(4-methyl-1H-imidazol-2-yl)methylidene]-1,3-dihydro-2H-indol-2-one | (d6-DMSO) 10.90(s, 1H), 7.42(t, 1H), 7.04(d, 1H), 6.96(d, 2H), 6.61(d, 1H), 6.47(d, 1H), 5.10(s, 1H), 4.86(s, 1H), 2.87(m, 2H), 2.40(s, 3H), 2.33(m, 2H), 2.1(m, 1H), 1.74(m, 2H), 1.43(m, 2H), 1.18(t, 3H) ppm. |
| 26 | (3Z)-5-[(1-ethylpiperidin-4-yl)amino]-3-{1H-imidazol-2-yl[6-(trifluoromethyl)pyridin-3-yl]methylidene}-1,3-dihydro-2H-indol-2-one | (d6-DMSO) 11.00(s, 1H), 8.70(s, 1H), 8.10(s, 2H), 7.57(s, 1H), 7.17(s, 1H), 6.74(m, 1H), 6.50(m, 1H), 4.95(s, 1H), 4.81(s, 1H), 2.72(m, 2H), 2.34(m, 2H), 2.23(m, 1H), 1.91(m, 2H), 1.55(m, 2H), 1.20(m, 2H), 1.10(m, 3H) ppm. |
| 27 | (3Z)-3-[1H-imidazol-2-yl(4-methylphenyl)methylidene]-5-({1-[2-(methyloxy)ethyl]piperidin-4-yl}amino)-1,3-dihydro-2H-indol-2-one | (d6-DMSO): 10.81(s, 1H), 7.50(s, 1H), 7.35(d, 2H), 7.11(m, 3H), 7.59(d, 1H), 6.40(d, 1H), 4.95(s, 1H), 4.80(br d, 1H), 3.45(m, 2H), 3.22(s, 3H), 2.80(br s, 2H), 2.25(br s, 1H), 1.97(m, 2H), 1.55(br d, 2H), 1.19(m, 2H) ppm |
| 28 | (3Z)-3-[(3-fluorophenyl)(4-methyl-1H-imidazol-2-yl)methylidene]-5-({1-[2-(methyloxy)ethyl]piperidin-4-yl}amino)-1,3-dihydro-2H-indol-2-one | (d6-DMSO): 10.91(s, 1H), 7.58(m, 1H), 7.40(m, 1H), 7.14(m, 3H), 6.60(d, 1H), 6.42(d, 1H), 5.00(br s, 1H), 4.80(br d, 1H), 3.57(m, 2H), 3.28(s, 3H), 3.03(m, 2H), 2.82(m, 2H), 2.40(m, 2H), 2.15(m, 2H), 1.60(br d, 2H), 1.21(m, 3H) ppm |
| 29 | (3Z)-3-{1H-imidazol-2-yl[4-(trifluoromethyl)phenyl]methylidene}-5-({1-[2-(methyloxy)ethyl]piperidin-4-yl}amino)-1,3-dihydro-2H-indol-2-one | (d6-DMSO): 10.95(s, 1H), 7.85(d, 2H), 7.55(t, 3H), 7.18(s, 1H), 6.60(d, 1H), 6.42(d, 1H), 4.83(br s, 2H), 3.42(m, 2H), 3.22(s, 3H), 2.78(m, 2H), 2.30(m, 2H), 1.98(m, 2H), 1.75(m, 2H), 1.18(m, 2H) ppm |
| 30 | (3Z)-3-[(5-chloro-1H-benzimidazol-2-yl)(phenyl)methylidene]-5-({1-[2-(methyloxy)ethyl]piperidin-4-yl}amino)-1,3-dihydro-2H-indol-2-one | (d6-DMSO) 10.80(d, 1H), 7.76(d, 1H), 7.62(dd, 1H), 7.54(s, 2H), 7.34(s, 2H), 7.23(dd, 1H), 6.53(dd, 2H), 5.77(s, 1H), 5.10(d, 1H), 4.93(br. s, 1H), 4.13(m, 1H), 3.15(m, 1H), 2.84, (m, 2H), 2.53(m, 2H), 2.34(m, 2H), 2.02(m, 2H), 1.53, (m, 2H), 1.17(m, 2H) ppm. |
| 31 | (3Z)-3-[(3,5-difluorophenyl)(1H-imidazol-2-yl)methylidene]-5-[(1-ethylpiperidin-4-yl)amino]-1,3-dihydro-2H-indol-2-one | (d6-DMSO): 11.0(br s, 1H), 10.25(br s, 1H), 7.80-7.40(m, 3H), 7.22(br s, 2H), 6.60(m, 2H), 5.39(m, 1H), 5.03(br s, 1H), 3.55(br d, 2H), 3.30-2.90(m, 3H), 2.80(m, 2H), 1.82(m, 2H), 1.60(m, 2H), 1.22(m, 3H) ppm |
| 32 | (3Z)-3-[(3,5-difluorophenyl)(1H-imidazol-2-yl)methylidene]-5-({1-[2-(methyloxy)ethyl]piperidin-4-yl}amino)-1,3-dihydro-2H-indol-2-one | (d6-DMSO) 10.90(s, 1H), 7.50(s, 1H), 7.37(m, 1H), 7.13(m, 1H), 7.05(m, 2H), 6.56(d, 1H), 6.42-6.39(m, 1H), 4.93-4.88(m, 2H), 3.38(t, 2H), 3.19(s, 3H), 2.75(m, 2H), 2.48(m, 2H), 2.35(m, 1H), 1.97(m, 2H), 1.54-1.51(m, 2H), 1.15-1.12(m, 2H) ppm. |
| 33 | (3Z)-3-[(3,5-difluorophenyl)(4-methyl-1H-imidazol-2-yl)methylidene]-5-({1-[2-(methyloxy)ethyl]piperidin-4-yl}amino)-1,3-dihydro-2H-indol-2-one | (d6-DMSO) 10.91(s, 1H), 7.40(m, 1H), 7.29-6.95(d, 1H), 7.07(t, 2H), 6.60(dd, 1H), 6.43(dd, 1H), 4.93-4.85(m, 2H), 3.42(t, 2H), 3.23(s, 3H), 2.80(m, 2H), 2.51(s, 2H), 2.39(m, 1H), 2.33(s, rotamer CH3, 1.5H), 2.09(s, rotamer CH3, 1.5H), 2.00(m, 2H), 1.58-1.55(m, 2H), 1.17(m, 2H) ppm. |
| 34 | (3Z)-3-[(4-methyl-1H-imidazol-2-yl)(4-methylphenyl)methylidene]-5-({1-[2-(methyloxy)ethyl]piperidin-4-yl}amino)-1,3-dihydro-2H-indol-2-one | (d6-DMSO) 10.83(s, 1H), 7.30-7.28(d, 2H), 7.25-6.89(d, 1H), 7.10-7.08(d, 2H), 6.56-6.54(d, 1H), 6.40-6.37(dd, 1H), 4.87-4.73(m, 2H), 3.43(s, 2H), 3.23(s, 3H), 2.79(s, 2H), 2.46(s, 3H), 2.31(s, rotamer CH3, 1.5H), 2.25(s, 2H), 2.06(s, rotamer CH3, 1.5H), 1.94(s, 2H), 1.54-1.52(m, 2H), 1.11(m, 2H) ppm. |
| 35 | (3Z)-3-[(4-fluorophenyl)(1H-imidazol-2-yl)methylidene]-5-({1-[2-(methyloxy)ethyl]piperidin-4-yl}amino)-1,3-dihydro-2H-indol-2-one | (d4-MeOH) 7.40(m, 6H), 6.68(d, 1H), 6.50(d, 1H), 5.00(s, 1H), 3.60(m, 2H), 3.40(s, 3H), 3.18(m, 2H), 2.87(m, 2H), 2.64(m, 1H), 2.45(m, 2H), 1.80(m, 2H), 1.40(m, 2H) ppm. |
| 36 | (3Z)-3-[(3,4-difluorophenyl)(1H-imidazol-2-yl)methylidene]-5-({1-[2-(methyloxy)ethyl]piperidin-4-yl}amino)- | (d4-MeOH) 7.60(m, 1H), 7.30(m, 3H), 7.18(m, 1H), 6.65(d, 1H), 6.52(d, 1H), 5.10(s, 1H), 3.60(m, 2H), 3.40(s, 3H), 3.18(d, 2H), |

TABLE 2-continued

| Entry | Name | ¹H-NMR |
|---|---|---|
| | 1,3-dihydro-2H-indol-2-one | 2.87(s, 2H), 2.64(s, 1H), 2.45(s, 2H), 1.80(d, 2H), 1.40(m, 2H) ppm. |
| 37 | (3Z)-3-[(3-chloro-4-fluorophenyl)(1H-imidazol-2-yl)methylidene]-5-({1-[2-(methyloxy)ethyl]piperidin-4-yl}amino)-1,3-dihydro-2H-indol-2-one | (d6-DMSO) 10.87(s, 1H), 7.60(m, 3H), 7.32(m, 1H), 7.18(s, 1H), 6.65(d, 1H), 6.42(d, 1H), 4.96(s, 1H), 4.94(s, 1H), 3.56(m, 2H), 3.38(s, 3H), 2.80(m, 3H), 2.40(m, 2H), 2.00(m, 2H), 1.60(m, 2H), 1.20(q, 2H) ppm. |
| 38 | (3Z)-3-[(3-fluorophenyl)(1H-imidazol-2-yl)methylidene]-5-(piperidin-4-ylamino)-1,3-dihydro-2H-indol-2-one | (d6-DMSO): 7.58(q, 2H), 7.36(dt, 2H), 7.15(td, 2H), 7.10(d, 2H), 6.60(d, 1H), 6.43(d, 1H), 4.91(br s, 1H), 4.85(s, 1H), 2.87(br d, 2H), 2.43(m, 3H), 1.56(br d, 2H), 1.30(m, 2H) ppm |
| 39 | (3Z)-3-[(3-fluorophenyl)(1H-imidazol-2-yl)methylidene]-5-{[1-(2-piperidin-1-ylethyl)piperidin-4-yl]amino}-1,3-dihydro-2H-indol-2-one | (d6-DMSO): 10.90(s, 1H), 7.59(m, 2H), 7.39(t, 1H), 7.15(m, 3H), 6.80(d, 1H), 6.42(d, 1H), 4.95(br s, 1H), 4.85(s, 1H), 3.80(m, 2H), 3.00(m, 2H), 2.40(m, 4H), 1.80-1.10(m, 6H) ppm |
| 40 | (3Z)-3-[(3-fluorophenyl)(1H-imidazol-2-yl)methylidene]-5-{[1-(2-morpholin-4-ylethyl)piperidin-4-yl]amino}-1,3-dihydro-2H-indol-2-one | (d6-DMSO): 7.59(m, 2H), 7.39(t, 1H), 7.15(m, 3H), 6.80(d, 1H), 6.42(d, 1H), 4.95(s, 2H), 3.60(m, 4H), 2.80(br d, 2H), 2.40(m, 6H), 1.90(m, 5H), 1.50(br d, 2H), 1.16(br s, 1H) ppm |
| 41 | (3Z)-5-({1-[2-(diethylamino)ethyl]piperidin-4-yl}amino)-3-[(3-fluorophenyl)(1H-imidazol-2-yl)methylidene]-1,3-dihydro-2H-indol-2-one | (d6-DMSO): 7.59(m, 2H), 7.39(t, 1H), 7.15(m, 3H), 6.80(d, 1H), 6.42(d, 1H), 4.85(s, 2H), 2.80(br d, 2H), 2.40(m, 2H), 1.90(m, 9H), 1.60(br d, 2H), 1.16(br s, 1H), 1.00(t, 6H) ppm |
| 42 | (3Z)-3-[(3-fluorophenyl)(1H-imidazol-2-yl)methylidene]-5-{[1-(2-pyrrolidin-1-ylethyl)piperidin-4-yl]amino}-1,3-dihydro-2H-indol-2-one | (d6-DMSO): 7.59(m, 2H), 7.39(t, 1H), 7.15(m, 3H), 6.80(d, 1H), 6.42(d, 1H), 4.85(s, 2H), 3.60-3.40(m, 1H), 2.80(m, 2H), 2.40(m, 4H), 2.10-1.80(m, 10H), 1.50(br d, 2H), 1.16(br s, 1H) ppm |
| 43 | (3Z)-3-[1H-imidazol-2-yl(4-methylphenyl)methylidene]-5-[(1-methylpiperidin-4-yl)amino]-1,3-dihydro-2H-indol-2-one | (d4-MeOH) 7.42(d, 2H), 7.30(s, 2H), 7.19(d, 2H), 6.65(d, 1H), 6.51(d, 1H), 5.08(s, 1H), 3.1(m, 2H), 2.62(m, 1H), 2.58(s, 3H), 2.54(s, 3H), 2.56(m, 2H), 1.80(d, 2H), 1.42(m, 2H) ppm |
| 44 | (3Z)-3-[(3-fluorophenyl)(1H-1,2,4-triazol-5-yl)methylidene]-5-({1-[2-(methyloxy)ethyl]piperidin-4-yl}amino)-1,3-dihydro-2H-indol-2-one | (d4-MeOH) 8.55, 8.24(s, 1H, rotamer), 7.60(m, 1H), 7.40(m, 1H), 7.20(m, 2H), 6.65(d, 1H), 6.52(d, 1H), 5.57, 5.45(s, 1H, rotamer), 3.70(m, 2H), 3.40(s, 3H), 3.12(m, 2H), 2.85(m, 3H), 2.08(m, 2H), 1.90(m, 2H), 1.56(m, 2H) ppm. |
| 45 | ethyl 2-{(Z)-(3-fluorophenyl)[5-({1-[2-(methyloxy)ethyl]piperidin-4-yl}amino)-2-oxo-1,2-dihydro-3H-indol-3-ylidene]methyl}-4-methyl-1H-imidazole-5-carboxylate | (d6-DMSO) 11.02(s, rotamer NH, 0.5H), 10.89(s, rotamer NH, 0.5H), 7.58(q, 1H), 7.38(m, 1H), 7.20-7.15(m, 1H), 7.13-7.10(m, 1H), 6.62-6.57(m, 1H), 6.48-6.42(m, 1H), 4.93(m, 1H), 4.83(s, 1H), 4.29(q, rotamer CH2, 1H), 4.15(q, rotamer CH2, 1H), 3.43(m, 2H), 3.24(s, 3H), 2.78(m, 2H), 2.55(s, rotamer CH3, 1.5H), 2.51(obs m, 2H), 2.33(m, 1H), 2.29(s, rotamer CH3, 1.5H), 1.97(m, 2H), 1.54(m, 2H), 1.31(t, rotamer CH3, 1.5H), 1.21(t, rotamer CH3, 1.5H), 1.15-1.12(m, 2H) ppm. |
| 46 | (3Z)-3-[1H-imidazol-2-yl(phenyl)methylidene]-5-({1-[2-(methyloxy)ethyl]piperidin-4-yl}amino)-1,3-dihydro-2H-indol-2-one | (d6-DMSO) 10.95(s, 1H), 7.64(d, 1H), 7.47(m, 3H), 7.23(dd, 2H), 6.44(d, 2H), 4.80(s, 2H) 3.55(m, 1H), 3.24(s, 3H), 2.84(m, 2H), 2.59(m, 2H), 2.30(m, 2H), 2.05(m, 2H), 1.52(m, 2H), 1.13(m, 2H) ppm. |
| 47 | (3Z)-3-{1H-imidazol-2-yl[4-(methyloxy)phenyl]methylidene}-5-({1-[2-(methyloxy)ethyl]piperidin-4-yl}amino)-1,3-dihydro-2H-indol-2-one | (d6-DMSO) 10.84(s, 1H) 7.51(s, 1H), 7.18(m, 3H), 7.07(m, 2H), 6.50(dd, 2H), 5.01(s, 1H), 4.85(br. s, 1H), 4.13(d, 2H), 3.87(s, 3H), 3.45(m, 1H), 3.25(s, 3H), 2.78(m, 2H), 2.33(m, 2H), 1.94(m, 2H), 1.54(m, 2H), 1.14(m, 2H) ppm. |
| 48 | (3Z)-3-[(4-chlorophenyl)(1H-imidazol-2-yl)methylidene]-5-({1-[2-(methyloxy)ethyl]piperidin-4-yl}amino)-1,3-dihydro-2H-indol-2-one | (d6-DMSO) 10.93(s, 1H)7.58(m, 3H), 7.32(d, 2H), 7.18(s, 1H), 6.54(dd, 2H), 4.90(br. s, 1H), 4.88(s, 1H), 3.47(m, 1H), 3.24(s, 3H), 2.84(m, 2H), 2.56(m, 2H), 2.32(m, 2H), 2.11(m, 2H), 1.58(m, 2H), 1.18(m, 2H) ppm. |
| 49 | (3Z)-3-[[3-fluoro-4-(trifluoromethyl)phenyl](1H-imidazol-2-yl)methylidene]-5-({1-[2-(methyloxy)ethyl]piperidin-4-yl}amino)-1,3-dihydro-2H-indol-2-one | (d6-DMSO) 11.00(s, 1H), 7.94(s, 1H), 7.62(m, 2H), 7.39(m, 1H), 7.20(m, 1H), 6.58(dd, 2H), 4.93(s, 1H), 3.45(m, 1H), 3.23(m, 3H), 2.72(m, 2H), 2.32(m, 2H), 2.00(m, 2H), 1.55(m, 2H), 1.20(m, 2H), 0.84(m, 2H) ppm. |
| 50 | (3Z)-3-[(3-fluorophenyl)(1H-imidazol-2-yl)methylidene]-5-{[1-(methylsulfonyl)piperidin-4-yl]amino}-1,3- | (d6-DMSO): 7.62(q, 1H), 7.60(s, 1H), 7.50(dt, 1H), 7.20(s, 1H), 7.15(m, 2H), 6.82(d, 1H), 6.45(d, 1H), 5.05(d, 1H), 4.82(s, 1H), |

TABLE 2-continued

| Entry | Name | ¹H-NMR |
|---|---|---|
| | dihydro-2H-indol-2-one | 3.50(m, 2H), 2.95(s, 3H), 2.70(m, 2H), 1.65(br d, 2H), 1.21(m, 2H) ppm |
| 51 | (3Z)-3-[1H-imidazol-2-yl(4-propylphenyl)methylidene]-5-({1-[2-(methyloxy)ethyl]piperidin-4-yl}amino)-1,3-dihydro-2H-indol-2-one | (d6-DMSO) 10.84(s, 1H), 7.50(s, 1H), 7.32-7.29(d, 2H), 7.13-7.11(m, 3H), 6.56-6.54(d, 1H), 6.42-6.41(m, 1H), 4.89(m, 1H), 4.67-4.64(m, 1H), 3.42(t, 2H), 3.23(s, 3H), 2.78-2.70(m, 4H), 2.46(obs m, 2H), 2.27(m, 1H), 1.93(m, 2H), 1.76-1.70(m, 2H), 1.54-1.52(m, 2H), 1.14-1.08(m, 2H), 1.02(t, 3H) ppm. |
| 52 | (3Z)-5-[(1-ethylpiperidin-4-yl)amino]-3-[(3-fluorophenyl)(4-phenyl-1H-imidazol-2-yl)methylidene]-1,3-dihydro-2H-indol-2-one | (d6-DMSO) 11.00(d, 1H), 8.07(d, 1H), 7.73(d, 1H), 7.64(m, 1H), 7.62(d, 1H), 7.53(t, 1H), 7.41(m, 1H), 7.39(d, 1H), 7.33(t, 1H), 7.22(m, 2H), 6.65(dd, 1H), 6.49(t, 1H), 4.98(br. s, 1H), 4.88(s, 1H), 4.18(m, 2H), 2.91(m, 1H), 2.47(q, 2H), 1.62(m, 2H), 1.24(m, 2H), 1.10(m, 2H), 0.83(t, 3H) ppm. |
| 53 | (3Z)-3-[(3-fluorophenyl)(4-phenyl-1H-imidazol-2-yl)methylidene]-5-({1-[2-(methyloxy)ethyl]piperidin-4-yl}amino)-1,3-dihydro-2H-indol-2-one | (d6-DMSO) 11.01(d, 1H), 8.07(d, 1H), 7.69(dd, 2H), 7.62(m, 1H), 7.53(t, 1H), 7.42(m, 1H), 7.40(d, 1H), 7.33(t, 2H), 7.23(m, 2H), 6.64(dd, 1H), 6.47(t, 1H), 4.91(br. s, 1H), 4.90(s, 1H), 3.48(m, 2H), 3.27(s, 3H), 2.81(m, 2H), 2.38(m, 2H), 2.00(m, 2H), 1.59(m, 2H), 1.23(m, 1H), 1.20(m, 2H) ppm. |
| 54 | (3Z)-3-[(3-fluoro-4-methylphenyl)(4-methyl-1H-imidazol-2-yl)methylidene]-5-({1-[2-(methyloxy)ethyl]piperidin-4-yl}amino)-1,3-dihydro-2H-indol-2-one | (d6-DMSO) 10.90(d, 1H), 7.42(q, 1H), 7.30(s, 1H), 7.08(t, 1H), 6.96(m, 1H), 6.61(m, 1H), 6.43(d, 1H), 4.92(d, 1H), 4.82(br. s, 1H), 3.43(m, 2H), 3.25(s, 3H), 2.80(m, 2H), 2.33(s, 3H), 2.31(m, 2H), 2.10(s, 3H), 1.92(m, 2H), 1.58(m, 2H), 1.21(m, 1H), 1.13(m, 2H) ppm. |
| 55 | (3Z)-3-{1H-imidazol-2-yl[6-(trifluoromethyl)pyridin-3-yl]methylidene}-5-({1-[2-(methyloxy)ethyl]piperidin-4-yl}amino)-1,3-dihydro-2H-indol-2-one | (d4-MeOH) 8.68(s, 1H), 8.08(m, 2H), 7.48(s, 1H), 7.36(s, 1H), 6.65(d, 1H), 6.52(d, 1H), 5.0(s, 1H), 3.60(m, 2H), 3.40(s, 3H), 3.10(d, 2H), 2.91(m, 2H), 2.45(m, 3H), 1.80(m, 2H), 1.40(m, 2H) ppm. |
| 56 | (3Z)-5-[(1-ethylpiperidin-4-yl)amino]-3-[(3-fluorophenyl)(1H-1,2,4-triazol-5-yl)methylidene]-1,3-dihydro-2H-indol-2-one | (d4-MeOH) 8.52, 8.23(s, 1H, rotamer), 7.61(m, 1H), 7.38(m, 1H), 7.18(m, 2H), 6.61(m, 2H), 5.56, 5.49(s, 1H, rotamer), 3.26(m, 2H), 2.90(m, 2H), 2.76(m, 1H), 2.52(m, 2H), 1.91(m, 2H), 1.43(m, 2H), 1.21(t, 3H) ppm. |
| 57 | (3Z)-5-[(1-ethylpiperidin-4-yl)amino]-3-[[2-fluoro-4-(trifluoromethyl)phenyl](1H-imidazol-2-yl)methylidene]-1,3-dihydro-2H-indol-2-one | (d4-MeOH) 7.91(m, 2H), 7.88(m, 1H), 7.76(s, 2H), 7.18(d, 2H), 7.00(d, 2H), 6.00(s, 1H), 3.68(d, 2H), 3.20(q, 2H), 2.98(t, 2H), 2.18(d, 2H), 1.82(m, 3H), 1.41(t, 3H) ppm. |
| 58 | (3Z)-5-[(1-ethylpiperidin-4-yl)amino]-3-{(4-methyl-1H-imidazol-2-yl)[4-(trifluoromethyl)phenyl]methylidene}-1,3-dihydro-2H-indol-2-one | (d6-DMSO) 10.93-10.92(d, 1H), 7.88(m, 2H), 7.49(t, 2H), 7.30-6.92(d, 1H), 6.62-6.59(m, 1H), 6.47-6.44(m, 1H), 4.90-4.70(m, 2H), 4.10(m, 1H), 3.15(s, 2H), 2.77(m, 2H), 2.34(s, rotamer CH3, 1.5H), 2.3(obs m, 1.5H), 2.07(s, rotamer CH3, 1.5H), 1.56(m, 2H), 1.14(m, 2H), 1.05(m, 3H) ppm. |
| 59 | (3Z)-5-[(1-ethylpiperidin-4-yl)amino]-3-{(4-methyl-1H-imidazol-2-yl)[4-(trifluoromethyl)phenyl]methylidene}-1,3-dihydro-2H-indol-2-one | (d6-DMSO): 11.15(br s, 1H), 10.70(br s, 1H), 8.00(d, 1H), 7.78(d, 2H), 7.59(d, 1H), 7.10-6.80(m, 2H), 5.92(br s, 1H), 3.20(m, 1H), 3.00(m, 4H), 2.71(m, 2H), 2.29(s, 3H), 1.92-1.59(m, 4H), 1.21(t, 3H) ppm |
| 60 | (3Z)-3-[(4-chlorophenyl)(4-methyl-1H-imidazol-2-yl)methylidene]-5-[(1-ethylpiperidin-4-yl)amino]-1,3-dihydro-2H-indol-2-one | (d6-DMSO) 11.20(br. s, 1H), 10.41(br. s, 1H), 8.10(m, 2H), 7.82(m, 2H), 7.60(m, 2H), 6.84(m, 2H), 3.24(m, 2H), 3.01(q, 2H), 2.73(m, 2H), 1.92(m, 2H), 1.81(m, 1H), 1.68(m, 2H), 1.22(t, 3H) ppm. |
| 61 | (3Z)-5-[(1-ethylpiperidin-4-yl)amino]-3-[[3-fluoro-4-(trifluoromethyl)phenyl](4-methyl-1H-imidazol-2-yl)methylidene]-1,3-dihydro-2H-indol-2-one | (d6-DMSO) 11.03(br. s, rot NH, 0.3H), 10.92(br. s, rot NH, 0.7H), 10.43(br. s, 1H), 7.72(m, 2H), 7.54(m, 2H), 6.73(m, 2H), 5.49(s, 1H), 4.20(m, 2H), 3.23(m, 1H), 3.09(m, 2H), 2.74(m, 2H), 2.32(s, 3H), 1.83(m, 2H), 1.61(m, 2H), 1.24(m, 3H) ppm. |
| 62 | (3Z)-3-[(3,4-difluorophenyl)(4-methyl-1H-imidazol-2-yl)methylidene]-5-[(1-ethylpiperidin-4-yl)amino]-1,3-dihydro-2H-indol-2-one | (d6-DMSO): 11.15(br s, 1H), 10.46(br s, 1H), 7.67(m, 2H), 7.53(s, 1H), 7.32(m, 1H), 6.79(m, 2H), 5.92(v br s, 1H), 3.41(br d, 2H), 3.20-2.90(m, 3H), 2.73(m, 2H), 2.21(s, 3H), 1.88-1.60(m, 4H), 1.21(m, 3H) ppm |
| 63 | (3Z)-3-[(3-chloro-4-fluorophenyl)(4-methyl-1H-imidazol-2-yl)methylidene]-5-[(1-ethylpiperidin-4-yl)amino]-1,3-dihydro-2H-indol-2-one | (d6-DMSO): 11.15(br s, 1H), 10.40(br s, 1H), 7.80(m, 1H), 7.70(m, 1H), 7.50(m, 3H), 6.79(m, 2H), 3.10(m, 3H), 2.80(m, 2H), 2.30(s, 3H), 1.90(m, 2H), 1.70(m, 2H), 1.25(m, 2H), 1.20(t, 3H) ppm |

TABLE 2-continued

| Entry | Name | ¹H-NMR |
|---|---|---|
| 64 | (3Z)-5-[(1-ethylpiperidin-4-yl)amino]-3-[(4-fluorophenyl)(4-methyl-1H-imidazol-2-yl)methylidene]-1,3-dihydro-2H-indol-2-one | (d4-MeOH) 7.38(m, 4H), 7.12(s, 1H), 6.63(d, 1H), 6.5(d, 1H), 4.95(s, 1H), 3.4(m, 2H), 3.1(q, 2H), 2.9(m, 3H), 2.35(s, 3H), 1.92(d, 2H), 1.55(m, 2H), 1.35(t, 3H) ppm |
| 65 | (3Z)-5-[(1-ethylpiperidin-4-yl)amino]-3-[(2-fluorophenyl)(1H-imidazol-2-yl)methylidene]-1,3-dihydro-2H-indol-2-one | (d6-DMSO) 7.56-7.18(m, 6H), 6.60-6.58(d, 1H), 6.45-6.42(dd, 1H), 4.92-4.87(m, 2H), 2.74-2.72(m, 2H), 2.34-2.25(m, 3H), 1.83(obs m, 2H), 1.51(m, 2H), 1.10(m, 2H), 0.98(t, 3H) ppm. |
| 66 | (3Z)-5-[(1-ethylpiperidin-4-yl)amino]-3-[[2-fluoro-4-(trifluoromethyl)phenyl](4-methyl-1H-imidazol-2-yl)methylidene]-1,3-dihydro-2H-indol-2-one | (d6-DMSO): 11.00(br s, 1H), 10.10(br s, 1H), 8.00(d, 1H), 7.80(d, 1H), 7.78(m, 2H), 7.45(m, 2H), 6.65(br s, 2H), 3.20-2.95(m, 3H), 2.80(m, 1H), 2.60(m, 2H), 2.25(s, 3H), 1.80(m, 2H), 1.75-1.40(m, 3H), 1.20(m, 3H) ppm |
| 67 | (3Z)-3-[(2,3-difluorophenyl)(1H-imidazol-2-yl)methylidene]-5-[(1-ethylpiperidin-4-yl)amino]-1,3-dihydro-2H-indol-2-one | (d4-MeOH) 7.61(m, 1H), 7.42(m, 1H), 7.18(m, 1H), 6.69(d, 1H), 6.58(d, 1H), 5.16(s, 1H), 3.31(m, 2H), 3.00(q, 2H), 2.81(m, 1H), 2.71(m, 2H), 1.92(m, 2H), 1.52(m, 2H), 1.31(t, 3H) ppm. |
| 68 | (3Z)-3-[(2,3-difluorophenyl)(4-methyl-1H-imidazol-2-yl)methylidene]-5-[(1-ethylpiperidin-4-yl)amino]-1,3-dihydro-2H-indol-2-one | (d6-DMSO): 11.00(br s, 1H), 10.20(br s, 1H), 7.80(m, 1H), 7.50(m, 2H), 7.30(m, 1H), 6.70(br s, 2H), 5.30(br s, 1H), 3.20-2.95(m, 4H), 2.90-2.60(m, 2H), 2.25(s, 3H), 1.80(m, 2H), 1.50(m, 2H), 1.20(t, 3H) ppm |
| 69 | (3Z)-3-[(2,4-difluorophenyl)(4-methyl-1H-imidazol-2-yl)methylidene]-5-[(1-ethylpiperidin-4-yl)amino]-1,3-dihydro-2H-indol-2-one | (d6-DMSO): 11.00(br s, 1H), 7.60(m, 1H), 7.40(m, 1H), 7.30(s, 1H), 7.15(s, 1H), 7.10(s, 1H), 3.20(m, 3H), 3.10(m, 2H), 2.80(m, 2H), 2.30(rotamer m, 3H), 1.90-1.40(m, 4H), 1.20(t, 3H) ppm |
| 70 | (3Z)-3-[(2,4-difluorophenyl)(1H-imidazol-2-yl)methylidene]-5-[(1-ethylpiperidin-4-yl)amino]-1,3-dihydro-2H-indol-2-one | (d6-MeOH): 7.40(m, 2H), 7.25(m, 3H), 6.65(d, 1H), 6.55(d, 1H), 5.15(d, 1H), 3.16(m, 2H), 2.77(m, 3H), 2.50(m, 2H), 1.87(m, 2H), 1.40(m, 2H), 1.24(t, 3H) ppm |
| 71 | (3Z)-3-[(2-fluorophenyl)(4-methyl-1H-imidazol-2-yl)methylidene]-5-[(1-ethylpiperidin-4-yl)amino]-1,3-dihydro-2H-indol-2-one | (d6-DMSO) 15.15-15.12(m, 1H), 10.93-10.91(m, 1H), 7.60-7.53(m, 1H), 7.39-6.92(m, 4H), 6.61-6.57(dd, 1H), 6.44-6.41(dd, 1H), 4.90-4.81(m, 2H), 2.74(m, 2H), 2.33-2.30(m, CH, CH2, rotamer CH3, 4.5H), 2.07(s, rotamer CH3, 1.5H), 1.84(m, 2H), 1.54-1.50(m, 2H), 1.16-1.05(m, 2H), 0.99(t, 3H) ppm. |
| 72 | (3Z)-3-[(3-trifluoromethylphenyl)(1H-imidazol-2-yl)methylidene]-5-[(1-ethylpiperidin-4-yl)amino]-1,3-dihydro-2H-indol-2-one | (d6-DMSO) 10.97(s, 1H), 7.91(d, 1H), 7.80(t, 1H), 7.68(s, 1H), 7.62(d, 1H), 7.56(s, 1H), 7.19(s, 1H), 6.61(d, 1H), 6.45(dd, 1H), 4.96(br. s, 1H), 4.72(s, 1H), 3.35(m, 2H), 3.18(s, 3H), 2.82(m, 2H), 2.48(m, 1H), 2.28(m, 2H), 1.5(m, 2H), 1.06(t, 3H), 0.82(m, 2H) ppm. |
| 73 | (3Z)-3-[(3-trifluoromethylphenyl)(4-methyl-1H-imidazol-2-yl)methylidene]-5-[(1-ethylpiperidin-4-yl)amino]-1,3-dihydro-2H-indol-2-one | (d6-DMSO) 11.12(br. d, 1H), 10.70(s, 1H), 8.08(d, 1H), 7.94(dd, 1H), 7.88(m, 3H), 7.59(s, 1H), 6.85(br. m, 2H), 3.46(m, 2H), 3.16(m, 1H), 3.05(m, 2H), 2.72(q, 2H), 2.31(s, 3H), 1.85(m, 2H), 1.72(m, 2H), 1.23(t, 3H) ppm. |
| 74 | (3Z)-3-[(2,4-dichloro-5-fluorophenyl)(1H-imidazol-2-yl)methylidene]-5-[(1-ethylpiperidin-4-yl)amino]-1,3-dihydro-2H-indol-2-one | (d6-DMSO) 11.38(br. m, 1H), 10.62(br. s, 1H), 8.11(m, 1H), 7.78(m, 3H), 7.11(br. s, 1H), 6.89(br. s, 1H), 5.85(br. s, 1H), 3.43(m, 2H), 3.18(m, 1H), 2.96(m, 2H), 2.75(m, 2H), 1.90(m, 2H), 1.76(m, 2H), 1.19(t, 3H) ppm. |
| 75 | (3Z)-3-[(2,4-dichloro-5-fluorophenyl)(4-methyl-1H-imidazol-2-yl)methylidene]-5-[(1-ethylpiperidin-4-yl)amino]-1,3-dihydro-2H-indol-2-one | (d4-MeOH) 7.82(d, 1H), 7.38(d, 1H), 7.08(s, 1H), 6.66(d, 1H), 6.56(d, 1H), 5.10(s, 1H), 3.31(m, 2H), 3.00(q, 2H), 2.81(m, 3H), 2.32(s, 3H), 1.92(m, 2H), 1.52(m, 2H), 1.31(t, 3H) ppm |
| 76 | (3Z)-3-[(4-chloro-2-fluorophenyl)(4-methyl-1H-imidazol-2-yl)methylidene]-5-[(1-ethylpiperidin-4-yl)amino]-1,3-dihydro-2H-indol-2-one | (d6-DMSO) 10.96(br. s, 1H), 7.64(t, 1H), 7.45(m, 1H), 7.40(q, 1H), 6.95(s, 1H), 6.62(m, 1H), 6.49(dd, 1H), 5.03(s, 1H), 4.96(br. s 1H), 4.11(m, 1H), 3.18(s, 3H), 2.79(m, 1H), 2.34(q, 2H), 1.92(m, 2H), 1.60(m, 2H), 1.15(m, 2H), 1.01(t, 3H) ppm. |

ABBREVIATIONS AND THEIR DEFINITIONS

The following abbreviations and terms have the indicated meanings throughout:

Ac=acetyl

BNB=4-bromomethyl-3-nitrobenzoic acid

Boc=t-butyloxy carbonyl

Bu=butyl c-=cyclo

CBZ=carbobenzoxy=benzyloxycarbonyl

DBU=diazabicyclo[5.4.0]undec-7-ere

DCM=dichloromethane=methylene chloride=$CH_2Cl_2$

DCE=dichloroethylene

DEAD=diethyl azodicarboxylate

DIC=diisopropylcarbodiimide

DIEA=N,N-diisopropylethyl amine

DMAP=4-N,N-dimethylaminopyridine

DMF=N,N-dimethylformamide

DMSO=dimethyl sulfoxide

DVB=1,4-divinylbenzene

EEDQ=2-ethoxy-1-ethoxycarbonyl-1,2-dihydroquinoline

Et=ethyl

Fmoc=9-fluorenylmethoxycarbonyl

GC=gas chromatography

HATU=O-(7-Azabenzotriazol-1-yl)-1,1,3,3-tetramethyluronium hexafluorophosphate

HMDS=hexamethyldisilazane

HOAc=acetic acid

HOBt=hydroxybenzotriazole

Me=methyl mesyl=methanesulfonyl

MTBE=methyl t-butyl ether

NMO=N-methylmorpholine oxide

PEG=polyethylene glycol

Ph=phenyl

PhOH=phenol

PfP=pentafluorophenol

PfPy=pentafluoropyridine

PPTS=pyridinium p-toluenesulfonate

Py=pyridine

PyBroP=bromo-tris-pyrrolidino-phosphonium hexafluorophosphate

RT=room temperature

Sat'd=saturated s-=secondary t-=tertiary

TBDMS=t-butyldimethylsilyl

TES=triethylsilane

TFA=trifluoroacetic acid

THF=tetrahydrofuran

TMOF=trimethyl orthoformate

TMS=trimethylsilyl tosyl=p-toluenesulfonyl

Trt=triphenylmethyl

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

Synthesis of Compounds

The following specific examples are provided as a guide to assist in the practice of the invention, and are not intended as a limitation on the scope of the invention. Using these examples as a guide, one skilled in art can synthesize compounds of the invention. Many starting materials and intermediates are commercially available. For example, there are many commercially available benzimidazole starting materials; and many benzimidazole syntheses, which use commercially available starting materials, are well known in the art.

Example 1

General Procedure for C-Acylation of Benzimidazoles

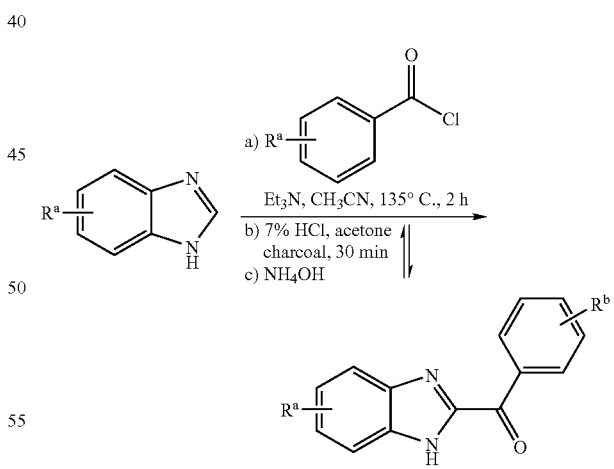

To a 15 mL pressure tube was added benzimidazole (1 mmol) and a stirbar. Acetonitrile (4.7 mmol) was added. Triethylamine (2.9 mmol) was added followed by the appropriately substituted benzoyl chloride (2.9 mmol). Upon addition of the benzoyl chloride, the mixture became warm and viscous. The tube was sealed and heated at 135° C. for 2 hours while stirring. During heating, the mixture turned black in color. The tube was removed from the heat and its contents were diluted with acetone (approximately 3-4 mL per mmol of benzimidazole). The mixture was transferred to a round-bottomed flask containing 7% aqueous HCl (approximately 10-15 mL per mmol of benzimidazole). Charcoal was added to the flask and the mixture was refluxed at 85° C. for 30 minutes. The mixture was allowed to cool and then was filtered through a Celite pad followed by a rinse with 1N HCl (25 mL). The filtrate was made alkaline with $NH_4OH$ whereupon a solid precipitate formed. The solid was filtered, collected, and placed under high vacuum, yielding a solid ranging from white to brown, depending on the substituted benzoyl chloride used.

Example 2

General Procedure for the Condensation of Oxindoles with Substituted Benzoylbenzimidazoles

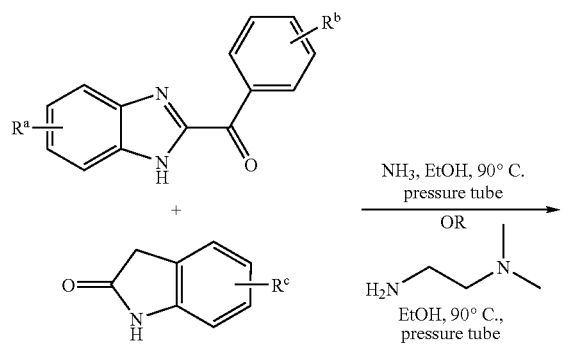

Procedure using ammonia: To a 15 mL pressure tube was added benzoylbenzimidazole (1 mmol), oxindole (1.05 mmol) and a stirbar. Anhydrous EtOH (approximately 5 mL per 1 mmol benzoylbenzimidazole) was added and the reaction vessel was cooled to 0° C. in an ice bath. $NH_3$ (g) was bubbled into the solution until saturation was achieved. The reaction vessel was sealed tightly and was heated at 90° C. overnight with stirring. After heating, the reaction mixture was dark and in some cases, a precipitate had formed. In cases where precipitation occurred, the bright yellow or orange crystals were filtered, collected, and confirmed to be the desired product. In cases where no precipitation was evident, the mixture was concentrated and purified via flash chromatography (15% to 50% EtOAc/Hex) to give bright yellow or orange crystals.

Procedure using unsym-dimethylethylenediamine: The procedure is the same as above with unsym-dimethylethylenediamine (5 mmol) used in lieu of $NH_3$ (g). Prior cooling to 0° C. is not necessary.

Example 3

2-chloro-N-(4-methoxyphenyl)-acetamide

An Oxindole Starting Material

To a 500 ml round bottom flask was added p-anisidine (200 mmol), dichloromethane (100 ml) and triethylamine (250 mmol). The mixture was cooled to 0° C. and chloroacetyl chloride (220 mmol) in dichloromethane (20 ml) was added dropwise. The reaction was stirred at room temperature overnight. The reaction was concentrated and ethyl acetate was added to the solid. The solid was filtered off and the filtrate concentrated in vacuo to give product.

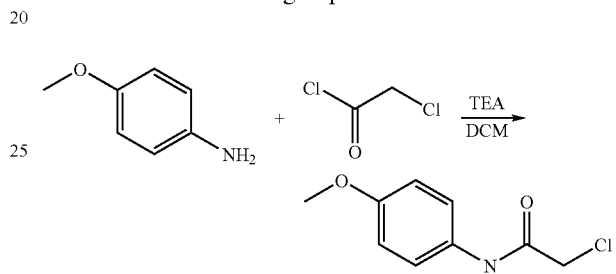

Example 4

5-hydroxyoxindole 2-chloro-N-(4-methoxyphenyl)-acetamide (10 g) and Anhydrous aluminum trichloride (17 g) was heated to 120° C. for 15 minutes and then heated to 240° C. for 1 hour. The reaction was cooled to room temperature and quenched with ice water and Concentrate hydrochloride acid, and extracted with ethyl acetate (5×). Organic layers combined and dried over magnesium sulfate, filtered and concentrated in vacuo. The crude solid was flash chromatography (silica, ethyl acetate) to give product.

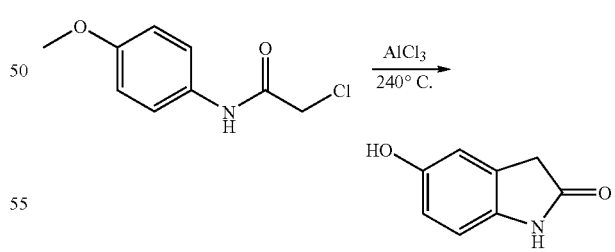

Example 5

5-[1-(2-methoxyethyl)-piperidin-4-yloxy]-1,3-dihydro-indol-2-one

To an oven dried, nitrogen flushed 100 ml round bottom flask was added 5-hydroxyoxindole (10 mmol), 1-(2-methoxyethyl)-piperidin-4-ol (11 mmol), triphenylphosphine (15 mmol), Anhydrous tetrahydrofuran (35 ml) and a stirrer bar. Diethyl azodicarboxylate (15 mmol) was added slowly to the mixture and stirred at room temperature overnight. The reaction was concentrated in vacuo and flash chromatography (silica, 5% methanol in ethyl acetate). Upon concentration a reddish oil (470 mg) was obtained with a 75% purity by H-NMR and LC/MS.

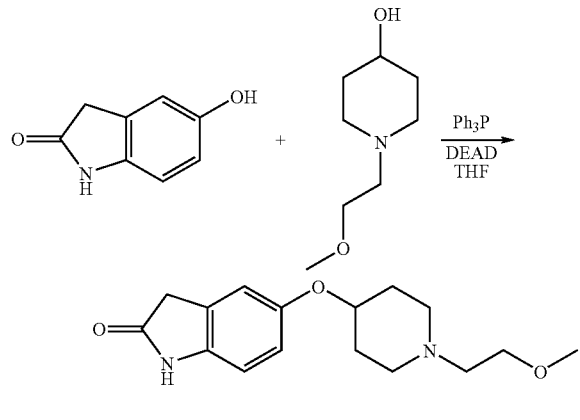

Example 6

General Procedure for the Reductive Amination of 5-amino-oxindoles with Ketones

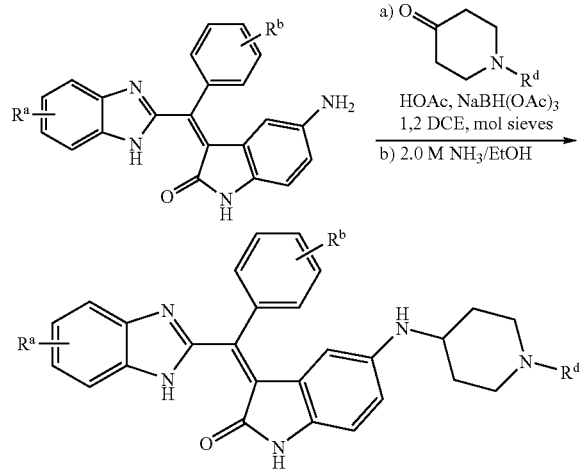

To a 250 mL round bottom was added 5-amino-oxindole (2.61 mmol), dry 1,2 dichloroethane (80 mL), ketone (2.61 mmol), glacial acetic acid (1.35 mmol), and 4 A molecular sieves. The reaction mixture was stirred at rt for 10 min. The reaction was then cooled to 0° C. in an ice bath before sodium triacetoxyborohydride (3.91 mmol) was added in one portion. The reaction was then warmed to rt and stirred overnight or until all starting materials are consumed. In cases where the reaction had not gone to completion, another 0.5 eq of sodium triacetoxy borohydride was added, and allowed to continue stirring at rt until the reaction was completed. The molecular sieves were removed via filtration and rinsed with a minimum amount of methanol. The filtrate was then basified with 5.0 mL of 2.0 M ammonia in Ethanol, concentrated via rotary evaporation, and purified by flash chromatography (typically with 90:10 $CH_2Cl_2$:MeOH) to give a brown oil. The oil was then lyophilized to give the product as a brown fluffy solid.

Alternatively, the reductive amination can be performed on the 5-amino-oxindole (5-amino-oxindole itself is commercially available from Combi-Blocs of San Diego Calif.) before condensation using the same procedure above. The solubility of polar starting materials may be aided with the addition of dry DMF (up to 25% v/v).

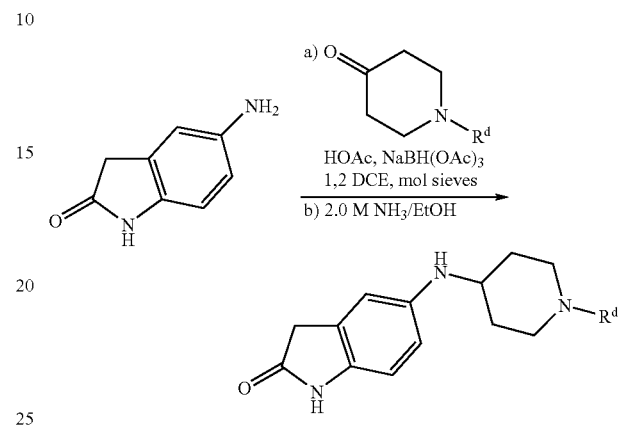

Also alternatively, the reduction amination can be carried out, for example, as follows:

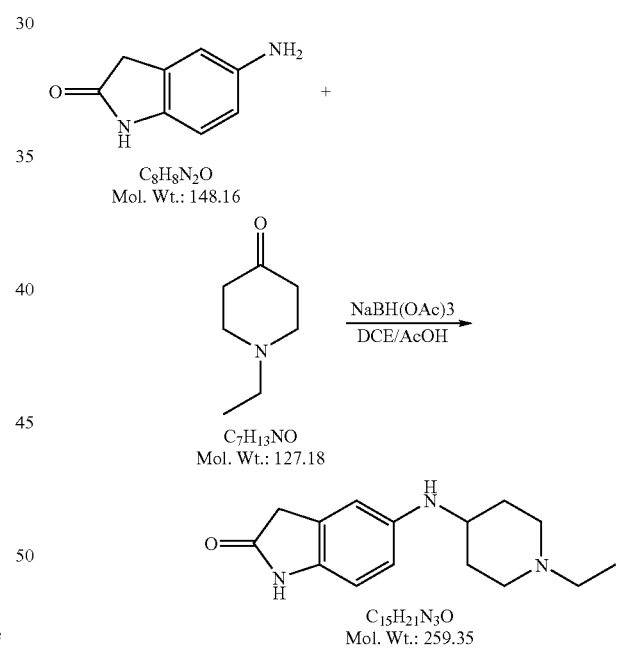

5-(1-Ethyl-piperidin-4-ylamino)-1,3-dihydro-indol-2-one. To a 2 L round bottom flask was added 5-aminooxindole (80 g, 0.54 mol), 1,2-dichloroethane (800 ml), 1-ethyl-4-piperidone (80.1 ml, 0.59 mmol) and Glacial acetic acid (80 ml). The mixture was stirred for 30 minutes, cooled under ice/water bath for 30 minutes and then sodium triacetoxyborohydride (160 g, 0.76 mmol) was added in 10 portions over 60 minutes. The mixture was stirred at room temperature 4 hs. TLC showed no trace of amino-oxindole and then Celite (100 g) and MeOH (500 mL) were slowly added. The reaction mixture was filtered and concentrated. The resulting dark oil was acidified with c-HCl (150 mL) and ice (50 g). The reaction mixture was extracted with ethyl acetate (2 L×2) to remove the side product. The aqueous layer was cooled to 0° C., basified with 40% NaOH (ca. 150 mL) and then the solid was formed. After 30 min stirring, the formed solid was filtered and washed with H₂O (1 L) and suspended with Acetone (2 L) for 1 h. After filtering, the crude solid was dissolved in CHCl₃ (2.5 L), treated with charcoal (50 g) and filtered using Celite. The filterate was concentrated and solidified with ethyl acetate to give the desired product (81 g, 58%).

Example 7

Synthesis of 3-[(1H-Benzoimidazol-2-yl)-(3-chlorophenyl)-methylene]-5-[1-(2-methoxyethyl)-piperidin-4-yloxy]-1,3-dihydro-pyrrolo[3.2-b]pyridin-2-one 2-(6-Chloro-3-nitro-pyridin-2-yl)-malonic acid tert-butyl ester ethyl ester (2a): To a solution of NaH (18.2 mmol) in 1,2-Dimethoxyethane (20 mL) was added dropwise a solution of ᵗButyl ethyl malonate (18.2 mmol) in DME (15 mL). The solution was agitated for 40 minutes after addition was complete. To the resulting slightly turbid solution was added a solution of 2,6-Dichloro-3-nitropyridine (7.23 mmol) in DME (15 mL). The resulting dark red solution was agitated at room temperature for 16 hours before dumping into water (25 mL) and acidifying with 6M HCl (aq.) to pH about 3. The yellow/clear solution was extracted with ether (2×) washed with brine, dried over MgSO₄ and concentrated in vacuo. The yellow oil consisted of 2a and 2b at a ratio of 1.7:1 and ᵗButyl ethyl malonate (40 wt %) by ¹H NMR. The oil was purified by flash chromatography (silica, 15% Ethyl acetate in Hexanes). Upon concentration an orange oil (2.82 g) was obtained with an isomeric ratio 2a:2b of 2.4:1 and 37 wt % malonate. The yield, corrected for excess malonate, was 71.3%. The material was carried on to the next step without further purification.

2-{6-[1-(2-Methoxy-ethyl)-piperidin-4-yloxy]-3-nitropyridin-2-yl}-malonic acid tert-butyl ester ethyl ester (3): To a solution of 1-(2-Methoxy-ethyl)-piperidin-4-ol (5.74 mmol) in THF (20 mL) was added NaH (11.6 mmol). Note: excess NaH was added due to excess ᵗButyl ethyl malonate carried over from 2a. The solution was agitated for 10 minutes. A solution of 2a/2b/malonate (5.15 mmol, corrected for assay) in THF (20 mL) was rapidly added to the first solution. The resulting solution was agitated at 30° C. for 18 hours, then at 55° C. for 2 hours. After allowing to cool to room temperature, the solution was quenched with water (400 μL), dried over Na₂SO₄ and concentrated in vacuo yielding a yellow oil which was purified by flash chromatography (silica, Gradient system: 1. Ethyl acetate, 2. 10% Methanol in Ethyl acetate). Upon concentration a yellow oil 3 (1.096 g, 45.2% yield) with an isomeric ratio of 3.3:1 was obtained.

{3-Amino-6-[1-(2-methoxy-ethyl)-piperidin-4-yloxy]-pyridin-2-yl}-acetic acid ethyl ester (5): A mixture of 3 (0.856 mmol) in TFA (15 mL) was agitated at room temperature for 20 min. LCMS indicated a mixture of ~1:1 of the tButyl cleavage/decarboxylation to tButyl and Ethyl cleavage/decarboxylation. The TFA was removed in vacuo. The resulting oil was put up in ethyl acetate and washed with sodium bicarbonate (aq., satd.), brine then dried over MgSO₄ and concentrated in vacuo. The free based material (4) was dissolved in ethanol (20 mL) and hydrogenated in the presence of 10% Pd/C (30 mg) at 20 psi on the Parr shaker for 1 hour. The suspension was filtered over celite and concentrated in vacuo yielding an orange-yellow oil (253 mg, 87.4%).

5-[1-(2-Methoxy-ethyl)-piperidin-4-yloxy]-1,3-dihydro-pyrrolo[3,2-b]pyridin-2-one Hydrochloride (6): To a mixture of 5 (0.483 mmol) in ethanol (5 mL) was added 4M HCl/Dioxane (15 mL). The solution was agitated at room temperature for 18 hours. All components in reaction are extremely polar and elute with solvent front. By LCMS, 6 was the major observed ion. The crude material was concentrated and taken directly on to the next step without purification.

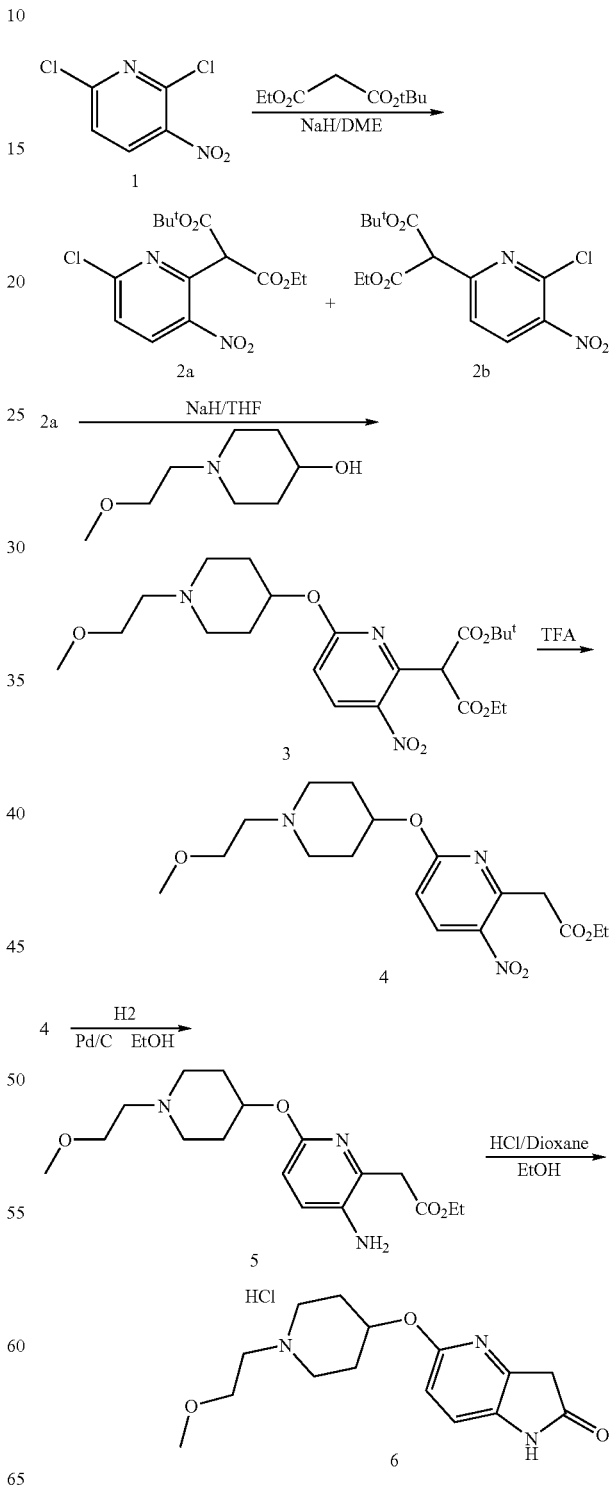

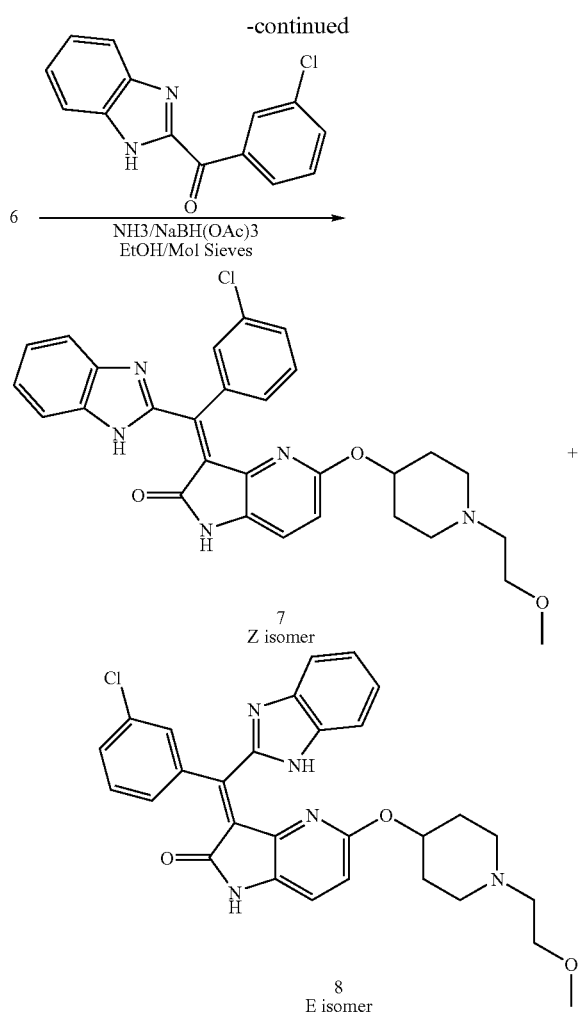

E- and Z-3-[(1H-Benzoimidazol-2-yl)-(3-chloro-phenyl)-methylene]-5-[1-(2-methoxy-ethyl)-piperidin-4-yloxy]-1,3-dihydro-pyrrolo[3,2-b]pyridin-2-one (7 and 8): A solution of 6 (0.515 mmol) and (1H-Benzoimidazol-2-yl)-(3-chloro-phenyl)-methanone (0.518 mmol) in ethanol (5mL, anhydrous) was placed in a sealed tube and cooled in an ice bath. The heterogeneous mixture was saturated with gaseous ammonia producing a homogeneous dark solution. The mixture was heated in the sealed tube to 95° C. for 16 hours. Both the E and Z isomers were observed at roughly a 1:1 ratio. The dark mixture was concentrated in vacuo, dissolved in methanol and the two isomers were isolated separately by preparative HPLC (Ammonium acetate/Acetonitrile system). The acetonitrile was removed in vacuo and the compounds were isolated by lyopholyzation. The isomers were isolated as the acetate salt. The more polar isomer (8) was isolated as a brown solid (56.2 mg, 20.7%). The less polar isomer (7) was also isolated as brown solid (67.0 mg, 24.6%).

Example 8

Synthesis of 7-[(1H-Benzoimidazol-2-yl)-(3-chloro-phenyl)-methylene]-2-[1-(2-methoxy-ethyl)-piperidin-4-ylamino]-5,7-dihydro-pyrrolo[3,2-d]pyrimidin-6-one (10)

2-(2-Chloro-5-nitro-pyrimidin-4-yl)-malonic acid tert-butyl ester ethyl ester (3). NaH (60%, 1.01 g, 25 mmol) was suspended in dry TBF (10 mls) to which was added tert-butyl ethyl malonate (2, 4.4 g, 23 mmol) in dry THF (10 mls) dropwise with stirring. The mixture was stirred at room temperature for 30-60 min. 2,4-dichloro-5-nitropyrimidine (1, 2.2 g, 11 mmol) in dry THF (10 mls) was added and the mixture stirred at room temperature overnight. The reaction mixture was diluted with EtOAc and washed with 5% citric acid (3×), sat'd NaCl (1×), dried (Na₂SO₄) and concentrated in vacuo to give 6.3 g of an approximately 1:1 mixture of 2-(2-Chloro-5-nitro-pyrimidin-4-yl)-malonic acid tert-butyl ester ethyl ester (3) and tert-butyl ethyl malonate (2) (~94% yield of 3) which was used as is in the next reaction without further purification. LC/MS Calcd for [M−H]⁻ 344, found 344.

2-{2-[1-(2-Methoxy-ethyl)-piperidin-4-ylamino]-5-nitro-pyrimidin-4-yl}-malonic acid tert-butyl ester ethyl ester (5). To 1-(2-methoxy-ethyl)-piperidin-4-ylamine (4, 1.7 g, 11 mmol) in EtOH (20 mls) was added a solution of the 1:1 mixture of 2-(2-chloro-5-nitro-pyrimidin-4-yl)-malonic acid tert-butyl ester ethyl ester (3) and tert-butyl ethyl malonate (2) (~5.3 mmol of 3) in EtOH (20 mls) dropwise with stirring. The resulting mixture was stirred at room temperature overnight and then diluted with EtOAc, washed with H₂O (1×), sat'd NaCl (1×), dried (Na₂SO₄), and concentrated in vacuo. The resulting residue was purified by flash chromatography (eluting solvents=CH₂Cl₂, followed by 2% MeOH in CH₂Cl₂, followed by 4% MeOH in CH₂Cl₂) to give 2-{2-[1-(2-methoxy-ethyl)-piperidin-4-ylamino]-5-nitro-pyrimidin-4-yl}-malonic acid tert-butyl ester ethyl ester (5, 733 mgs, 29%). LC/MS Calcd for [M+H]⁺ 468, found 468.

2-{5-Amino-2-[1-(2-methoxy-ethyl)-piperidin-4-ylamino]-pyrimidin-4-yl}-malonic acid tert-butyl ester ethyl ester (6). 2-{2-[1-(2-Methoxy-ethyl)-piperidin-4-ylamino]-5-nitro-pyrimidin-4-yl}-malonic acid tert-butyl ester ethyl ester (5, 733 mgs, 1.6 mmol) was dissolved in a mixture of MeOH (15 mls) and EtOAc (5 mls) to which was added 10% Pd/C (137 mgs). The reaction mixture was stirred under an atmosphere of H₂ at room temperature and pressure for 2 hrs, filtered through Celite with thorough washing with MeOH and the filtrate concentrated in vacuo to give 2-{5-amino-2-[1-(2-methoxy-ethyl)-piperidin-4-ylamino]-pyrimidin-4-yl}-malonic acid tert-butyl ester ethyl ester (6, 677 mgs, 99%) which was used in the next reaction without further purification. LC/MS Calcd for [M+H]⁺ 438, found 438.

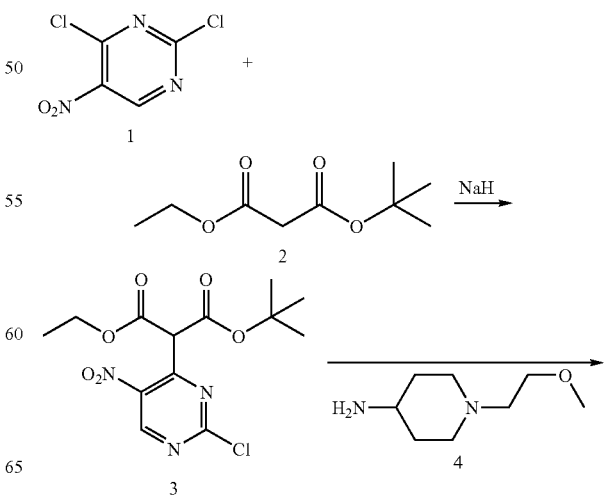

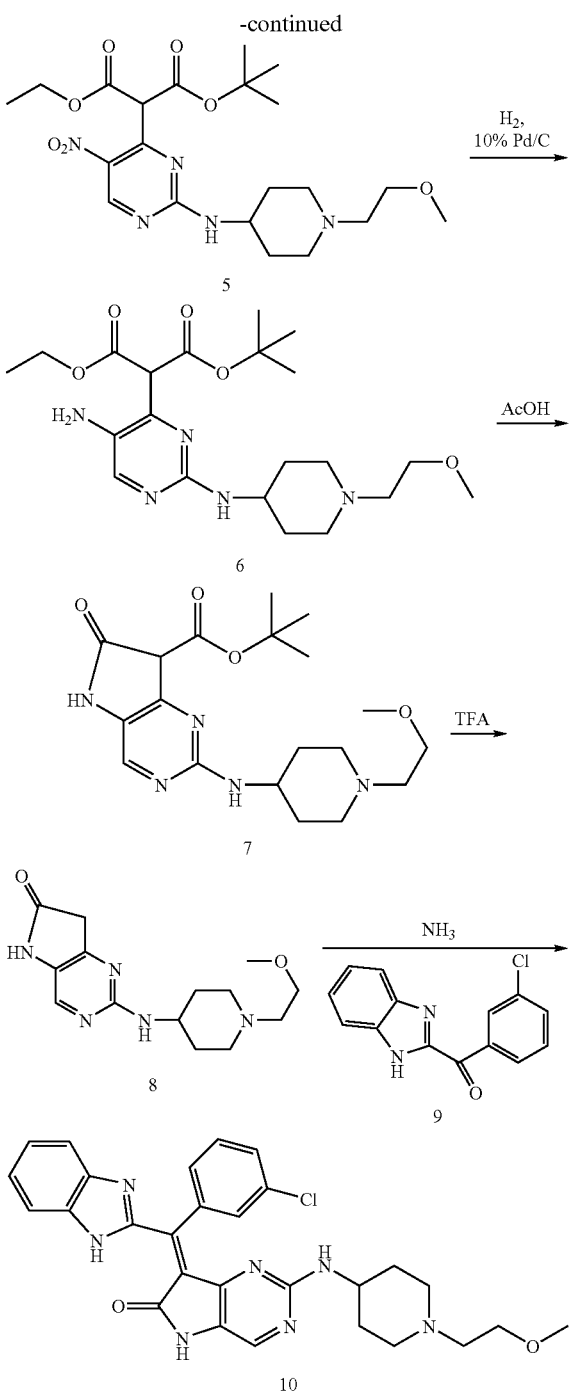

2-[1-(2-Methoxy-ethyl)-piperidin-4-ylamino]-6-oxo-6,7-dihydro-5H-pyrrolo[3,2-d]pyrimidine-7-carboxylic acid tert-butyl ester (7). 2-{5-Amino-2-[1-(2-methoxy-ethyl)-piperidin-4-ylamino]-pyrimidin-4-yl}-malonic acid tert-butyl ester ethyl ester (6, 658 mgs, 1.5 mmol) was dissolved in AcOH (8.0 mls) and stirred at room temperature for approximately 4 hrs. The reaction mixture was concentrated in vacuo and dried under high vacuum overnight to give 2-[1-(2-methoxy-ethyl)-piperidin-4-ylamino]-6-oxo-6,7-dihydro-5H-pyrrolo[3,2-d]pyrimidine-7-carboxylic acid tert-butyl ester (7, 785 mgs, ~100%) as a mixture of acetate salts which was used as is in the next reaction without further purification. LC/MS Calcd for [M+H]+ 392, found 392.

2-[1-(2-Methoxy-ethyl)-piperidin-4-ylamino]-5,7-dihydro-pyrrolo[3,2-d]pyrimidin-6-one (8). Crude 2-[1-(2-methoxy-ethyl)-piperidin-4-ylamino]-6-oxo-6,7-dihydro-5H-pyrrolo[3,2-d]pyrimidine-7-carboxylic acid tert-butyl ester, acetate salts (7, 785 mgs, ~1.5 mmol) was stirred in neat TFA for 30 min at room temperature. The reaction mixture was concentrated in vacuo. The resulting residue was suspended in toluene and reconcentrated in vacuo to remove residual TFA, then dried under high vacuum for several hours to give 2-[1-(2-methoxy-ethyl)-piperidin-4-ylamino]-5,7-dihydro-pyrrolo[3,2-d]pyrimidin-6-one (8, 1.1 g, ~1.5 mmol) as a mixture of TFA salts which was used in the next reaction without further purification. LC/MS Calcd for [M+H]+ 292, found 292.

7-[(1H-Benzoimidazol-2-yl)-(3-chloro-phenyl)-methylene]-2-[1-(2-methoxy-ethyl)-piperidin-4ylamino]-5,7-dihydro-pyrrolo[3,2-d]pyrimidin-6-one (10). A mixture of crude 2-[1-(2-methoxy-ethyl)-piperidin-4-ylamino]-5,7-dihydro-pyrrolo[3,2-d]pyrimidin-6-one, TFA salts (8, 519 mgs, 0.71 mmol) and (1H-benzoimidazol-2-yl)-(3-chloro-phenyl)-methanone (9, 192 mgs, 0.75 mmol) was dissolved in EtOH saturated with ammonia (8.0 mls) and the mixture stirred at 90 C in a sealed reaction vessel overnight. The reaction mixture was concentrated in vacuo and purified by preparative HPLC to give 7-[(1H-Benzoimidazol-2-yl)-(3-chloro-phenyl)-methylene]-2-[1-(2-methoxy-ethyl)-piperidin-4-ylamino]-5,7-dihydro-pyrrolo[3,2-d]pyrimidin-6-one (10). LC/MS Calcd for [M+H]+ 530, found 530.

Example 9

4-Boc-1-(2-methoxy-ethyl)-piperidin-4-ylamine (12). A mixture of 4-boc-aminopiperidine (11, 10.0 g, 50 mmol), potassium carbonate (6.5 g, 47 mmol), potassium iodide (7.7 g, 46 mmol), 2-bromoethyl methyl ether (4.4 mls, 46 mmol), and acetonitrile (100 mls) was heated to reflux for 3 hrs. After cooling to room temperature, the reaction mixture was poured into H2O and extracted with EtOAc (4x). The combined EtOAc extractions were washed with sat'd NaCl (1x), dried (Na2SO4), and concentrated in vacuo to give 4-boc-1-(2-methoxy-ethyl)-piperidin-4-ylamine (12, 12.0 g, 99%) which was used in the next reaction without further purification. LC/MS Calcd for [M+H]+ 259, found 259.

1-(2-Methoxy-ethyl)-piperidin-4-ylamine, di-TFA salt (13). 4-Boc-1-(2-methoxy-ethyl)-piperidin-4-ylamine (12, 12.0 g, 46 mmol) was dissolved in a 1:1 mixture of TFA and CH2Cl2 (80 mls) and stirred at room temperature for several hrs. The reaction mixture was concentrated in vacuo and the resulting oil redissolved/suspended in toluene and reconcentrated in vacuo repeatedly to remove excess TFA. The resulting oil was dried under high vacuum overnight to give 1-(2-methoxy-ethyl)-piperidin-4-ylamine, di-TFA salt (13, 18.6 g, 104%), which was used in the next step without further purification. LC/MS Calcd for [M+H]+ 159, found 159.

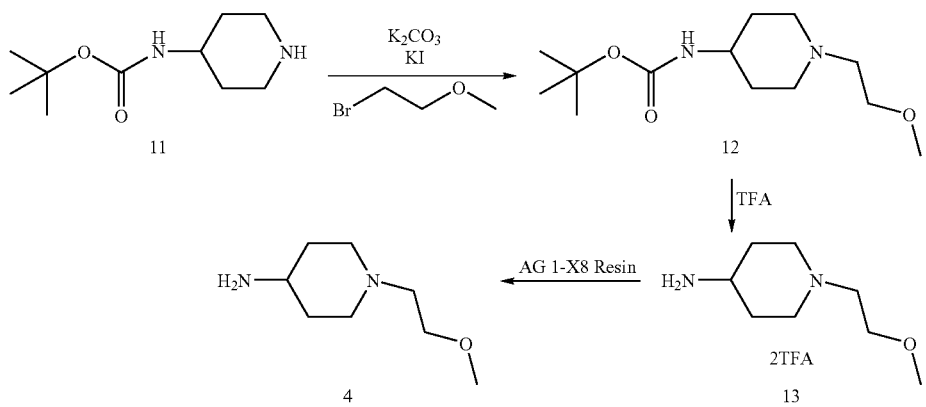

1-(2-Methoxy-ethyl)-piperidin-4-ylamine, free amine (4). A solution of 1-(2-methoxy-ethyl)-piperidin-4-ylamine, di-TFA salt (13, 3.5 g, 9.0 mmol) in MeOH was stirred in the presence of BIO-RAD AG 1-X8 resin, hydroxide form for several minutes. The resin was filtered, thoroughly washed with MeOH and the filtrate concentrated in vacuo. The resulting oil was dissolved in EtOAc, dried (Na$_2$SO$_4$), and concentrated in vacuo to give the free base of 1-(2-methoxy-ethyl)-piperidin-4-ylamine (4, ~9.0 mmol), which was used without further purification. LC/MS Calcd for [M+H]$^+$ 159, found 159.

Example 11

Synthesis of (3Z)-5-[(1-ethylpiperidin-4-yl)amino]-3-[(2-fluorophenyl)(4-methyl-1H-imidazol-2-yl)methylidene]-1,3-dihydro-2H-indol-2-one

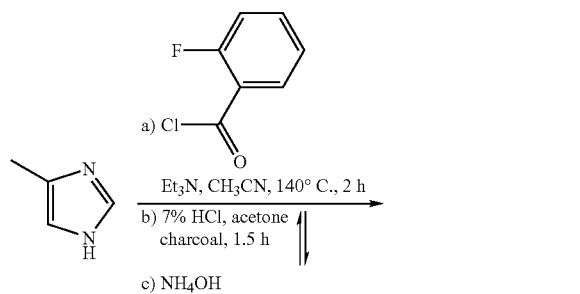

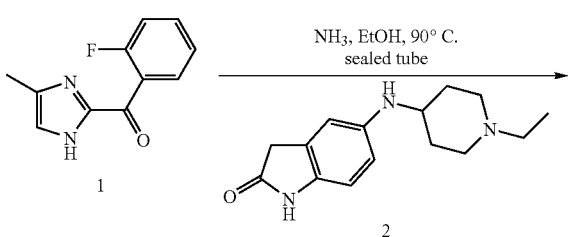

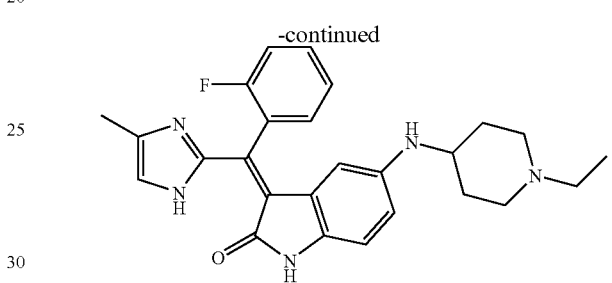

2-(2-Fluorobenzoyl)-4-methylimidazole (1). To a 350 mL pressure vessel was added 4-methylimidazole (12 g, 146 mmol, 1 eq.) and a stirbar. Acetonitrile (35 mL, 670 mmol, 4.6 eq.) was added. Triethylamine (59 mL, 424 mmol, 2.9 eq.) was added and the mixture was stirred until it became homogeneous. 2-fluorobenzoyl chloride (67.2 g, 424 mmol, 2.9 eq.) was added. Upon addition of the acyl chloride, the mixture became warm and viscous. The vessel was sealed and heated at 140° C. for 2 h with stirring. During heating, the mixture turned black in color. The vessel was removed from the heat, allowed to cool, and its contents were diluted with acetone (50 mL). The mixture was stirred and transferred to a 2 L round-bottomed flask containing 7% aqueous HCl (1000 mL). Charcoal was added to the flask and the mixture was heated at reflux for 1.5 h. The mixture was allowed to cool almost to room temperature and then was filtered through a Celite pad followed by a rinse with 1N HCl (~100 mL). The filtrate was placed in an ice bath and was made alkaline with aqueous NH$_4$OH (35%) whereupon a solid precipitate formed. The solid was filtered and washed with copious amounts of dilute NH$_4$OH to remove triethylamine hydrochloride salts. The solid was collected and placed under high vacuum, yielding the desired ketone 1 as a brown solid (20.1 g, 67%). LC/MSD (HP Series 1100 MSD) Expected MW: 204.07, Observed M+H: 205.0, Retention time: 1.13. $^1$H NMR, CD$_3$OD, Varian 400 MHz δ 7.70 (t, 1H), 7.59 (m, 1H), 7.30 (t, 1H), 7.25-6.96 (m, 2H), 2.34 (s, 3H).

(3Z)-5-[(1-ethylpiperidin-4-yl)amino]-3-[(2-fluorophenyl)(4-methyl-1H-imidazol-2-yl)methylidene]-1,3-dihydro-2H-indol-2-one The following reaction was performed identically in two separate batches. To a 350 mL pressure vessel was added 5-(1-ethyl-piperidin-4-ylamino)-1,3-dihydro-indol-2-one (2) (10.00 g, 38.5 mmol, 1.0 eq.) and a stirbar. Anhydrous EtOH (75 mL) was added followed by acetic acid (2 mL, 34.7 mmol, 0.9 eq.) and the mixture was stirred at room temperature for 20 min. Upon achieving a homogeneous solution, 2-(2-fluorobenzoyl)-4-methylimidazole (1) (11.2 g, 54.8 mmol, 1.4 eq.) was added and the reaction vessel was cooled to 0° C. in an ice bath. NH$_3$ (g) was bubbled into the solution until saturation was achieved. The reaction vessel was sealed tightly and heated at 100° C. for three days with stirring. Soon after heating, the reaction mixture became dark in color. The reaction mixture was removed from heat, cooled to room temperature and concentrated. The crude materials from both reactions were combined and purified via flash chromatography (3%-15% MeOH/CH$_2$Cl$_2$ gradient) to give (3Z)-5-[(1-ethylpiperidin-4-yl)amino]-3-[(2-fluorophenyl)(4-methyl-1H-imidazol-2-yl)methylidene]-1,3-dihydro-2H-indol-2-one as a dark purple solid (23.3 g, 68%). LC/MSD (HP Series 1100 MSD) Expected MW: 445.23, Observed M+H: 446.1, retention time: 1.10. Analytical HPLC: >95% purity, retention time: 1.31 (8 minute run). $^1$H NMR, DMSO-d6, Varian 400 MHz δ 10.93 (m, 1H), 7.58 (m, 1H), 7.39-6.94 (m, 4H), 6.62-6.59 (dd, 1H), 6.45-6.43 (dd, 1H), 4.91-4.86 (m, 2H), 2.76 (m, 2H), 2.35-2.30 (m, 4H), 2.09 (s, 1H), 1.85 (t, 2H), 1.54 (m, 2H), 1.11 (m, 2H), 1.01 (td, 3H).

Example 12

(3Z)-5-[(1-ethylpiperidin-4-yl)amino]-3-[(3-fluorophenyl)(4-methyl-1H-imidazol-2-yl)methylidene]-1,3-dihydro-2H-indol-2-one acetone (250 mL). The mixture was stirred and transferred to a 2 L round-bottomed flask containing 7% aqueous HCl (1000 mL). Charcoal was added to the flask and the mixture was refluxed at 85° C. for 1 hour. The mixture was allowed to cool slightly and then was filtered through a Celite pad followed by a rinse with 1N HCl (~200 mL). The filtrate was made alkaline with NH$_4$OH whereupon a solid precipitate formed. The solid was filtered and washed with copious amounts of dilute NH$_4$OH to remove triethylamine hydrochloride salts. The solid was collected and placed under high vacuum, yielding ketone 3 as an off-white solid (30.0 g, 80%). LC/MSD (HP Series 1100 MSD) Expected MW: 204.07, Observed M+H: 205.0, Retention time: 1.48. Analytical HPLC: >95% purity, retention time: 3.00 (8 minute run) $^1$H NMR, DMSO-d6, Varian 400 MHz δ 13.10 (br s, 1H), 8.28 (m, 2H), 7.60 (m, 1H), 7.52 (m, 1H), 7.30-7.06 (d, 1H), 2.29 (s, 3H).

(3Z)-5-[(1-ethylpiperidin-4yl)amino]-3-[(3-fluorophenyl)(4-methyl-1H-imidazol-2-yl)methylidene]-1,3-dihydro-2H-indol-2-one To a 350 mL pressure vessel was added 5-(1-ethyl-piperidin-4-ylamino)-1,3-dihydro-indol-2-one (2) (10.00 g, 38.5 mmol, 1.0 eq.) and a stirbar. Anhydrous EtOH (90 mL) was added followed by acetic acid (2 mL, 34.7 mmol, 0.9 eq.) and the mixture was stirred at room temperature for 20 min. Upon achieving a homogeneous solution, 2-(3-fluorobenzoyl)-4-methylimidazole (3) (8.66 g, 42.4 mmol, 1.1 eq.) was added and the reaction vessel was cooled to 0° C. in

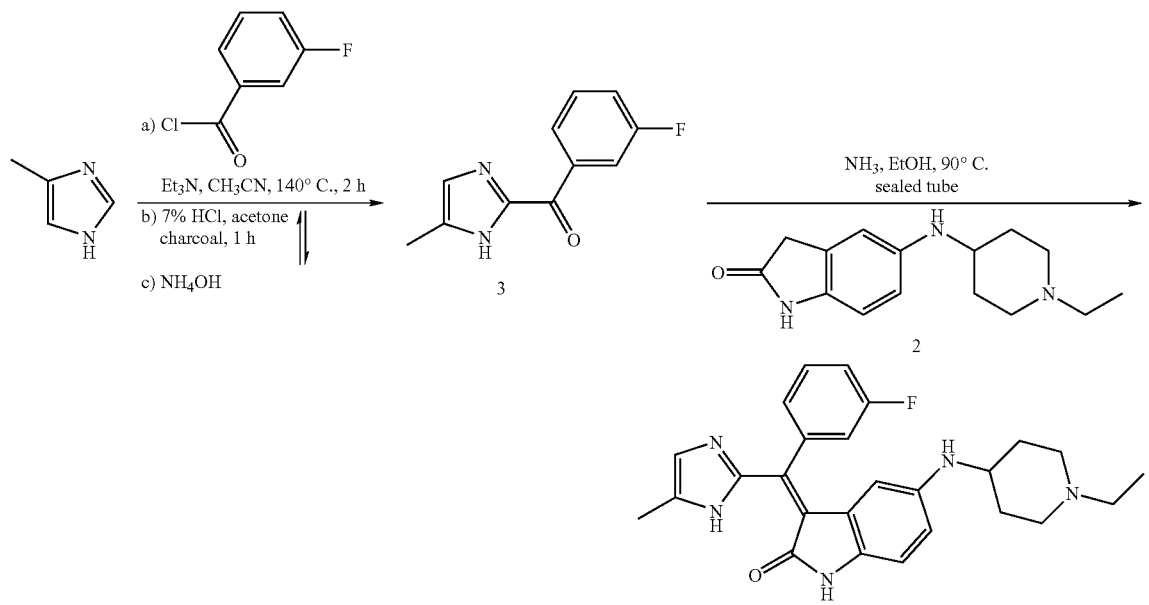

2-(3-Fluorobenzoyl)-4-methylimidazole (3). To a 350 mL pressure vessel was added 4-methylimidazole (17.85 g, 217 mmol, 1 eq.) and a stirbar. Acetonitrile (53 mL, 1022 mmol, 4.7 eq.) was added. Triethylamine (88 mL, 631 mmol, 2.9 eq.) was added and the mixture was stirred until it became homogeneous. 3-Fluorobenzoylchloride (100 g, 631 mmol, 2.9 eq.) was added. Upon addition of the acyl chloride, the mixture became warm and viscous. The vessel was sealed and heated at 140° C. for 2 hours with stirring. During heating, the mixture turned black in color. The vessel was removed from the heat, allowed to cool, and its contents were diluted with an ice bath. NH$_3$ (g) was bubbled into the solution until saturation was achieved. The reaction vessel was sealed tightly and heated at 100° C. overnight with stirring. Soon after heating, the reaction mixture became dark in color. The reaction mixture was removed from heat, cooled to room temperature and concentrated. The crude was purified via flash chromatography (3%-15% MeOH/CH$_2$Cl$_2$ gradient) to give (3Z)-5-[(1-ethylpiperidin-4-yl)amino]-3-[(3-fluorophenyl)(4-methyl-1H-imidazol-2-yl)methylidene]-1,3-dihydro-2H-indol-2-one as a dark purple solid (13.5 g, 79%). Analytical data for freebase: LC/MSD (HP Series 1100 MSD), Expected MW: 445.23, Observed M+H: 446.1, Retention time: 0.89. Analytical HPLC: >95% purity, retention time: 1.99 (8 minute run). $^1$H NMR, DMSO-d6, Varian 400 MHz δ 10.90 (m, 1H), 7.57 (m, 1H), 7.37-6.95 (m, 4H), 6.61-6.58 (dd, 1H), 6.44-6.41 (dd, 1H), 4.84-4.79 (m, 2H), 2.77 (m, 2H), 2.37-2.35 (m, 4H), 2.09 (s, 1H), 1.89 (m, 2H), 1.57-1.55 (m, 2H), 1.17-1.11 (m, 2H), 1.01 (t, 3H).

Assays

Kinase assays were performed by measurement of incorporation of γ-$^{33}$P ATP into immobilized myelin basic protein (MBP). High binding white 384 well plates (Greiner) were coated with MBP (Sigma #M-1891) by incubation of 60 ul/well of 20 μg/ml MBP in Tris-buffered saline (TBS; 50 mM Tris pH 8.0, 138 mM NaCl, 2.7 mM KCl) for 24 hours at 4° C. Plates were washed 3× with 100 μl TBS. Kinase reactions were carried out in a total volume of 34 μl in kinase buffer (5 mM Hepes pH 7.6, 15 mM NaCl, 0.01% bovine gamma globulin (Sigma #I-5506), 10 mM MgCl$_2$, 1 mM DTT, 0.02% TritonX-100). Compound dilutions were performed in DMSO and added to assay wells to a final DMSO concentration of 1%. Each data point was measured in duplicate, and at least two duplicate assays were performed for each individual compound determination. Enzyme was added to final concentrations of 10 nM or 20 nM, for example. A mixture of unlabeled ATP and γ-$^{33}$P ATP was added to start the reaction (2×10$^6$ cpm of γ-$^{33}$P ATP per well (3000 Ci/mmole) and either 10 μM or 30 μM unlabeled ATP, typically. The reactions were carried out for 1 hour at room temperature with shaking. Plates were washed 7× with TBS, followed by the addition of 50 μl/well scintillation fluid (Wallac). Plates were read using a Wallac Trilux counter. This is only one format of such assays, various other formats are possible, as known to one of ordinary skill in the art.

One measure of inhibition is $K_i$. For compounds with IC$_{50}$'s less than 1 μM, the $K_i$ or $K_d$ is defined as the dissociation rate constant for the interaction of the agent with, for example VEGF receptor 2 (Flk-1/KDR), FGFR1, or PDGFR (alpha and beta). Exemplary compositions have $K_i$'s of, for example, less than about 100 μM, less than about 10 μM, less than about 1 μM, and further for example having $K_i$'s of less than about 100 nM, and still further, for example, less than about 10 nM. The $K_i$ for a compound is determined from the IC$_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max}E_0\left[1 - \frac{(E_0 + I_0 + K_d) - \sqrt{(E_0 + I_0 + K_d)^2 - 4E_0 I_0}}{2E_0}\right]$$

where V is the observed rate, $V_{max}$ is the rate of the free enzyme, $I_0$ is the inhibitor concentration, $E_0$ is the enzyme concentration, and $K_d$ is the dissociation constant of the enzyme-inhibitor complex.

Another measure of inhibition is GI$_{50}$, defined as the concentration of the compound that results in a decrease in the rate of cell growth by fifty percent. Exemplary compounds have GI$_{50}$'s of, for example, less than about 1 mM, less than about 10 μM, less than about 1 μM, and further, for example, having GI$_{50}$'s of less than about 100 nM, still further having GI$_{50}$'s of less than about 10 nM. Measurement of GI$_{50}$ is done using a cell proliferation assay.

Tyrosine kinase activity is determined by 1) measurement of kinase-dependent ATP consumption by in the presence of a generic substrate such as, polyglutamic acid, tyrosine, 4:1 (pEY), by luciferase/luciferin-mediated chemiluminescence or; 2) incorporation of radioactive phosphate derived from $^{33}$P-ATP into a generic substrate which has been adsorbed onto the well surface of polystyrene microtiter plates. Phosphorylated substrate products are quantified by scintillation spectrometry.

Kinase Specificity Assays:

Kinase activity and compound inhibition are investigated using one or more assay formats. The ATP concentrations for each assay are selected to be close to the Michaelis-Menten constant ($K_M$) for each individual kinase. Dose-response experiments are performed at 10 different inhibitor concentrations in a 384-well plate format. The data are fitted to the following four-parameter equation:

$$Y=Min+(Max-Min)/(1+(X/IC_{50})^{\wedge}H)$$

where Y is the observed signal, X is the inhibitor concentration, Min is the background signal in the absence of enzyme (0% enzyme activity), Max is the signal in the absence of inhibitor (100% enzyme activity), IC$_{50}$ is the inhibitor concentration at 50% enzyme inhibition and H represents the empirical Hill's slope to measure the cooperativity. Typically H is close to unity. Exemplary kinase assays are described below.

KDR Assay

KDR biochemical activity was assessed using a Luciferase-Coupled Chemiluminescent Kinase assay (LCCA) format. Kinase activity was measured as the percent ATP remaining following the kinase reaction. Remaining ATP was detected by luciferase-luciferin-coupled chemiluminescence. Specifically, the reaction was initiated by mixing test compounds, 3 μM ATP, 1.6 μM poly-EY and 5 nM KDR (baculovirus expressed human KDR kinase domain D807-V1356) in a 20 uL assay buffer (20 mM Tris-HCL pH7.5, 10 mM MgCl$_2$, 0.01% Triton X-100, 1 mM DTT, 3 mM MnCl$_2$). The mixture is incubated at ambient temperature for 4 hours after which 20 uL luciferase-luciferin mix is added and the chemiluminescent signal read using a Wallac Victor$^2$ reader. The luciferase-luciferin mix consists of 50 mM HEPES, pH 7.8, 8.5 ug/mL oxalic acid (pH 7.8), 5 (or 50) mM DTT, 0.4% Triton X-100, 0.25 mg/niL coenzyme A, 63 uM AMP, 28 ug/mL luciferin and 40,000 units of light/mL luciferase.

c-Kit Assay c-Kit biochemical activity was assessed using AlphaScreen™ (Perkin Elmer) technology, described above. Test compounds, ATP, biotinylated poly(Glu, Tyr) and c-Kit kinase were combined in a volume of 20 μL in a 384-well white, medium binding microtiter plate (Greiner). Reaction mixtures were incubated for 1 hr at ambient temperature. Reactions were quenched by addition of 10 uL of 15-30 mg/mL AlphaScreen bead suspension containing 75 mM Hepes, pH 7.4, 300 mM NaCl, 120 mM EDTA, 0.3% BSA and 0.03% Tween-20. After 16 hr incubation at ambient temperature plates were read using an AlphaQuest reader (Perkin Elmer).

Structure Activity Relationships

Table 3 shows structure activity relationship data for selected compounds of the invention. Inhibition is indicated as $IC_{50}$ with the following key: A=$IC_{50}$ less than 50 nM, B=IC50 greater than 50 nM, but less than 500 nM, C=$IC_{50}$ greater than 500 nM, but less than 5,000 nM, and D=$IC_{50}$ greater than 5,000 nM.

Abbreviations for enzymes are known to one of ordinary skill in the art; for example, EphA2 refers to ephrin receptor tyrosine kinase family member ephrin A2; KDR, kinase insert domain receptor tyrosine kinase, and Flt-1, fms-like tyrosine kinase-1, are representative of the FLK family or receptor tyrosine kinases; EGFR, epidermal growth factor receptor tyrosine kinase; and ALK, Anaplastic Lymphoma Kinase.

TABLE 3

| Entry | Name | KDR | ALK | c-Kit | EGFR | EphA2 | FGFR1 | Flt1 | Flt3 | Fyn | IRK | PDGF-R-A |
|---|---|---|---|---|---|---|---|---|---|---|---|---|
| 1 | (3Z)-3-[[5-(methyloxy)-1H-benzimidazol-2-yl](phenyl)methylidene]-5-{[1-(phenylmethyl)pyrrolidin-3-yl]amino}-1,3-dihydro-2H-indol-2-one | A | | | C | C | | B | | B | D | B |
| 2 | (3Z)-5-[(1-ethylpiperidin-3-yl)amino]-3-[[5-(methyloxy)-1H-benzimidazol-2-yl](phenyl)methylidene]-1,3-dihydro-2H-indol-2-one | B | | | C | C | | C | | C | | B |
| 3 | (3Z)-5-[(1-ethylpiperidin-4-yl)amino]-3-[[5-(methyloxy)-1H-benzimidazol-2-yl](phenyl)methylidene]-1,3-dihydro-2H-indol-2-one | A | | B | B | C | B | B | A | A | C | A |
| 4 | (3Z)-5-[(1-ethylpiperidin-4-yl)amino]-3-[1H-imidazol-2-yl(phenyl)methylidene]-1,3-dihydro-2H-indol-2-one | A | | | C | C | | B | | A | C | A |
| 5 | (3Z)-5-[(1-ethylpiperidin-4-yl)amino]-3-{[5-(methyloxy)-1H-benzimidazol-2-yl][4-(methyloxy)phenyl]methylidene}-1,3-dihydro-2H-indol-2-one | A | | | C | D | | B | | A | C | A |
| 6 | (3Z)-5-[(1-ethylpiperidin-4-yl)amino]-3-[[5-(methyloxy)-1H-benzimidazol-2-yl](4-methylphenyl)methylidene]-1,3-dihydro-2H-indol-2-one | A | | | C | C | | B | | A | C | A |
| 7 | (3Z)-3-[1H-benzimidazol-2-yl(4-nitrophenyl)methylidene]-5-[(1-ethylpiperidin-4-yl)amino]-1,3-dihydro-2H-indol-2-one | A | | | C | D | | B | | B | D | A |
| 8 | (3Z)-3-{1H-benzimidazol-2-yl[4-(methyloxy)phenyl]methylidene}-5-[(1-ethylpiperidin-4-yl)amino]-1,3-dihydro-2H-indol-2-one | A | | | C | C | B | B | | A | D | A |
| 9 | (3Z)-3-[1H-benzimidazol-2-yl(phenyl)methylidene]-5-[(1-ethylpiperidin-4-yl)amino]-1,3-dihydro-2H-indol-2-one | A | A | B | C | A | B | | A | C | A |
| 10 | (3Z)-3-[[5-(methyloxy)-1H-benzimidazol-2-yl](phenyl)methylidene]-5-[(2,2,6,6-tetramethylpiperidin-4-yl)amino]-1,3-dihydro-2H-indol-2-one | C | | | C | C | | C | | C | C | B |
| 11 | (3Z)-3-[(4-aminophenyl)(1H-benzimidazol-2-yl)methylidene]-5-[(1-ethylpiperidin-4-yl)amino]-1,3-dihydro-2H-indol-2-one | A | | | B | C | | B | | A | C | A |
| 12 | (3Z)-3-[1H-benzimidazol-2-yl(4-methylphenyl)methylidene]-5-[(1-ethylpiperidin-4-yl)amino]-1,3-dihydro-2H-indol-2-one | A | | A | B | C | A | B | | A | C | A |
| 13 | (3Z)-5-[(1-ethylpiperidin-4-yl)amino]-3-[1H-imidazol-2-yl(4-methylphenyl)methylidene]-1,3-dihydro-2H-indol-2-one | A | | B | B | B | A | B | | A | C | A |
| 14 | (3Z)-5-[(1-ethylpiperidin-4-yl)oxy]-3-[[5-(methyloxy)-1H-benzimidazol-2-yl](phenyl)methylidene]-1,3-dihydro-2H-indol-2-one | A | | | C | C | | C | | A | C | A |
| 15 | (3Z)-5-[(1-ethylpiperidin-4-yl)amino]-3-{1H-imidazol-2-yl[4-(methyloxy)phenyl]methylidene}-1,3-dihydro-2H-indol-2-one | A | | | C | C | | B | | A | C | A |
| 16 | (3Z)-3-[1H-benzimidazol-2-yl(4-fluorophenyl)methylidene]-5-[(1-ethylpiperidin-4-yl)amino]-1,3-dihydro-2H-indol-2-one | A | | | C | C | | B | | B | C | A |
| 17 | (3Z)-3-[1H-benzimidazol-2-yl(3,5-difluorophenyl)methylidene]-5-[(1-ethylpiperidin-4-yl)amino]-1,3-dihydro-2H-indol-2-one | A | | B | C | A | B | | A | C | A |

TABLE 3-continued

| Entry | Name | KDR | ALK | c-Kit | EGFR | EphA2 | FGFR1 | Flt1 | Flt3 | Fyn | IRK | PDGF-R-A |
|---|---|---|---|---|---|---|---|---|---|---|---|---|
| 18 | (3Z)-3-[1H-benzimidazol-2-yl(3-fluorophenyl)methylidene]-5-[(1-ethylpiperidin-4-yl)amino]-1,3-dihydro-2H-indol-2-one | A | | | B | C | A | B | | A | C | A |
| 19 | (3Z)-3-[1H-benzimidazol-2-yl(3-nitrophenyl)methylidene]-5-[(1-ethylpiperidin-4-yl)amino]-1,3-dihydro-2H-indol-2-one | A | | | C | C | | B | | B | C | A |
| 20 | 3-((Z)-1H-benzimidazol-2-yl{5-[(1-ethylpiperidin-4-yl)amino]-2-oxo-1,2-dihydro-3H-indol-3-ylidene}methyl)benzonitrile | A | | | C | C | | C | | B | C | B |
| 21 | (3Z)-3-[(3-aminophenyl)(1H-benzimidazol-2-yl)methylidene]-5-[(1-ethylpiperidin-4-yl)amino]-1,3-dihydro-2H-indol-2-one | A | | | C | C | | B | | B | C | A |
| 22 | (3Z)-3-[1H-benzimidazol-2-yl(phenyl)methylidene]-5-(piperidin-4-ylamino)-1,3-dihydro-2H-indol-2-one | A | | | C | B | | B | | A | B | A |
| 23 | 3-((Z)-1H-benzimidazol-2-yl{5-[(1-ethylpiperidin-4-yl)amino]-2-oxo-1,2-dihydro-3H-indol-3-ylidene}methyl)benzenecarboximidamide | C | | | C | C | | C | | C | C | C |
| 24 | (3Z)-3-[1H-benzimidazol-2-yl(phenyl)methylidene]-5-({1-[2-(methyloxy)ethyl]piperidin-4-yl}amino)-1,3-dihydro-2H-indol-2-one | A | A | | B | C | A | B | | A | C | A |
| 25 | (3Z)-3-[1H-benzimidazol-2-yl(phenyl)methylidene]-5-[(2,2,6,6-tetramethylpiperidin-4-yl)amino]-1,3-dihydro-2H-indol-2-one | B | | | C | C | | C | | C | C | B |
| 26 | (3Z)-3-{1H-benzimidazol-2-yl[3-(methyloxy)phenyl]methylidene}-5-[(1-ethylpiperidin-4-yl)amino]-1,3-dihydro-2H-indol-2-one | A | | | B | C | A | A | | A | C | A |
| 27 | (3Z)-3-[1H-benzimidazol-2-yl(3-chlorophenyl)methylidene]-5-[(1-ethylpiperidin-4-yl)amino]-1,3-dihydro-2H-indol-2-one | A | | | B | B | A | A | | A | B | A |
| 28 | 2-(2-{2-[(Z)-{5-[(1-ethylpiperidin-4-yl)amino]-2-oxo-1,2-dihydro-3H-indol-3-ylidene}(phenyl)methyl]-1H-imidazol-4-yl}ethyl)-1H-isoindole-1,3(2H)-dione | A | | | C | C | | B | | B | C | A |
| 29 | (3Z)-3-[1H-benzimidazol-2-yl(phenyl)methylidene]-5-({1-[2-(dimethylamino)ethyl]piperidin-4-yl}amino)-1,3-dihydro-2H-indol-2-one | A | | | C | C | | C | | B | C | B |
| 30 | (3Z)-3-[1H-benzimidazol-2-yl(phenyl)methylidene]-5-{[1-(methylsulfonyl)piperidin-4-yl]amino}-1,3-dihydro-2H-indol-2-one | B | | | C | C | | C | | C | C | C |
| 31 | (3Z)-5-(8-azabicyclo[3.2.1]oct-3-ylamino)-3-[1H-benzimidazol-2-yl(phenyl)methylidene]-1,3-dihydro-2H-indol-2-one | B | | | C | C | | C | | B | C | B |
| 32 | (3Z)-3-{1H-benzimidazol-2-yl[3-(methyloxy)phenyl]methylidene}-5-[(1-ethylpiperidin-4-yl)oxy]-1,3-dihydro-2H-indol-2-one | A | | | C | C | | B | | A | C | A |
| 33 | (3Z)-3-[1H-benzimidazol-2-yl(3,5-difluorophenyl)methylidene]-5-[(1-ethylpiperidin-4-yl)oxy]-1,3-dihydro-2H-indol-2-one | A | | | C | C | B | B | | A | C | A |
| 34 | (3Z)-3-[1H-benzimidazol-2-yl(phenyl)methylidene]-5-{[1-(phenylmethyl)piperidin-4-yl]oxy}-1,3-dihydro-2H-indol-2-one | A | | | C | C | | C | | A | C | A |
| 35 | (3Z)-3-[1H-benzimidazol-2-yl(3-chlorophenyl)methylidene]-5-[(1-ethylpiperidin-4-yl)oxy]-1,3-dihydro-2H-indol-2-one | A | | | C | C | A | B | | A | C | A |
| 36 | (3Z)-3-[1H-benzimidazol-2-yl(3,5-difluorophenyl)methylidene]-5-({1-[2-(methyloxy)ethyl]piperidin-4-yl}oxy)-1,3-dihydro-2H-indol-2-one | A | | | C | C | B | C | | A | C | A |

TABLE 3-continued

| Entry | Name | KDR | ALK | c-Kit | EGFR | EphA2 | FGFR1 | Flt1 | Flt3 | Fyn | IRK | PDGF-R-A |
|---|---|---|---|---|---|---|---|---|---|---|---|---|
| 37 | (3Z)-3-[1H-benzimidazol-2-yl(3-chlorophenyl)methylidene]-5-({1-[2-(methyloxy)ethyl]piperidin-4-yl}oxy)-1,3-dihydro-2H-indol-2-one | A | | | B | C | B | C | | A | C | A |
| 38 | (3Z)-3-[1H-benzimidazol-2-yl(3-chlorophenyl)methylidene]-5-({1-[2-(methyloxy)ethyl]piperidin-4-yl}amino)-1,3-dihydro-2H-indol-2-one | A | | | C | C | A | B | | A | C | A |
| 39 | (3Z)-3-{1H-benzimidazol-2-yl[3-(methyloxy)phenyl]methylidene}-5-({1-[2-(methyloxy)ethyl]piperidin-4-yl}amino)-1,3-dihydro-2H-indol-2-one | A | | | C | C | A | B | | A | C | A |
| 40 | (3Z)-3-[(3-chlorophenyl)(1H-imidazol-2-yl)methylidene]-5-({1-[2-(methyloxy)ethyl]piperidin-4-yl}amino)-1,3-dihydro-2H-indol-2-one | A | | | C | C | A | B | | A | C | A |
| 41 | (3Z)-3-[(3-fluorophenyl)(1H-imidazol-2-yl)methylidene]-5-({1-[2-(methyloxy)ethyl]piperidin-4-yl}amino)-1,3-dihydro-2H-indol-2-one | A | | B | B | C | A | B | | A | C | A |
| 42 | (3Z)-3-[1H-benzimidazol-2-yl(3,5-difluorophenyl)methylidene]-5-({1-[2-(methyloxy)ethyl]piperidin-4-yl}amino)-1,3-dihydro-2H-indol-2-one | A | | | B | C | A | B | | A | D | A |
| 43 | (3Z)-3-[1H-benzimidazol-2-yl(3-chlorophenyl)methylidene]-5-[(1-ethylpiperidin-4-yl)(methyl)amino]-1,3-dihydro-2H-indol-2-one | A | | | C | C | B | C | | B | C | B |
| 44 | (3Z)-3-[(3-chlorophenyl)(1H-imidazol-2-yl)methylidene]-5-[(1-ethylpiperidin-4-yl)oxy]-1,3-dihydro-2H-indol-2-one | A | | | C | C | B | C | | B | C | B |
| 45 | (3Z)-3-[1H-benzimidazol-2-yl(4-chlorophenyl)methylidene]-5-[(1-ethylpiperidin-4-yl)amino]-1,3-dihydro-2H-indol-2-one | A | | | B | C | B | A | | A | C | A |
| 46 | (3Z)-3-[1H-benzimidazol-2-yl(3-fluorophenyl)methylidene]-5-({1-[2-(methyloxy)ethyl]piperidin-4-yl}amino)-1,3-dihydro-2H-indol-2-one | A | | | B | C | B | B | | A | C | A |
| 47 | (3Z)-3-[1H-benzimidazol-2-yl(4-fluorophenyl)methylidene]-5-({1-[2-(methyloxy)ethyl]piperidin-4-yl}amino)-1,3-dihydro-2H-indol-2-one | A | | | C | C | B | C | | B | C | A |
| 48 | (3Z)-3-[(3-chlorophenyl)(1H-imidazol-2-yl)methylidene]-5-[(1-ethylpiperidin-4-yl)amino]-1,3-dihydro-2H-indol-2-one | A | | | B | C | A | B | | A | D | A |
| 49 | (3Z)-5-[(1-ethylpiperidin-4-yl)amino]-3-[(3-fluorophenyl)(1H-imidazol-2-yl)methylidene]-1,3-dihydro-2H-indol-2-one | A | B | A | B | C | A | B | A | A | C | A |
| 50 | (3Z)-3-[1H-benzimidazol-2-yl(3-fluoro-4-methylphenyl)methylidene]-5-[(1-ethylpiperidin-4-yl)amino]-1,3-dihydro-2H-indol-2-one | A | | | A | C | A | A | | A | C | A |
| 51 | (3Z)-5-[(1-ethylpiperidin-4-yl)amino]-3-[(3-fluorophenyl)(4-methyl-1H-imidazol-2-yl)methylidene]-1,3-dihydro-2H-indol-2-one | A | A | A | A | C | A | B | A | A | C | A |
| 52 | (3Z)-3-[1H-benzimidazol-2-yl(4-fluoro-3-methylphenyl)methylidene]-5-[(1-ethylpiperidin-4-yl)amino]-1,3-dihydro-2H-indol-2-one | A | | | | C | B | | | A | C | A |
| 53 | (3Z)-3-[(3-chloro-4-fluorophenyl)(1H-imidazol-2-yl)methylidene]-5-[(1-ethylpiperidin-4-yl)amino]-1,3-dihydro-2H-indol-2-one | A | | A | C | C | A | | | A | D | A |
| 54 | (3Z)-3-[(3,4-difluorophenyl)(1H-imidazol-2-yl)methylidene]-5-[(1-ethylpiperidin-4-yl)amino]-1,3-dihydro-2H-indol-2-one | A | | B | C | C | A | | | A | D | A |
| 55 | (3Z)-3-[(5-chloro-1H-benzimidazol-2-yl)(phenyl)methylidene]-5-[(1-ethylperidin-4-yl)amino]-1,3-dihydro-2H-indol-2-one | A | | | | C | B | | | A | C | A |
| 56 | (3Z)-3-[(5-chloro-1H-benzimidazol-2-yl)(3,5-difluorophenyl)methylidene]-5-[(1-ethylpiperidin-4-yl)amino]-1,3-dihydro-2H-indol-2-one | A | | | | C | B | | | A | D | A |

TABLE 3-continued

| Entry | Name | KDR | ALK | c-Kit | EGFR | EphA2 | FGFR1 | Flt1 | Flt3 | Fyn | IRK | PDGF-R-A |
|---|---|---|---|---|---|---|---|---|---|---|---|---|
| 57 | (3Z)-5-[(1-ethylpiperidin-4-yl)amino]-3-[(3-fluoro-4-methylphenyl)(1H-imidazol-2-yl)methylidene]-1,3-dihydro-2H-indol-2-one | A | B | | | B | A | | | A | C | A |
| 58 | (3Z)-5-[(1-ethylpiperidin-4-yl)amino]-3-[(4-fluorophenyl)(1H-imidazol-2-yl)methylidene]-1,3-dihydro-2H-indol-2-one | A | B | A | C | C | A | | | A | D | A |
| 59 | (3Z)-5-[(1-ethylpiperidin-4-yl)amino]-3-[1H-imidazol-2-yl(4-propylphenyl)methylidene]-1,3-dihydro-2H-indol-2-one | A | | | B | C | A | | | A | C | A |
| 60 | (3Z)-5-[(1-ethylpiperidin-4-yl)amino]-3-{1H-imidazol-2-yl[4-(trifluoromethyl)phenyl]methylidene}-1,3-dihydro-2H-indol-2-one | A | | B | C | C | A | | | A | D | A |
| 61 | (3E)-3-[(3,5-difluorophenyl)(5-fluoro-1H-benzimidazol-2-yl)methylidene]-5-[(1-ethylpiperidin-4-yl)amino]-1,3-dihydro-2H-indol-2-one | A | | | D | D | B | | | A | D | A |
| 62 | (3Z)-3-[(3,5-difluorophenyl)(5-fluoro-1H-benzimidazol-2-yl)methylidene]-5-[(1-ethylpiperidin-4-yl)amino]-1,3-dihydro-2H-indol-2-one | A | | | B | C | A | | | A | D | A |
| 63 | (3Z)-3-[(3-fluoro-4-methylphenyl)(1H-imidazol-2-yl)methylidene]-5-({1-[2-(methyloxy)ethyl]piperidin-4-yl}amino)-1,3-dihydro-2H-indol-2-one | A | | | B | B | A | | | A | C | A |
| 64 | (3Z)-5-[(1-ethylpiperidin-4-yl)amino]-3-[(4-methyl-1H-imidazol-2-yl)(4-methylphenyl)methylidene]-1,3-dihydro-2H-indol-2-one | A | A | | B | B | A | | | A | C | A |
| 65 | (3Z)-5-[(1-ethylpiperidin-4-yl)amino]-3-[[3-fluoro-4-(trifluoromethyl)phenyl](1H-imidazol-2-yl)methylidene]-1,3-dihydro-2H-indol-2-one | A | | B | B | C | A | | | A | D | A |
| 66 | (3Z)-3-[(4-chlorophenyl)(1H-imidazol-2-yl)methylidene]-5-[(1-ethylpiperidin-4-yl)amino]-1,3-dihydro-2H-indol-2-one | A | | A | B | C | A | | A | A | C | A |
| 67 | (3Z)-5-[(1-ethylpiperidin-4-yl)amino]-3-[(3-fluoro-4-methylphenyl)(4-methyl-1H-imidazol-2-yl)methylidene]-1,3-dihydro-2H-indol-2-one | A | A | | A | B | A | | | A | C | A |
| 68 | (3Z)-5-[(1-ethylpiperidin-4-yl)amino]-3-{1H-imidazol-2-yl[6-(trifluoromethyl)pyridin-3-yl]methylidene}-1,3-dihydro-2H-indol-2-one | B | | | D | C | B | | | B | D | A |
| 69 | (3Z)-3-[1H-imidazol-2-yl(4-methylphenyl)methylidene]-5-({1-[2-(methyloxy)ethyl]piperidin-4-yl}amino)-1,3-dihydro-2H-indol-2-one | A | | | B | B | A | | | A | C | A |
| 70 | (3Z)-3-[(3-fluorophenyl)(4-methyl-1H-imidazol-2-yl)methylidene]-5-({1-[2-(methyloxy)ethyl]piperidin-4-yl}amino)-1,3-dihydro-2H-indol-2-one | A | | | B | B | A | | | A | C | A |
| 71 | (3Z)-3-{1H-imidazol-2-yl[4-(trifluoromethyl)phenyl]methylidene}-5-({1-[2-(methyloxy)ethyl]piperidin-4-yl}amino)-1,3-dihydro-2H-indol-2-one | A | | | D | C | A | | | B | D | A |
| 72 | (3Z)-3-[(5-chloro-1H-benzimidazol-2-yl)(phenyl)methylidene]-5-({1-[2-(methyloxy)ethyl]piperidin-4-yl}amino)-1,3-dihydro-2H-indol-2-one | A | | | D | C | A | | | B | D | A |
| 73 | (3Z)-3-[(3,5-difluorophenyl)(1H-imidazol-2-yl)methylidene]-5-[(1-ethylpiperidin-4-yl)amino]-1,3-dihydro-2H-indol-2-one | A | | B | B | C | A | | | A | D | A |
| 74 | (3Z)-3-[(3,5-difluorophenyl)(4-methyl-1H-imidazol-2-yl)methylidene]-5-[(1-ethylpiperidin-4-yl)amino]-1,3-dihydro-2H-indol-2-one | A | B | A | B | B | A | | A | A | C | A |
| 75 | (3Z)-3-[(3,5-difluorophenyl)(1H-imidazol-2-yl)methylidene]-5-({1-[2-(methyloxy)ethyl]piperidin-4-yl}amino)-1,3-dihydro-2H-indol-2-one | A | | | B | C | A | | | A | D | A |
| 76 | (3Z)-3-[(3,5-difluorophenyl)(4-methyl-1H-imidazol-2-yl)methylidene]-5-({1-[2-(methyloxy)ethyl]piperidin-4-yl}amino)-1,3-dihydro-2H-indol-2-one | A | | | B | C | A | | | A | C | A |

TABLE 3-continued

| Entry | Name | KDR | ALK | c-Kit | EGFR | EphA2 | FGFR1 | Flt1 | Flt3 | Fyn | IRK | PDGF-R-A |
|---|---|---|---|---|---|---|---|---|---|---|---|---|
| 77 | (3Z)-3-[(4-methyl-1H-imidazol-2-yl)(4-methylphenyl)methylidene]-5-({1-[2-(methyloxy)ethyl]piperidin-4-yl}amino)-1,3-dihydro-2H-indol-2-one | A | | | B | B | A | | | A | C | A |
| 78 | (3Z)-3-[(4-fluorophenyl)(1H-imidazol-2-yl)methylidene]-5-({1-[2-(methyloxy)ethyl]piperidin-4-yl}amino)-1,3-dihydro-2H-indol-2-one | A | | | D | C | B | | | B | D | A |
| 79 | (3Z)-3-[(3,4-difluorophenyl)(1H-imidazol-2-yl)methylidene]-5-({1-[2-(methyloxy)ethyl]piperidin-4-yl}amino)-1,3-dihydro-2H-indol-2-one | A | | | D | C | B | | | B | D | A |
| 80 | (3Z)-3-[(3-chloro-4-fluorophenyl)(1H-imidazol-2-yl)methylidene]-5-({1-[2-(methyloxy)ethyl]piperidin-4-yl}amino)-1,3-dihydro-2H-indol-2-one | A | | | D | C | B | | | B | D | B |
| 81 | (3Z)-3-[(3-fluorophenyl)(1H-imidazol-2-yl)methylidene]-5-(piperidin-4-ylamino)-1,3-dihydro-2H-indol-2-one | A | | | D | B | A | | | A | C | A |
| 82 | (3Z)-3-[(3-fluorophenyl)(1H-imidazol-2-yl)methylidene]-5-{[1-(2-piperidin-1-ylethyl)piperidin-4-yl]amino}-1,3-dihydro-2H-indol-2-one | B | | | D | C | B | | | B | D | B |
| 83 | (3Z)-3-[(3-fluorophenyl)(1H-imidazol-2-yl)methylidene]-5-{[1-(2-morpholin-4-ylethyl)piperidin-4-yl]amino}-1,3-dihydro-2H-indol-2-one | A | | | D | C | A | | | B | D | A |
| 84 | (3Z)-5-({1-[2-(diethylamino)ethyl]piperidin-4-yl}amino)-3-[(3-fluorophenyl)(1H-imidazol-2-yl)methylidene]-1,3-dihydro-2H-indol-2-one | B | | | D | C | B | | | B | D | B |
| 85 | (3Z)-3-[(3-fluorophenyl)(1H-imidazol-2-yl)methylidene]-5-{[1-(2-pyrrolidin-1-ylethyl)piperidin-4-yl]amino}-1,3-dihydro-2H-indol-2-one | A | | | D | C | B | | | B | D | A |
| 86 | (3Z)-3-[1H-imidazol-2-yl(4-methylphenyl)methylidene]-5-[(1-methylpiperidin-4-yl)amino]-1,3-dihydro-2H-indol-2-one | A | | | B | B | A | | | A | C | A |
| 87 | (3Z)-3-[(3-fluorophenyl)(1H-1,2,4-triazol-5-yl)methylidene]-5-({1-[2-(methyloxy)ethyl]piperidin-4-yl}amino)-1,3-dihydro-2H-indol-2-one | B | | | D | D | B | | | D | D | B |
| 88 | ethyl 2-{(Z)-(3-fluorophenyl)[5-({1-[2-(methyloxy)ethyl]piperidin-4-yl}amino)-2-oxo-1,2-dihydro-3H-indol-3-ylidene]methyl}-4-methyl-1H-imidazol-5-yl}ethyl)-1H-isoindole-1,3(2H)-dione | B | | | D | D | B | | | B | D | A |
| 89 | (3Z)-3-[1H-imidazol-2-yl(phenyl)methylidene]-5-({1-[2-(methyloxy)ethyl]piperidin-4-yl}amino)-1,3-dihydro-2H-indol-2-one | A | | | D | C | A | | | A | C | A |
| 90 | (3Z)-3-{1H-imidazol-2-yl[4-(methyloxy)phenyl]methylidene}-5-({1-[2-(methyloxy)ethyl]piperidin-4-yl}amino)-1,3-dihydro-2H-indol-2-one | A | | | D | C | B | | | A | D | A |
| 91 | (3Z)-3-[(4-chlorophenyl)(1H-imidazol-2-yl)methylidene]-5-({1-[2-(methyloxy)ethyl]piperidin-4-yl}amino)-1,3-dihydro-2H-indol-2-one | A | | | D | C | A | | | A | C | A |
| 92 | (3Z)-3-[[3-fluoro-4-(trifluoromethyl)phenyl](1H-imidazol-2-yl)methylidene]-5-({1-[2-(methyloxy)ethyl]piperidin-4-yl}amino)-1,3-dihydro-2H-indol-2-one | A | | | D | C | B | | | B | D | A |
| 93 | (3Z)-3-[(3-fluorophenyl)(1H-imidazol-2-yl)methylidene]-5-{[1-(methylsulfonyl)piperidin-4-yl]amino}-1,3-dihydro-2H-indol-2-one | B | | | D | D | B | | | D | C | |
| 94 | (3Z)-3-[1H-imidazol-2-yl(4-propylphenyl)methylidene]-5-({1-[2-(methyloxy)ethyl]piperidin-4-yl}amino)-1,3-dihydro-2H-indol-2-one | A | | | B | C | A | | | A | C | |
| 95 | (3Z)-5-[(1-ethylpiperidin-4-yl)amino]-3-[(3-fluorophenyl)(4-phenyl-1H-imidazol-2-yl)methylidene]-1,3-dihydro-2H-indol-2-one | A | | | B | C | A | | | A | C | |

TABLE 3-continued

| Entry | Name | KDR | ALK | c-Kit | EGFR | EphA2 | FGFR1 | Flt1 | Flt3 | Fyn | IRK | PDGF-R-A |
|---|---|---|---|---|---|---|---|---|---|---|---|---|
| 96 | (3Z)-3-[(3-fluorophenyl)(4-phenyl-1H-imidazol-2-yl)methylidene]-5-({1-[2-(methyloxy)ethyl]piperidin-4-yl}amino)-1,3-dihydro-2H-indol-2-one | A | | | B | C | A | | | A | C | |
| 97 | (3Z)-3-[(3-fluoro-4-methylphenyl)(4-methyl-1H-imidazol-2-yl)methylidene]-5-({1-[2-(methyloxy)ethyl]piperidin-4-yl}amino)-1,3-dihydro-2H-indol-2-one | A | A | | A | C | A | | | A | C | |
| 98 | (3Z)-3-{1H-imidazol-2-yl[6-(trifluoromethyl)pyridin-3-yl]methylidene}-5-({1-[2-(methyloxy)ethyl]piperidin-4-yl}amino)-1,3-dihydro-2H-indol-2-one | B | | | D | C | B | | | B | D | |
| 99 | (3Z)-5-[(1-ethylpiperidin-4-yl)amino]-3-[(3-fluorophenyl)(1H-1,2,4-triazol-5-yl)methylidene]-1,3-dihydro-2H-indol-2-one | B | | | D | D | B | | | D | D | |
| 100 | (3Z)-5-[(1-ethylpiperidin-4-yl)amino]-3-[[2-fluoro-4-(trifluoromethyl)phenyl](1H-imidazol-2-yl)methylidene]-1,3-dihydro-2H-indol-2-one | A | | A | B | C | A | | | A | C | A |
| 101 | (3Z)-5-[(1-ethylpiperidin-4-yl)amino]-3-{(4-methyl-1H-imidazol-2-yl)[4-(trifluoromethyl)phenyl]methylidene}-1,3-dihydro-2H-indol-2-one | A | | B | B | C | A | | | A | C | A |
| 102 | (3Z)-3-[(4-chlorophenyl)(4-methyl-1H-imidazol-2-yl)methylidene]-5-[(1-ethylpiperidin-4-yl)amino]-1,3-dihydro-2H-indol-2-one | A | A | A | B | C | A | | | A | C | A |
| 103 | (3Z)-5-[(1-ethylpiperidin-4-yl)amino]-3-[[3-fluoro-4-(trifluoromethyl)phenyl](4-methyl-1H-imidazol-2-yl)methylidene]-1,3-dihydro-2H-indol-2-one | A | | B | A | C | A | | | A | C | |
| 104 | (3Z)-3-[(3,4-difluorophenyl)(4-methyl-1H-imidazol-2-yl)methylidene]-5-[(1-ethylpiperidin-4-yl)amino]-1,3-dihydro-2H-indol-2-one | A | | B | A | C | A | | | A | D | A |
| 105 | (3Z)-3-[(3-chloro-4-fluorophenyl)(4-methyl-1H-imidazol-2-yl)methylidene]-5-[(1-ethylpiperidin-4-yl)amino]-1,3-dihydro-2H-indol-2-one | A | | B | B | C | A | | | A | C | A |
| 106 | (3Z)-5-[(1-ethylpiperidin-4-yl)amino]-3-[(4-fluorophenyl)(4-methyl-1H-imidazol-2-yl)methylidene]-1,3-dihydro-2H-indol-2-one | A | | B | B | C | B | | | A | C | A |
| 107 | (3Z)-5-[(1-ethylpiperidin-4-yl)amino]-3-[(2-fluorophenyl)(1H-imidazol-2-yl)methylidene]-1,3-dihydro-2H-indol-2-one | A | | A | B | C | A | | | A | C | A |
| 108 | (3Z)-5-[(1-ethylpiperidin-4-yl)amino]-3-[[2-fluoro-4-(trifluoromethyl)phenyl](4-methyl-1H-imidazol-2-yl)methylidene]-1,3-dihydro-2H-indol-2-one | A | | A | B | C | A | | | A | C | A |
| 109 | (3Z)-3-[(2,3-difluorophenyl)(1H-imidazol-2-yl)methylidene]-5-[(1-ethylpiperidin-4-yl)amino]-1,3-dihydro-2H-indol-2-one | A | | A | B | C | A | | | A | C | A |
| 110 | (3Z)-3-[(2,3-difluorophenyl)(4-methyl-1H-imidazol-2-yl)methylidene]-5-[(1-ethylpiperidin-4-yl)amino]-1,3-dihydro-2H-indol-2-one | A | A | A | B | C | A | | | A | C | A |
| 111 | (3Z)-3-[(2,4-difluorophenyl)(4-methyl-1H-imidazol-2-yl)methylidene]-5-[(1-ethylpiperidin-4-yl)amino]-1,3-dihydro-2H-indol-2-one | A | B | A | B | C | B | | | A | C | A |
| 112 | (3Z)-3-[(2,4-difluorophenyl)(1H-imidazol-2-yl)methylidene]-5-[(1-ethylpiperidin-4-yl)amino]-1,3-dihydro-2H-indol-2-one | A | | A | B | C | A | | | A | C | A |
| 113 | (3Z)-5-[(1-ethylpiperidin-4-yl)amino]-3-[(2-fluorophenyl)(1H-imidazol-2-yl)methylidene]-1,3-dihydro-2H-indol-2-one | A | B | A | A | C | A | | A | A | C | A |
| 114 | (3Z)-3-[(3-trifluoromethylphenyl)(1H-imidazol-2-yl)methylidene]-5-[(1-ethylpiperidin-4-yl)amino]-1,3-dihydro-2H-indol-2-one | A | | B | C | C | B | | | B | D | A |

TABLE 3-continued

| Entry | Name | KDR | ALK | c-Kit | EGFR | EphA2 | FGFR1 | Flt1 | Flt3 | Fyn | IRK | PDGF-R-A |
|---|---|---|---|---|---|---|---|---|---|---|---|---|
| 115 | (3Z)-3-[(3-trifluoromethylphenyl)(4-methyl-1H-imidazol-2-yl)methylidene]-5-[(1-ethylpiperidin-4-yl)amino]-1,3-dihydro-2H-indol-2-one | A | | A | C | C | B | | | B | C | A |
| 116 | (3Z)-3-[(2,4-dichloro-5-fluorophenyl)(1H-imidazol-2-yl)methylidene]-5-[(1-ethylpiperidin-4-yl)amino]-1,3-dihydro-2H-indol-2-one | A | | A | B | C | A | | A | A | C | A |
| 117 | (3Z)-3-[(2,4-dichloro-5-fluorophenyl)(4-methyl-1H-imidazol-2-yl)methylidene]-5-[(1-ethylpiperidin-4-yl)amino]-2H-indol-2-one | A | | A | B | C | A | | A | A | C | A |
| 118 | (3Z)-3-[(4-chloro-2-fluorophenyl)(4-methyl-1H-imidazol-2-yl)methylidene]-5-[(1-ethylpiperidin-4-yl)amino]-1,3-dihydro-2H-indol-2-one | A | A | A | A | C | A | | | A | B | |

What is claimed is:

1. A compound represented by formula I,

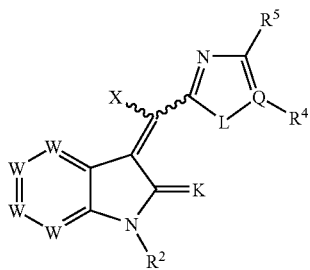

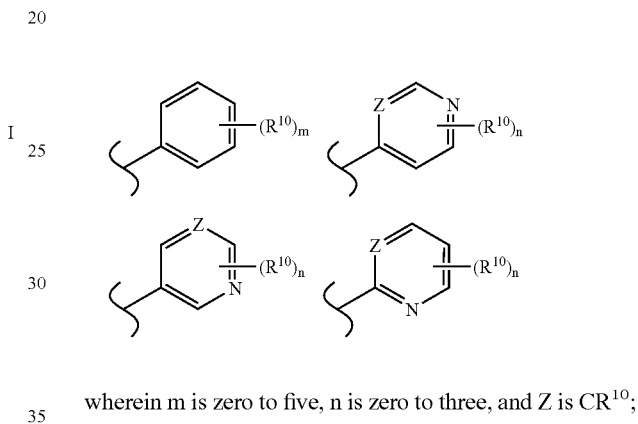

or a single stereoisomer, a single geometric isomer, a mixture of enantiomers, or a mixture of diastereomers thereof; and where the compound is optionally as a pharmaceutically acceptable salt thereof, and wherein, each W is $CR^1$;
each $R^1$ is independently selected from —H and —A—$R^7$; provided one of $R^1$ is —A—$R^7$ and is located at the 5-position of the indolinone ring, wherein, only for said —A—$R^7$, $R^7$ must be a piperidin-4-yl, and where the nitrogen of the piperidin-4-yl of —A—$R^7$ is optionally substituted with one group selected from alkyl, arylalkyl, pyrrolidinylethyl, piperidinylethyl, morpholinylethyl, and sulfonyl;
A is NH;
L is $NR^3$;
Q is C;
$R^2$ and $R^3$ are each —H;
$R^4$ and $R^5$ are each independently selected from —H, —$OR^6$, —$NR^6R^7$, —$S(O)_{0-2}R^6$, —$SO_2NR^6R^7$, —$CO_2R^6$, —$C(O)NR^6R^7$, —$N(R^6)SO_2R^6$, —$C(O)R^7$, —CN, —$NO_2$, —$NH_2$, halogen, trihalomethyl, alkyl, 1,3-dioxo-isoindol-2-ylethyl, and aryl; or
$R^4$ and $R^5$, when taken together, form a six-membered aromatic ring system containing zero nitrogens, said six-membered aromatic ring system is optionally substituted with between zero and four of $R^{15}$;
$R^6$ is selected from —H, and $C_{1-8}$alkyl;
$R^7$, for other than $R^7$ in —A—$R^7$, is selected from —H, and $C_{1-8}$alkyl;
$R^8$ is —H, —$NO_2$, —CN, —$OR^6$ or $C_{1-8}$alkyl;
X is selected from one of the following formulae:

wherein m is zero to five, n is zero to three, and Z is $CR^{10}$;
$R^{10}$ is selected from —H, halogen, trihalomethyl, —$NH_2$, —$NO_2$, —$OR^6$, —N=$CNR^6R^7$, —$NR^6R^7$, —$N(R^6)C(=NR^8)NR^6R^7$, —$SR^6$, —$S(O)_{1-2}R^6$, —$SO_2NR^6R^7$, —$CO_2R^6$, —$C(O)NR^6R^7$, —$C(O)N(OR^6)R^7$, —$C(=NR^8)NR^6R^7$, —$N(R^6)SO_2R^6$, —$C(O)R^7$, and $R^7$;
K is O; and
each $R^{15}$ is independently selected from —H, halogen, —$OR^6$, and $C_{1-8}$alkyl.

2. The compound according to claim 1, wherein X is

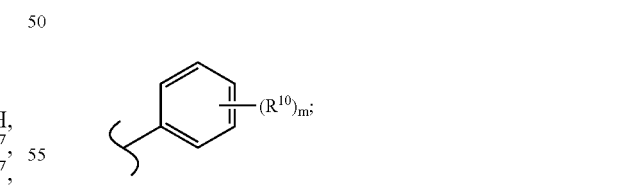

m is 0 to 3, and $R^{10}$ is selected from —H, halogen, —$NH_2$, —$NO_2$, $OR^6$, —N=$CNR^6R^7$, —$NR^6R^7$, —$N(R^6)C(=NR^8)NR^6R^7$, —$SR^6$, —$S(O)_{1-2}R^6$, —$SO_2NR^6R^7$, —$CO_2R^6$, —$C(O)NR^6R^7$, —$C(O)N(OR^6)R^7$, —$C(=NR^8)NR^6R^7$, —$N(R^6)SO_2R^6$, —$C(O)R^7$, and —$C_{1-8}$alkyl; or a single stereoisomer, a single geometric isomer, a mixture of enantiomers, or a mixture of diastereomers thereof; and where the compound is optionally as a pharmaceutically acceptable salt thereof.

3. A compound of formula II:

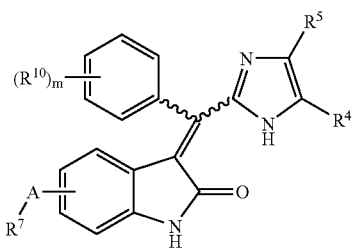

or a single stereoisomer, a single geometric isomer, a mixture of enantiomers, or a mixture of diastereomers thereof and where the compound is optionally as a pharmaceutically acceptable salt thereof;

wherein:

A is NH;

$R^7$, in —A—$R^7$, is piperidin-4-yl and is located on the 5-position of the indolinone ring;

wherein the ring nitrogen of $R^7$ is substituted with a group $R^{12}$; and $R^{12}$ is selected from a) —H, b) $C_{1-8}$alkyl, c) —SO$_2R^6$, d) —SO$_2$NR$^6R^7$, e) —CO$_2R^6$, f) —C(O)NR$^6R^7$, and g) —C(O)R$^7$; and where the $C_{1-8}$alkyl in b) is optionally substituted with one to five groups independently selected from alkyl, aryl, arylalkyl, pyrrolidinylethyl, piperidinylethyl, morpholinylethyl, alkoxy, amino, alkylamino and dialkylamino;

$R^6$ is selected from —H and $C_{1-8}$alkyl;

$R^4$ and $R^5$ are each independently selected from —H, —OR$^6$, —NR$^6R^7$, —S(O)$_{0-2}R^6$, —SO$_2$NR$^6R^7$, —CO$_2R^6$, —C(O)NR$^6R^7$, —N(R$^6$)SO$_2R^6$, —C(O)R$^7$, —CN, —NO$_2$, —NH$_2$, halogen, trihalomethyl, alkyl, 1,3-dioxo-isoindol-2-ylethyl, and aryl; or $R^4$ and $R^5$, when taken together, form a six-membered aromatic ring system containing zero nitrogens, said six-membered aromatic ring system is optionally substituted with between zero and four of $R^{15}$;

$R^{10}$ is selected from —H, halogen, —NH$_2$, —NO$_2$, —OR$^6$, —N=CNR$^6R^7$, —NR$^6R^7$, —N(R$^6$)C(=NR$^8$)NR$^6R^7$, —SR$^6$, —S(O)$_{1-2}R^6$, —SO$_2$NR$^6R^7$, —CO$_2R^6$, —C(O)NR$^6R^7$, —C(O)N(OR$^6$)R$^7$, —C(=NR$^8$)NR$^6R^7$, —N(R$^6$)SO$_2R^6$, —C(O)R$^7$, and $C_{1-8}$alkyl;

m is 0 to 3;

$R^7$, for other than $R^7$ in A—$R^7$, is selected from —H, and $C_{1-8}$alkyl;

$R^8$ is —H, —NO$_2$, —CN, —OR$^6$ or $C_{1-8}$alkyl; and each $R^{15}$ is independently selected from —H, halogen, —OR$^6$, and $C_{1-8}$alkyl.

4. A compound according to formula III,

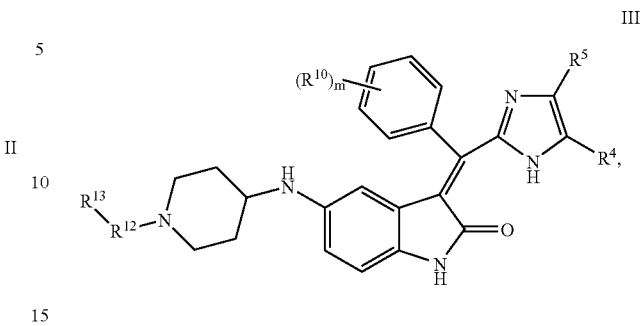

or a single stereoisomer, a single geometric isomer, a mixture of enantiomers, or a mixture of diastereomers thereof; and where the compound is optionally as a pharmaceutically acceptable salt thereof;

where $R^{12}$ is a $C_{1-4}$alkylene;

$R^{13}$ is selected from —H, an alkoxy group, amino, alkylamino, dialkylamino, pyrrolidinylethyl, piperidinylethyl, and morpholinylethyl, and an heteroalicyclic, with the proviso that a heteroatom of said alkoxy group, amino group, alkylamino group, and dialkylamino group cannot be attached to a carbon of $R^{12}$ which is directly attached to the ring nitrogen of the piperidine in formula III;

$R^4$ and $R^5$ are each independently selected from —H, —OR$^6$, —NR$^6R^7$, —S(O)$_{0-2}R^6$, —SO$_2$NR$^6R^7$, —CO$_2R^6$, —C(O)NR$^6R^7$, —N(R$^6$)SO$_2R^6$, —C(O)R$^7$, —CN, —NO$_2$, —NH$_2$, halogen, trihalomethyl, alkyl, 1,3-dioxo-isoindol-2-ylethyl, and aryl; or $R^4$ and $R^5$, when taken together, form a six-membered aromatic ring system containing zero nitrogens, said six-membered aromatic ring system is optionally substituted with between zero and four of $R^{15}$;

$R^6$ is selected from —H and $C_{1-8}$alkyl;

$R^7$ is selected from —H, and $C_{1-8}$alkyl;

$R^8$ is —H, —NO$_2$, —CN, —OR$^6$, or $C_{1-8}$alkyl;

$R^{10}$ is selected from —H, halogen, —NH$_2$, —NO$_2$, —OR$^6$, —N=CNR$^6R^7$, —NR$^6R^7$, —N(R$^6$)C(=NR$^8$)NR$^6R^7$, —SR$^6$, —S(O)$_{1-2}R^6$, —SO$_2$NR$^6R^7$, —CO$_2R^6$, —C(O)NR$^6R^7$, —C(O)N(OR$^6$)R$^7$, —C(=NR$^8$)NR$^6R^7$, —N(R$^6$)SO$_2R^6$, —C(O)R$^7$, and $C_{1-8}$alkyl;

m is 0 to 3; and each $R^{15}$ is independently selected from —H, halogen, —OR$^6$, and $C_{1-8}$alkyl.

5. A compound according to formula IIIa,

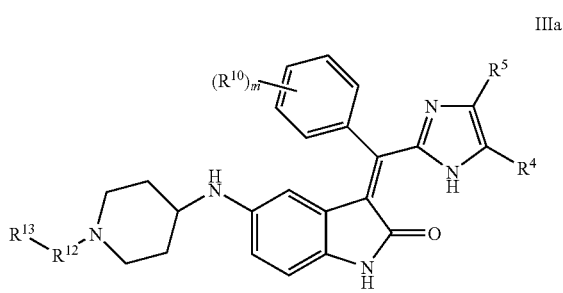

or a single stereoisomer, a single geometric isomer, a mixture of enantiomers, or a mixture of diastereomers thereof; and where the compound is optionally as a pharmaceutically acceptable salt thereof;

wherein $R^{12}$ is a $C_{2-4}$alkylene;

$R^{13}$ is selected from —H, an alkoxy group, an amino group, an alkylamino group, a dialkylamino group pyrrolidinylethyl, piperidinylethyl, and morpholinylethyl;

$R^{10}$ is selected from —H, halogen, perfluoroalkyl, —NH$_2$, —NO$_2$, —OR$^6$, —N═CNR$^6$R$^7$, —NR$^6$R$^7$, —N(R$^6$)C(═NR$^8$)NR$^6$R$^7$, —SR$^6$, —S(O)$_{1-2}$R$^6$, —SO$_2$NR$^6$R$^7$, —CO$_2$R$^6$, —C(O)NR$^6$R$^7$, —C(O)N(OR$^6$)R$^7$, —C(═NR$^8$)NR$^6$R$^7$, —N(R$^6$)SO$_2$R$^6$, —C(O)R$^7$;

$R^4$ and $R^5$ are each independently selected from —H, halogen, and $C_{1-4}$alkyl; or $R^4$ and $R^5$ combined are a phenyl where the phenyl is optionally substituted with one to five groups independently selected from alkyl;

m is 0-3;

$R^6$ is selected from —H and $C_{1-8}$alkyl;

$R^7$ is selected from —H, and $C_{1-8}$alkyl; and $R^8$ is —H, —NO$_2$, —CN, —OR$^6$ or $C_{1-8}$alkyl.

6. The compound according to claim 5, wherein $R^{12}$ is an ethylene; $R^{10}$ is halogen; $R^4$ and $R^5$ are each independently selected from —H, halogen, and $C_{1-2}$alkyl; and m is 1-3; or a single stereoisomer, a single geometric isomer, a mixture of enantiomers, or a mixture of diastereomers thereof; and where the compound is optionally as a pharmaceutically acceptable salt thereof.

7. The compound according to claim 6, wherein each $R^{10}$ is independently selected from fluorine and chlorine; $R^4$ and $R^5$ are each independently selected from —H and $C_{1-2}$alkyl; and m is 1-3; or a single stereoisomer, a single geometric isomer, a mixture of enantiomers, or a mixture of diastereomers thereof; and where the compound is optionally as a pharmaceutically acceptable salt thereof.

8. The compound according to claim 7, wherein each $R^{10}$ is independently selected from fluorine and chlorine; $R^4$ and $R^5$ are each independently selected from —H and —CH$_3$; and m is 1-2; or a single stereoisomer, a single geometric isomer, a mixture of enantiomers, or a mixture of diastereomers thereof; and where the compound is optionally as a pharmaceutically acceptable salt thereof.

9. The compound according to claim 8, wherein $R^{10}$ is fluorine; $R^4$ and $R^5$ are each independently selected from —H and —CH$_3$; and m is 1; or a single stereoisomer, a single geometric isomer, a mixture of enantiomers, or a mixture of diastereomers thereof; and where the compound is optionally as a pharmaceutically acceptable salt thereof.

10. The compound according to claim 9, selected from:

| | |
|---|---|
| 49 | (3Z)-3-[(1-ethylpiperidin-4-yl)amino]-3-[(3-fluorophenyl)(1H-imidazol-2-yl)methylidene]-1,3-dihydro-2H-indol-2-one; |
| 51 | (3Z)-5-[(1-ethylpiperidin-4-yl)amino]-3-[(3-fluorophenyl)(4-methyl-1H-imidazol-2-yl)methylidene]-1,3-dihydro-2H-indol-2-one; |
| 58 | (3Z)-5-[(1-ethylpiperidin-4-yl)amino]-3-[(4-fluorophenyl)(1H-imidazol-2-yl)methylidene]-1,3-dihydro-2H-indol-2-one; |
| 70 | (3Z)-3-[(3-fluorophenyl)(4-methyl-1H-imidazol-2-yl)methylidene]-5-({1-[2-(methyloxy)ethyl]piperidin-4-yl}amino)-1,3-dihydro-2H-indol-2-one; |
| 78 | (3Z)-3-[(4-fluorophenyl)(1H-imidazol-2-yl)methylidene]-5-({1-[2-(methyloxy)ethyl]piperidin-4-yl}amino)-1,3-dihydro-2H-indol-2-one |
| 82 | (3Z)-3-[(3-fluorophenyl)(1H-imidazol-2-yl)methylidene]-5-{[1-(2-piperidin-1-ylethyl)piperidin-4-yl]amino}-1,3-dihydro-2H-indol-2-one; |
| 83 | (3Z)-3-[(3-fluorophenyl)(1H-imidazol-2-yl)methylidene]-5-{[1-(2-morpholin-4-ylethyl)piperidin-4-yl]amino}-1,3-dihydro-2H-indol-2-one; |
| 84 | (3Z)-5-({1-[2-(diethylamino)ethyl]piperidin-4-yl}amino)-3-[(3-fluorophenyl)(1H-imidazol-2-yl)methylidene]-1,3-dihydro-2H-indol-2-one; |
| 85 | (3Z)-3-[(3-fluorophenyl)(1H-imidazol-2-yl)methylidene]-5-{[1-(2-pyrrolidin-1-ylethyl)piperidin-4-yl]amino}-1,3-dihydro-2H-indol-2-one; |
| 106 | (3Z)-5-[(1-ethylpiperidin-4-yl)amino]-3-[(4-fluorophenyl)(4-methyl-1H-imidazol-2-yl)methylidene]-1,3-dihydro-2H-indol-2-one; |
| 107 | (3Z)-5-[(1-ethylpiperidin-4-yl)amino]-3-[(2-fluorophenyl)(1H-imidazol-2-yl)methylidene]-1,3-dihydro-2H-indol-2-one; and |
| 113 | (3Z)-3-[(2-fluorophenyl)(4-methyl-1H-imidazol-2-yl)methylidene]-5-[(1-ethylpiperidin-4-yl)amino]-1,3-dihydro-2H-indol-2-one; | and where the compound is optionally as a pharmaceutically acceptable salt thereof.

11. The Compound of claim 3 selected from

| | |
|---|---|
| 22 | (3Z)-3-[1H-benzimidazol-2-yl(phenyl)methylidene]-5-(piperidin-4-ylamino)-1,3-dihydro-2H-indol-2-one; |
| 28 | 2-(2-{2-[(Z)-{5-[(1-ethylpiperidin-4-yl)amino]-2-oxo-1,2-dihydro-3H-indol-3-ylidene}(phenyl)methyl]-1H-imidazol-4-yl}ethyl)-1H-isoindole-1,3(2H)-dione; |
| 30 | (3Z)-3-[1H-benzimidazol-2-yl(phenyl)methylidene]-5-{[1-(methylsulfonyl)piperidin-4-yl]amino}-1,3-dihydro-2H-indol-2-one; |
| 81 | (3Z)-3-[(3-fluorophenyl)(1H-imidazol-2-yl)methylidene]-5-(piperidin-4-ylamino)-1,3-dihydro-2H-indol-2-one; and |
| 93 | (3Z)-3-[(3-fluorophenyl)(1H-imidazol-2-yl)methylidene]-5-{[1-(methylsulfonyl)piperidin-4-yl]amino}-1,3-dihydro-2H-indol-2-one; | and where the compound is optionally as a pharmaceutically acceptable salt thereof.

12. The compound of claim 4 selected from

| | |
|---|---|
| 6 | (3Z)-5-[(1-ethylpiperidin-4-yl)amino]-3-[[5-(methyloxy)-1H-benzimidazol-2-yl](4-methylphenyl)methylidene]-1,3-dihydro-2H-indol-2-one; |
| 12 | (3Z)-3-[1H-benzimidazol-2-yl(4-methylphenyl)methylidene]-5-[(1-ethylpiperidin-4-yl)amino]-1,3-dihydro-2H-indol-2-one; |
| 13 | (3Z)-5-[(1-ethylpiperidin-4-yl)amino]-3-[1H-imidazol-2-yl(4-methylphenyl)methylidene]-1,3-dihydro-2H-indol-2-one; |
| 50 | (3Z)-3-[1H-benzimidazol-2-yl(3-fluoro-4-methylphenyl)methylidene]-5-[(1-ethylpiperidin-4-yl)amino]-1,3-dihydro-2H-indol-2-one; |
| 52 | (3Z)-3-[1H-benzimidazol-2-yl(4-fluoro-3-methylphenyl)methylidene]-5-[(1-ethylpiperidin-4-yl)amino]-1,3-dihydro-2H-indol-2-one; |
| 57 | (3Z)-5-[(1-ethylpiperidin-4-yl)amino]-3-[(3-fluoro-4-methylphenyl)(1H-imidazol-2-yl)methylidene]-1,3-dihydro-2H-indol-2-one; |
| 59 | (3Z)-5-[(1-ethylpiperidin-4-yl)amino]-3-[1H-imidazol-2-yl(4-propylphenyl)methylidene]-1,3-dihydro-2H-indol-2-one; |
| 63 | (3Z)-3-[(3-fluoro-4-methylphenyl)(1H-imidazol-2-yl)methylidene]-5-({1-[2-(methyloxy)ethyl]piperidin-4-yl}amino)-1,3-dihydro-2H-indol-2-one; |
| 64 | (3Z)-5-[(1-ethylpiperidin-4-yl)amino]-3-[(4-methyl-1H-imidazol-2-yl)(4-methylphenyl)methylidene]-1,3-dihydro-2H-indol-2-one; |
| 67 | (3Z)-5-[(1-ethylpiperidin-4-yl)amino]-3-[(3-fluoro-4-methylphenyl)(4-methyl-1H-imidazol-2-yl)methylidene]-1,3-dihydro-2H-indol-2-one; |
| 69 | (3Z)-3-[1H-imidazol-2-yl(4-methylphenyl)methylidene]-5-({1-[2-(methyloxy)ethyl]piperidin-4-yl}amino)-1,3-dihydro-2H-indol-2-one; |
| 77 | (3Z)-3-[(4-methyl-1H-imidazol-2-yl)(4-methylphenyl)methylidene]-5-({1-[2-(methyloxy)ethyl]piperidin-4-yl}amino)-1,3-dihydro-2H-indol-2-one; |
| 86 | (3Z)-3-[1H-imidazol-2-yl(4-methylphenyl)methylidene]-5-[(1-methylpiperidin-4-yl)amino]-1,3-dihydro-2H-indol-2-one; |
| 88 | ethyl 2-{(Z)-(3-fluorophenyl)[5-({1-[2-(methyloxy)ethyl]piperidin-4-yl}amino)-2-oxo-1,2-dihydro-3H-indol-3-ylidene]methyl}-4-methyl-1H-imidazole-5-carboxylate; |

-continued 94 (3Z)-3-[1H-imidazol-2-yl(4-propylphenyl)methylidene]-5-({1-[2-(methyloxy)ethyl]piperidin-4-yl}amino)-1,3-dihydro-2H-indol-2-one;
95 (3Z)-5-[(1-ethylpiperidin-4-yl)amino]-3-[(3-fluorophenyl)(4-phenyl-1H-imidazol-2-yl)methylidene]-1,3-dihydro-2H-indol-2-one;
96 (3Z)-3-[(3-fluorophenyl)(4-phenyl-1H-imidazol-2-yl)methylidene]-5-({1-[2-(methyloxy)ethyl]piperidin-4-yl}amino)-1,3-dihydro-2H-indol-2-one; and
97 (3Z)-3-[(3-fluoro-4-methylphenyl)(4-methyl-1H-imidazol-2-yl)methylidene]-5-({1-[2-(methyloxy)ethyl]piperidin-4-yl}amino)-1,3-dihydro-2H-indol-2-one;

and where the compound is optionally as a pharmaceutically acceptable salt thereof.

13. The compound of claim 5 selected from 3 (3Z)-5-[(1-ethylpiperidin-4-yl)amino]-3-[[5-(methyloxy)-1H-benzimidazol-2-yl](phenyl)methylidene]-1,3-dihydro-2H-indol-2-one;
4 (3Z)-5-[(1-ethylpiperidin-4-yl)amino]-3-[1H-imidazol-2-yl(phenyl)methylidene]-1,3-dihydro-2H-indol-2-one;
5 (3Z)-5-[(1-ethylpiperidin-4-yl)amino]-3-{[5-(methyloxy)-1H-benzimidazol-2-yl][4-(methyloxy)phenyl]methylidene}-1,3-dihydro-2H-indol-2-one;
7 (3Z)-3-[1H-benzimidazol-2-yl(4-nitrophenyl)methylidene]-5-[(1-ethylpiperidin-4-yl)amino]-1,3-dihydro-2H-indol-2-one;
8 (3Z)-3-{1H-benzimidazol-2-yl[4-(methyloxy)phenyl]methylidene}-5-[(1-ethylpiperidin-4-yl)amino]-1,3-dihydro-2H-indol-2-one;
9 (3Z)-3-[1H-benzimidazol-2-yl(phenyl)methylidene]-5-[(1-ethylpiperidin-4-yl)amino]-1,3-dihydro-2H-indol-2-one;
11 (3Z)-3-[(4-aminophenyl)(1H-benzimidazol-2-yl)methylidene]-5-[(1-ethylpiperidin-4-yl)amino]-1,3-dihydro-2H-indol-2-one;
15 (3Z)-5-[(1-ethylpiperidin-4-yl)amino]-3-{1H-imidazol-2-yl[4-(methyloxy)phenyl]methylidene}-1,3-dihydro-2H-indol-2-one;
16 (3Z)-3-[1H-benzimidazol-2-yl(4-fluorophenyl)methylidene]-5-[(1-ethylpiperidin-4-yl)amino]-1,3-dihydro-2H-indol-2-one;
17 (3Z)-3-[1H-benzimidazol-2-yl(3,5-difluorophenyl)methylidene]-5-[(1-ethylpiperidin-4-yl)amino]-1,3-dihydro-2H-indol-2-one;
18 (3Z)-3-[1H-benzimidazol-2-yl(3-fluorophenyl)methylidene]-5-[(1-ethylpiperidin-4-yl)amino]-1,3-dihydro-2H-indol-2-one;
19 (3Z)-3-[1H-benzimidazol-2-yl(3-nitrophenyl)methylidene]-5-[(1-ethylpiperidin-4-yl)amino]-1,3-dihydro-2H-indol-2-one;
21 (3Z)-3-[(3-aminophenyl)(1H-benzimidazol-2-yl)methylidene]-5-[(1-ethylpiperidin-4-yl)amino]-1,3-dihydro-2H-indol-2-one;
23 3-((Z)-1H-benzimidazol-2-yl{5-[(1-ethylpiperidin-4-yl)amino]-2-oxo-1,2-dihydro-3H-indol-3-ylidene}methyl)benzenecarboximidamide;
24 (3Z)-3-[1H-benzimidazol-2-yl(phenyl)methylidene]-5-({1-[2-(methyloxy)ethyl]piperidin-4-yl}amino)-1,3-dihydro-2H-indol-2-one;
26 (3Z)-3-{1H-benzimidazol-2-yl[3-(methyloxy)phenyl]methylidene}-5-[(1-ethylpiperidin-4-yl)amino]-1,3-dihydro-2H-indol-2-one;
27 (3Z)-3-[1H-benzimidazol-2-yl(3-chlorophenyl)methylidene]-5-[(1-ethylpiperidin-4-yl)amino]-1,3-dihydro-2H-indol-2-one;
29 (3Z)-3-[1H-benzimidazol-2-yl(phenyl)methylidene]-5-({1-[2-(dimethylamino)ethyl]piperidin-4-yl}amino)-1,3-dihydro-2H-indol-2-one;
38 (3Z)-3-[1H-benzimidazol-2-yl(3-chlorophenyl)methylidene]-5-({1-[2-(methyloxy)ethyl]piperidin-4-yl}amino)-1,3-dihydro-2H-indol-2-one;
39 (3Z)-3-{1H-benzimidazol-2-yl[3-(methyloxy)phenyl]methylidene}-5-({1-[2-(methyloxy)ethyl]piperidin-4-yl}amino)-1,3-dihydro-2H-indol-2-one;
42 (3Z)-3-[1H-benzimidazol-2-yl(3,5-difluorophenyl)methylidene]-5-({1-[2-(methyloxy)ethyl]piperidin-4-yl}amino)-1,3-dihydro-2H-indol-2-one
45 (3Z)-3-[1H-benzimidazol-2-yl(4-chlorophenyl)methylidene]-5-[(1-ethylpiperidin-4-yl)amino]-1,3-dihydro-2H-indol-2-one;
46 (3Z)-3-[1H-benzimidazol-2-yl(3-fluorophenyl)methylidene]-5-({1-[2-(methyloxy)ethyl]piperidin-4-yl}amino)-1,3-dihydro-2H-indol-2-one;
47 (3Z)-3-[1H-benzimidazol-2-yl(4-fluorophenyl)methylidene]-5-({1-[2-(methyloxy)ethyl]piperidin-4-yl}amino)-1,3-dihydro-2H-indol-2-one;
55 (3Z)-3-[(5-chloro-1H-benzimidazol-2-yl)(phenyl)methylidene]-5-[(1-ethylpiperidin-4-yl)amino]-1,3-dihydro-2H-indol-2-one;

-continued 56 (3Z)-3-[(5-chloro-1H-benzimidazol-2-yl)(3,5-difluorophenyl)methylidene]-5-[(1-ethylpiperidin-4-yl)amino]-1,3-dihydro-2H-indol-2-one;
60 (3Z)-5-[(1-ethylpiperidin-4-yl)amino]-3-{1H-imidazol-2-yl[4-(trifluoromethyl)phenyl]methylidene}-1,3-dihydro-2H-indol-2-one;
61 (3E)-3-[(3,5-difluorophenyl)(5-fluoro-1H-benzimidazol-2-yl)methylidene]-5-[(1-ethylpiperidin-4-yl)amino]-1,3-dihydro-2H-indol-2-one;
62 (3Z)-3-[(3,5-difluorophenyl)(5-fluoro-1H-benzimidazol-2-yl)methylidene]-5-[(1-ethylpiperidin-4-yl)amino]-1,3-dihydro-2H-indol-2-one;
65 (3Z)-5-[(1-ethylpiperidin-4-yl)amino]-3-[[3-fluoro-4-(trifluoromethyl)phenyl](1H-imidazol-2-yl)methylidene]-1,3-dihydro-2H-indol-2-one;
71 (3Z)-3-{1H-imidazol-2-yl[4-(trifluoromethyl)phenyl]methylidene}-5-({1-[2-(methyloxy)ethyl]piperidin-4-yl}amino)-1,3-dihydro-2H-indol-2-one;
72 (3Z)-3-[(5-chloro-1H-benzimidazol-2-yl)(phenyl)methylidene]-5-({1-[2-(methyloxy)ethyl]piperidin-4-yl}amino)-1,3-dihydro-2H-indol-2-one;
89 (3Z)-3-[1H-imidazol-2-yl(phenyl)methylidene]-5-({1-[2-(methyloxy)ethyl]piperidin-4-yl}amino)-1,3-dihydro-2H-indol-2-one;
90 (3Z)-3-{1H-imidazol-2-yl[4-(methyloxy)phenyl]methylidene}-5-({1-[2-(methyloxy)ethyl]piperidin-4-yl}amino)-1,3-dihydro-2H-indol-2-one;
92 (3Z)-3-[[3-fluoro-4-(trifluoromethyl)phenyl](1H-imidazol-2-yl)methylidene]-5-({1-[2-(methyloxy)ethyl]piperidin-4-yl}amino)-1,3-dihydro-2H-indol-2-one;
100 (3Z)-5-[(1-ethylpiperidin-4-yl)amino]-3-[[2-fluoro-4-(trifluoromethyl)phenyl](1H-imidazol-2-yl)methylidene]-1,3-dihydro-2H-indol-2-one;
101 (3Z)-5-[(1-ethylpiperidin-4-yl)amino]-3-{(4-methyl-1H-imidazol-2-yl)[4-(trifluoromethyl)phenyl]methylidene}-1,3-dihydro-2H-indol-2-one;
103 (3Z)-5-[(1-ethylpiperidin-4-yl)amino]-3-[[3-fluoro-4-(trifluoromethyl)phenyl](4-methyl-1H-imidazol-2-yl)methylidene]-1,3-dihydro-2H-indol-2-one;
108 (3Z)-5-[(1-ethylpiperidin-4-yl)amino]-3-[[2-fluoro-4-(trifluoromethyl)phenyl](4-methyl-1H-imidazol-2-yl)methylidene]-1,3-dihydro-2H-indol-2-one;
114 (3Z)-3-[(3-trifluoromethylphenyl)(1H-imidazol-2-yl)methylidene]-5-[(1-ethylpiperidin-4-yl)amino]-1,3-dihydro-2H-indol-2-one;
115 (3Z)-3-[(3-trifluoromethylphenyl)(4-methyl-1H-imidazol-2-yl)methylidene]-5-[(1-ethylpiperidin-4-yl)amino]-1,3-dihydro-2H-indol-2-one;
116 (3Z)-3-[(2,4-dichloro-5-fluorophenyl)(1H-imidazol-2-yl)methylidene]-5-[(1-ethylpiperidin-4-yl)amino]-1,3-dihydro-2H-indol-2-one; and
117 (3Z)-3-[(2,4-dichloro-5-fluorophenyl)(4-methyl-1H-imidazol-2-yl)methylidene]-5-[(1-ethylpiperidin-4-yl)amino]-1,3-dihydro-2H-indol-2-one;

where the compound is optionally as a pharmaceutically acceptable salt thereof.

14. The compound of claim 8 selected from 40 (3Z)-3-[(3-chlorophenyl)(1H-imidazol-2-yl)methylidene]-5-({1-[2-(methyloxy)ethyl]piperidin-4-yl}amino)-1,3-dihydro-2H-indol-2-one
41 (3Z)-3-[(3-fluorophenyl)(1H-imidazol-2-yl)methylidene]-5-({1-[2-(methyloxy)ethyl]piperidin-4-yl}amino)-1,3-dihydro-2H-indol-2-one
48 (3Z)-3-[(3-chlorophenyl)(1H-imidazol-2-yl)methylidene]-5-[(1-ethylpiperidin-4-yl)amino]-1,3-dihydro-2H-indol-2-one
53 (3Z)-3-[(3-chloro-4-fluorophenyl)(1H-imidazol-2-yl)methylidene]-5-[(1-ethylpiperidin-4-yl)amino]-1,3-dihydro-2H-indol-2-one
54 (3Z)-3-[(3,4-difluorophenyl)(1H-imidazol-2-yl)methylidene]-5-[(1-ethylpiperidin-4-yl)amino]-1,3-dihydro-2H-indol-2-one
66 (3Z)-3-[(4-chlorophenyl)(1H-imidazol-2-yl)methylidene]-5-[(1-ethylpiperidin-4-yl)amino]-1,3-dihydro-2H-indol-2-one
73 (3Z)-3-[(3,5-difluorophenyl)(1H-imidazol-2-yl)methylidene]-5-[(1-ethylpiperidin-4-yl)amino]-1,3-dihydro-2H-indol-2-one -continued

| | |
|---|---|
| 74 | (3Z)-3-[(3,5-difluorophenyl)(4-methyl-1H-imidazol-2-yl)methylidene]-5-[(1-ethylpiperidin-4-yl)amino]-1,3-dihydro-2H-indol-2-one |
| 75 | (3Z)-3-[(3,5-difluorophenyl)(1H-imidazol-2-yl)methylidene]-5-({1-[2-(methyloxy)ethyl]piperidin-4-yl}amino)-1,3-dihydro-2H-indol-2-one |
| 76 | (3Z)-3-[(3,5-difluorophenyl)(4-methyl-1H-imidazol-2-yl)methylidene]-5-({1-[2-(methyloxy)ethyl]piperidin-4-yl}amino)-1,3-dihydro-2H-indol-2-one |
| 79 | (3Z)-3-[(3,4-difluorophenyl)(1H-imidazol-2-yl)methylidene]-5-({1-[2-(methyloxy)ethyl]piperidin-4-yl}amino)-1,3-dihydro-2H-indol-2-one |
| 80 | (3Z)-3-[(3-chloro-4-fluorophenyl)(1H-imidazol-2-yl)methylidene]-5-({1-[2-(methyloxy)ethyl]piperidin-4-yl}amino)-1,3-dihydro-2H-indol-2-one |
| 91 | (3Z)-3-[(4-chlorophenyl)(1H-imidazol-2-yl)methylidene]-5-({1-[2-(methyloxy)ethyl]piperidin-4-yl}amino)-1,3-dihydro-2H-indol-2-one |
| 102 | (3Z)-3-[(4-chlorophenyl)(4-methyl-1H-imidazol-2-yl)methylidene]-5-[(1-ethylpiperidin-4-yl)amino]-1,3-dihydro-2H-indol-2-one |
| 104 | (3Z)-3-[(3,4-difluorophenyl)(4-methyl-1H-imidazol-2-yl)methylidene]-5-[(1-ethylpiperidin-4-yl)amino]-1,3-dihydro-2H-indol-2-one |
| 105 | (3Z)-3-[(3-chloro-4-fluorophenyl)(4-methyl-1H-imidazol-2-yl)methylidene]-5-[(1-ethylpiperidin-4-yl)amino]-1,3-dihydro-2H-indol-2-one |
| 109 | (3Z)-3-[(2,3-difluorophenyl)(1H-imidazol-2-yl)methylidene]-5-[(1-ethylpiperidin-4-yl)amino]-1,3-dihydro-2H-indol-2-one |
| 110 | (3Z)-3-[(2,3-difluorophenyl)(4-methyl-1H-imidazol-2-yl)methylidene]-5-[(1-ethylpiperidin-4-yl)amino]-1,3-dihydro-2H-indol-2-one |
| 111 | (3Z)-3-[(2,4-difluorophenyl)(4-methyl-1H-imidazol-2-yl)methylidene]-5-[(1-ethylpiperidin-4-yl)amino]-1,3-dihydro-2H-indol-2-one |
| 112 | (3Z)-3-[(2,4-difluorophenyl)(1H-imidazol-2-yl)methylidene]-5-[(1-ethylpiperidin-4-yl)amino]-1,3-dihydro-2H-indol-2-one |
| 118 | (3Z)-3-[(4-chloro-2-fluorophenyl)(4-methyl-1H-imidazol-2-yl)methylidene]-5-[(1-ethylpiperidin-4-yl)amino]-1,3-dihydro-2H-indol-2-one | where the compound is optionally as a pharmaceutically acceptable salt thereof.

15. The compound of claim 10 named (3Z)-3-[(2-fluorophenyl)(4-methyl-1H-imidazol-2-yl)methylidene]-5-[(1-ethylpiperidin-4-yl)amino]-1,3-dihydro-2H-indol-2-one; where the compound is optionally as a pharmaceutically acceptable salt thereof.

16. The compound of claim 10 named (3Z)-5-[(1-ethylpiperidin-4-yl)amino]-3-[(3-fluorophenyl)(4-methyl-1H-imidazol-2-yl)methylidene]-1,3-dihydro-2H-indol-2-one; where the compound is optionally as a pharmaceutically acceptable salt thereof.

17. The Compound of claim 1 selected from (3Z)-5-[(1-ethylpiperidin-4-yl)amino]-3-{1H-imidazol-2-yl[6-(trifluoromethyl)pyridin-3-yl]methylidene}-1,3-dihydro-2H-indol-2-one and (3Z)-3-{1H-imidazol-2-yl[6-(trifluoromethyl)pyridin-3-yl]methylidene}-5-({1-[2-(methyloxy)ethyl]piperidin-4-yl}amino)-1,3-dihydro-2H-indol-2-one; or a single geometric isomer thereof, optionally as a pharmaceutically acceptable salt thereof.

18. A pharmaceutical composition comprising a compound according to claim 1, 3, 4, 5, 10, 11, 12, 13, 14, or 17 or a single stereoisomer, a single geometric isomer, a mixture of enantiomers, or a mixture of diastereomers thereof, where the compound is optionally as a pharmaceutically acceptable salt thereof; and a pharmaceutically acceptable carrier.

19. A pharmaceutical composition comprising a compound according to claim 15 or 16, where the compound is optionally as a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 7,626,031 B2
APPLICATION NO. : 10/533555
DATED : December 1, 2009
INVENTOR(S) : Xu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1108 days.

Signed and Sealed this

Twenty-first Day of December, 2010

David J. Kappos
*Director of the United States Patent and Trademark Office*